(12) United States Patent
Lim et al.

(10) Patent No.: US 11,692,222 B2
(45) Date of Patent: Jul. 4, 2023

(54) ANIMAL MODEL OF NON-ALCOHOLIC LIVER DISEASE AND COMPOSITION OF DIAGNOSIS, PREVENTION OR TREATMENT FOR NON-ALCOHOLIC LIVER DISEASE

(71) Applicant: KOREA ADVANCED INSTITUTE OF SCIENCE AND TECHNOLOGY, Daejeon (KR)

(72) Inventors: Dae-Sik Lim, Daejeon (KR); Sun Hye Jeong, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 1040 days.

(21) Appl. No.: 16/444,174

(22) Filed: Jun. 18, 2019

(65) Prior Publication Data

US 2020/0024660 A1 Jan. 23, 2020

(30) Foreign Application Priority Data

Jun. 19, 2018 (KR) .................. 10-2018-0070298

(51) Int. Cl.
*C12Q 1/6874* (2018.01)

(52) U.S. Cl.
CPC ..... *C12Q 1/6874* (2013.01); *C12Q 2600/136* (2013.01); *C12Q 2600/158* (2013.01)

(58) Field of Classification Search
None
See application file for complete search history.

(56) References Cited

FOREIGN PATENT DOCUMENTS

JP 6020791 10/2013

OTHER PUBLICATIONS

Ardestani et al. Hippo Signaling: Key Emerging Pathway in Cellular and Whole-Body Metabolism. Trends in Endocrinology & Metabolism (2018) 29: 7. Electronically published May 5, 2018. (Year: 2018).*

Yasuo Horie et al., "Hepatocyte-specific Pten deficiency results in steatohepatitis and hepatocellular carcinomas", The Journal of Clinical Investigation, Jun. 2004, vol. 113, No. 12, p. 1774-1783.

Sun-Hye Jeong et al., "Hippo-mediated suppression of IRS2/AKT signaling prevents hepatic steatosis and liver cancer", The Journal of Clinical Investigation, Mar. 2018, vol. 128, No. 3, p. 1010-1025.

Sun-Hye Jeong et al., "Insulin receptor substrate 2: a bridge between Hippo and AKT pathways", BMB Reports, 2018, vol. 51, No. 5, p. 209-210.

Sun Hye Jeong, "A linker between Hippo and AKT pathways", Life Science and Bioengineering, Biological Sciences, KAIST Compass, Apr. 23, 2018.

An interview conducted with the inventor 'Sun Hye Jeoun', KAIST, Department of Biological Sciences, Mar. 5, 2018.

Sun-Hye Jeong, "Hippo-mediated suppression of IRS2/AKT signaling prevents hepatic steatosis and liver cancer", The Journal of Clinical Investigation, Published Feb. 5, 2018, doi:10.1172/JCI95802, BRIC, Abstract only.

Paul Angulo, "Long-Term Mortality in Nafld. is Liver Histology of Any Prognostic Significance?", Hepatology, Feb. 2010, vol. 51, No. 2, p. 373-375.

Kevin Wei et al., "A liver HIF-2α/IRS2 pathway sensitizes hepatic insulin signaling and is modulated by VEGF inhibition", Nature Medicine, Oct. 2013, vol. 19, No. 10, p. 1331-1337.

Xiaoling Xu et al., "Induction of intrahepatic cholangiocellular carcinoma by liverspecific disruption of Smad4 and Pten in mice", J Clin Invest, vol. 116, No. 7, pp. 1843-1852, Jul. 2006.

Xiaoiin Luo et al., "Dual Shp2 and Pten Deficiencies Promote Nonalcoholic Steatohepatitis and Genesis of Liver Tumor-Initiating Cells", Cell Reports vol. 17, No. 11, pp. 2979-2993, Dec. 13, 2016.

Bo Hwa Sohn et al., "Inactivation of Hippo Pathway Is Significantly Associated with Poor Prognosis in Hepatocellular Carcinoma", Clinical Cancer Research vol. 22, No. 5, pp. 1256-1264, Oct. 12, 2015.

Audrey W. Hong et al., "The Hippo pathway in intestinal regeneration and disease", Nature Reviews Gastroenterology & Hepatology vol. 13, No. 6, pp. 324-337, Apr. 5, 2016.

* cited by examiner

*Primary Examiner* — Allison M Fox
*Assistant Examiner* — Alyssa G Weston
(74) *Attorney, Agent, or Firm* — Lex IP Meister, PLLC

(57) ABSTRACT

The present invention provides a method of manufacturing an animal model of non-alcoholic liver disease by using correlation among metabolic dysregulations through AKT regulation by Hippo signaling, and an animal model prepared by the method above, and a screening method of a therapeutic agent by using the animal model.

9 Claims, 59 Drawing Sheets
(44 of 59 Drawing Sheet(s) Filed in Color)
Specification includes a Sequence Listing.

[FIG 1a]
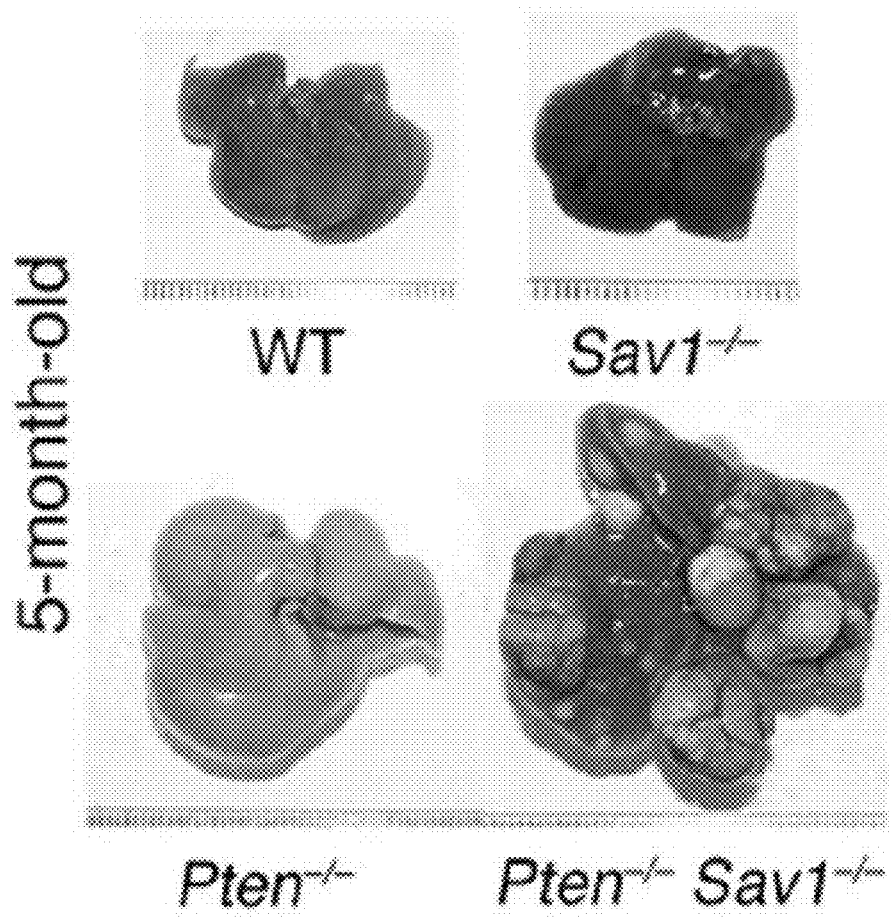

[FIG 1b]
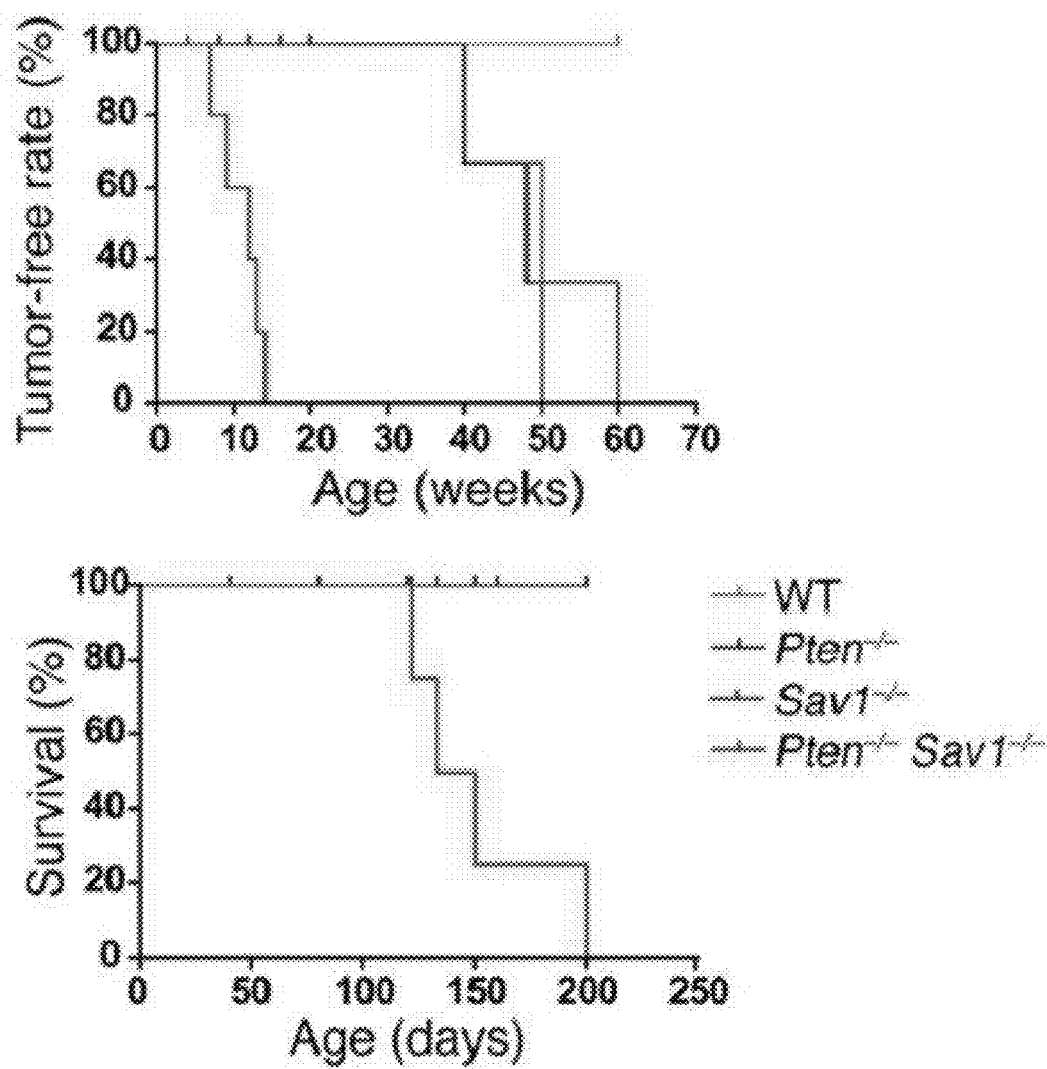

[FIG 1c]
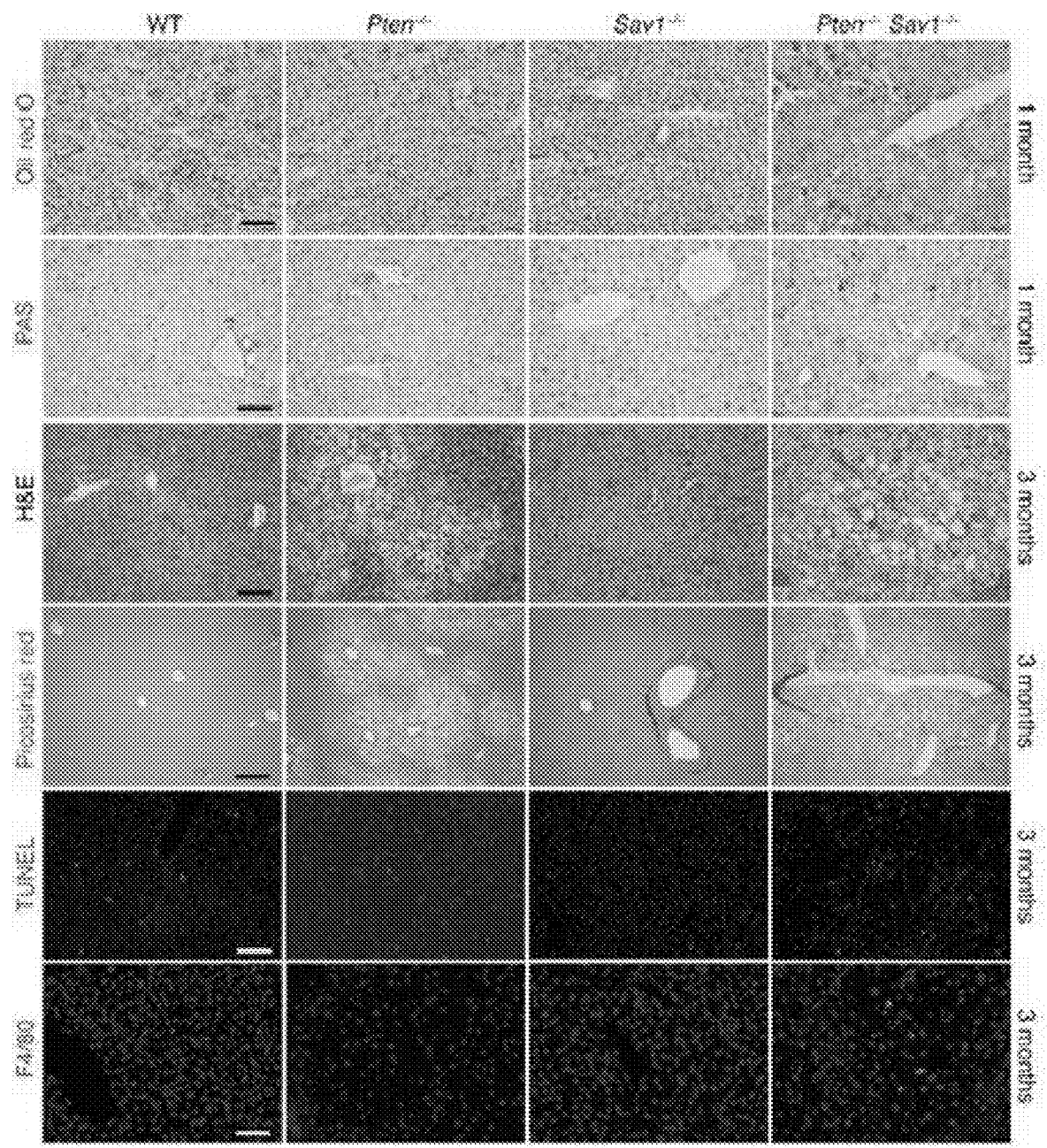

[FIG 1d]
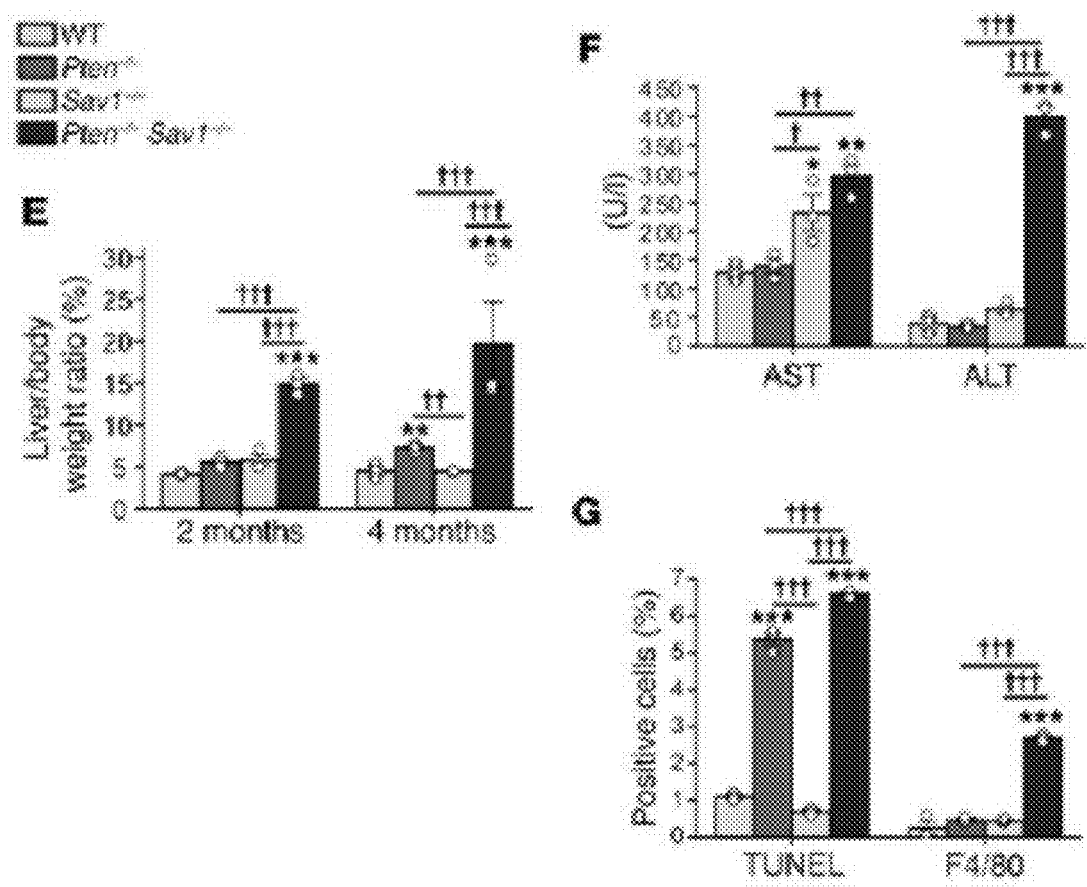

[FIG 2a]
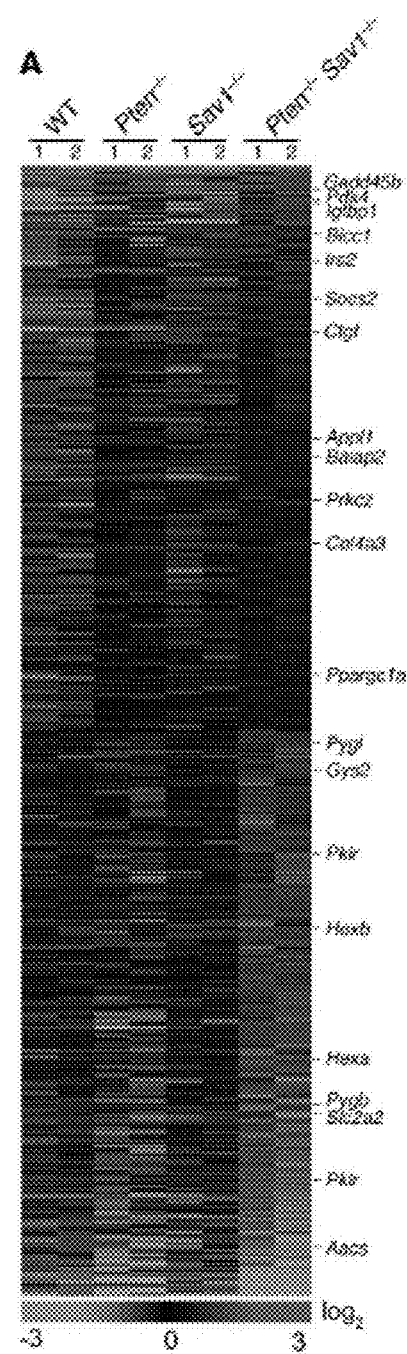

[FIG 2b]
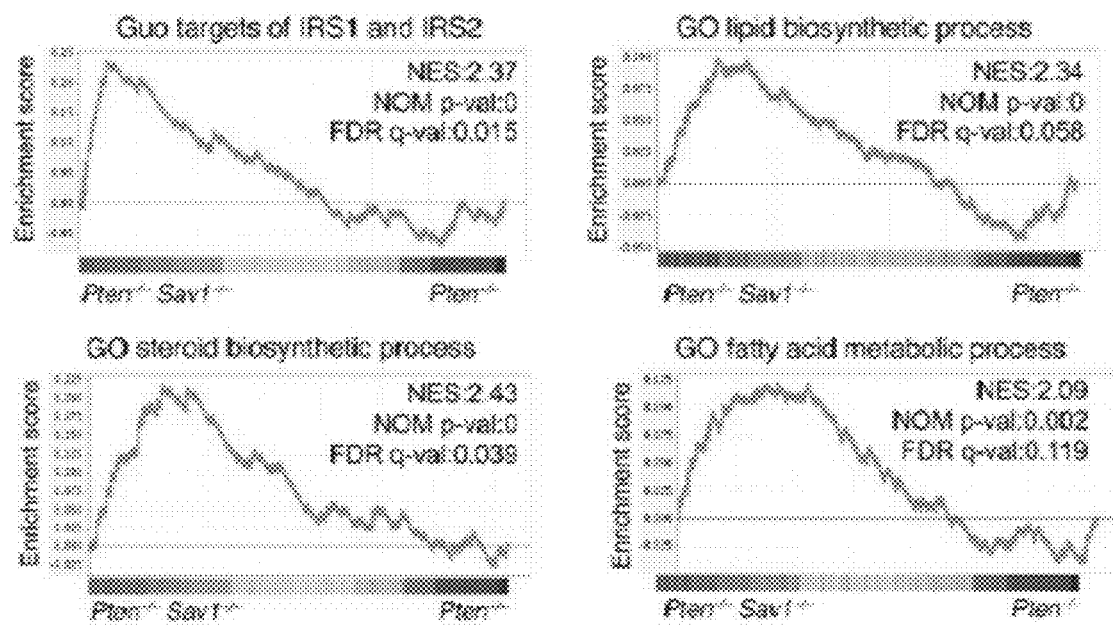

[FIG 2c]
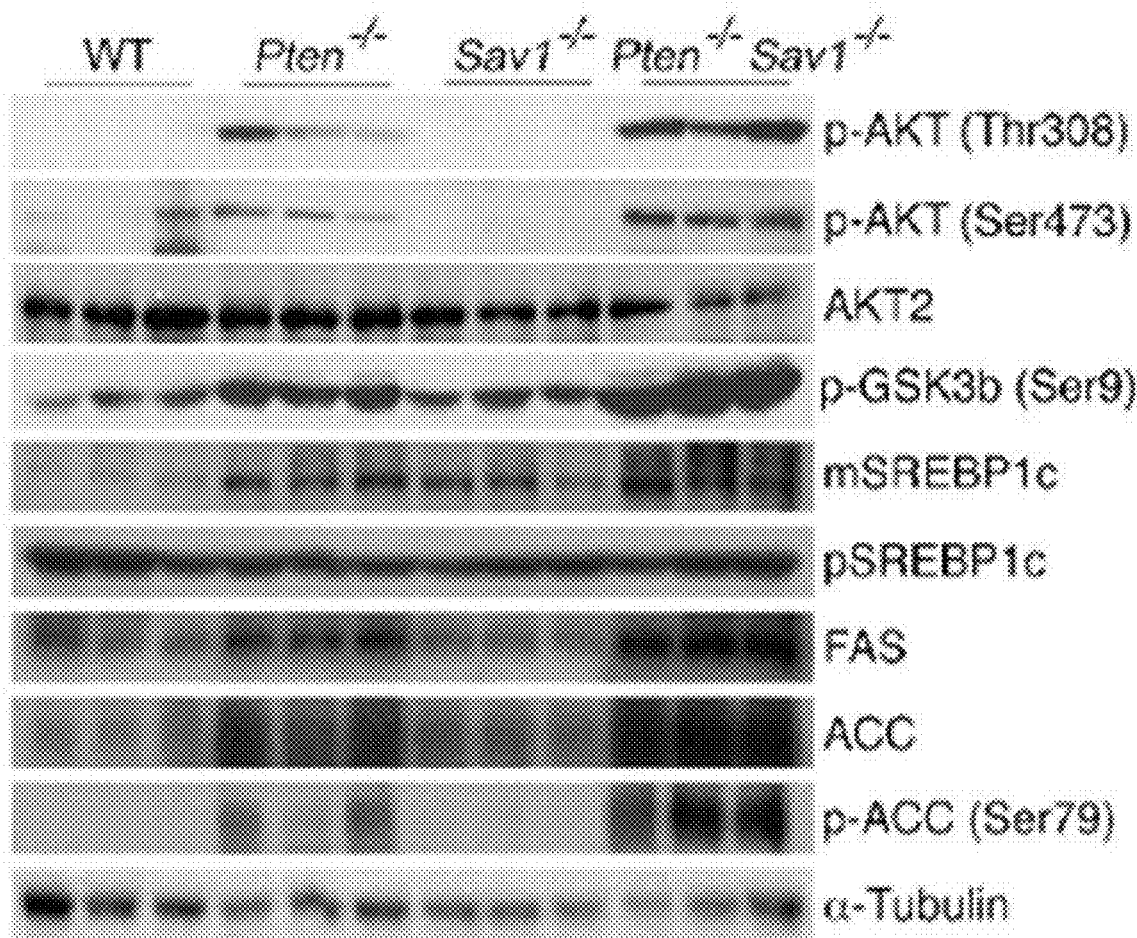

[FIG 2d]
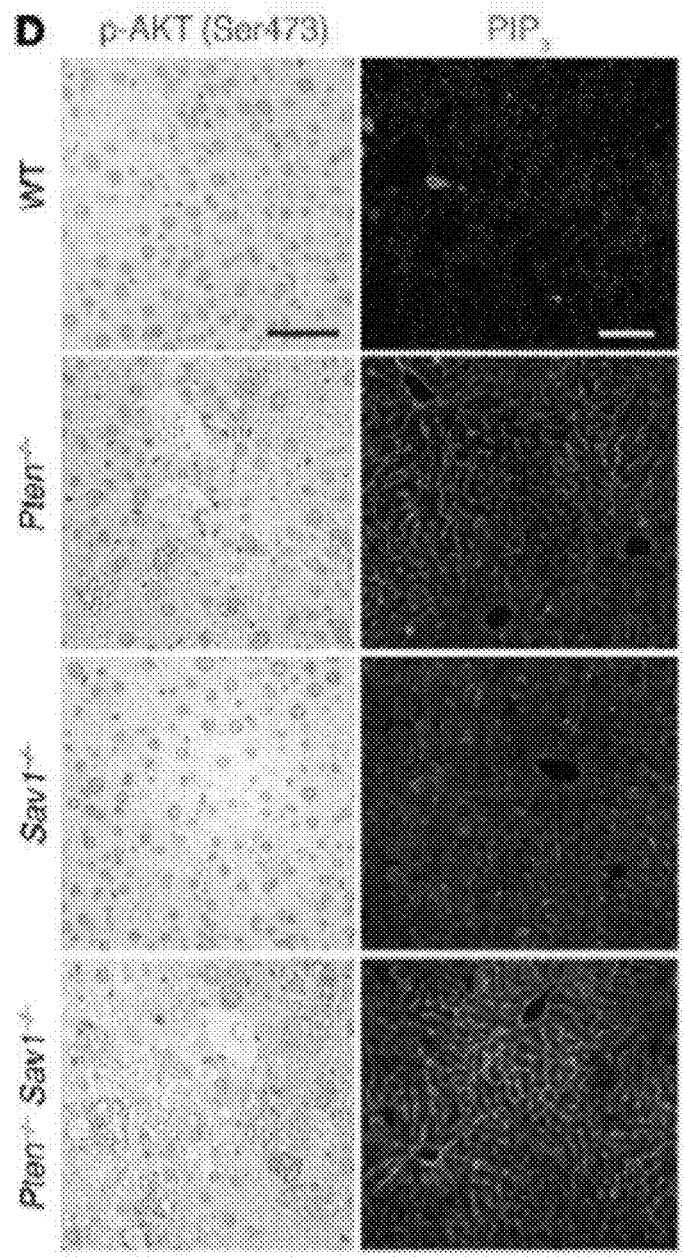

[FIG 2e]
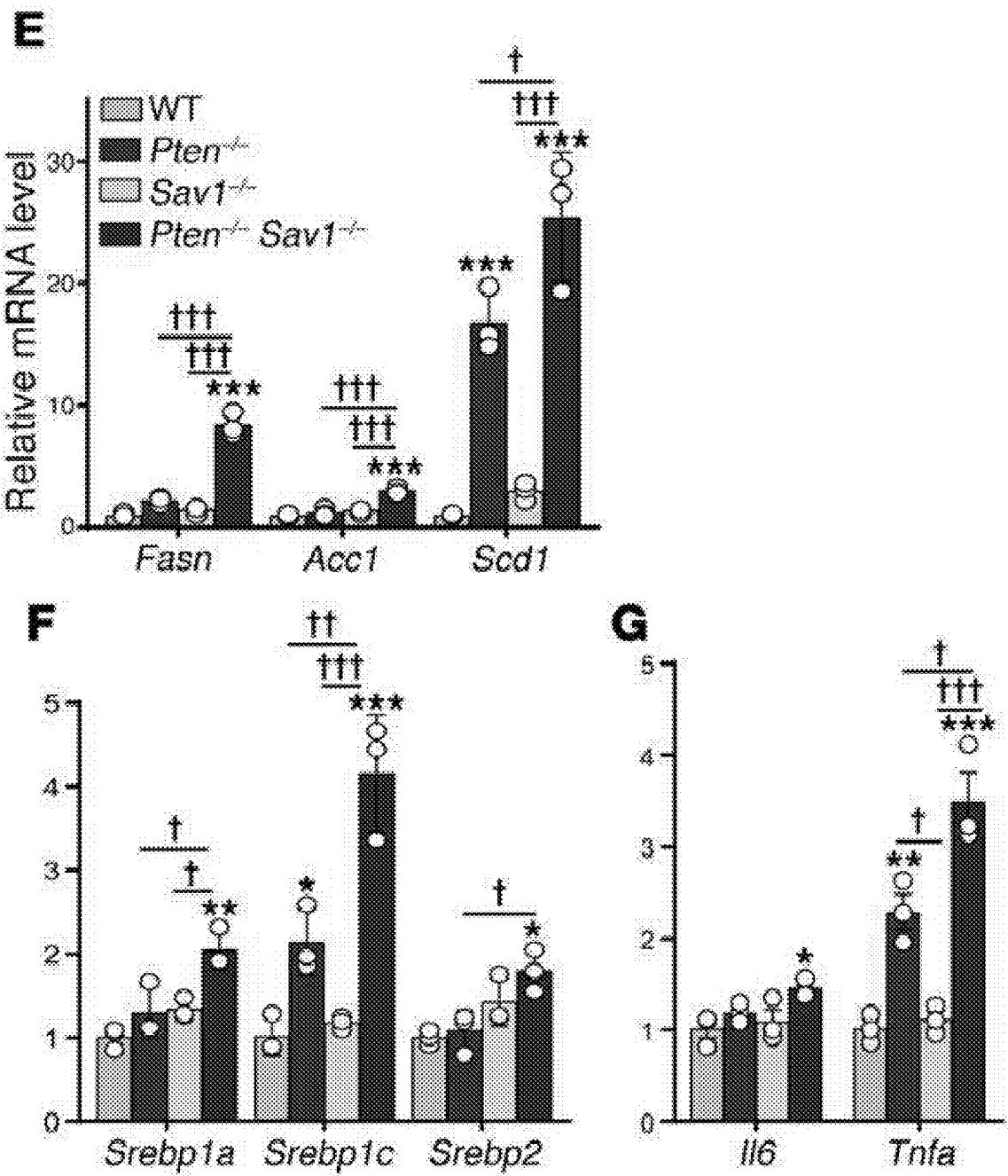

[FIG 3a]
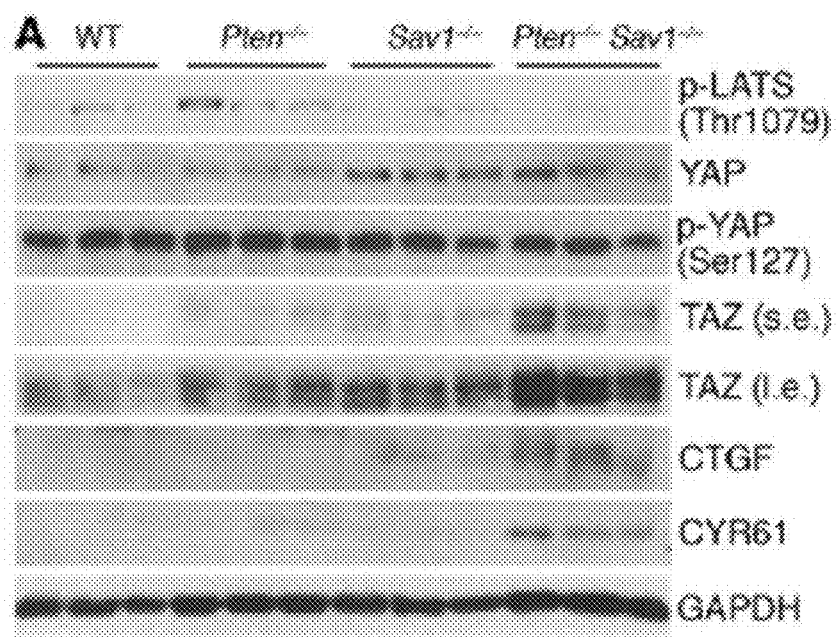

[FIG 3b]
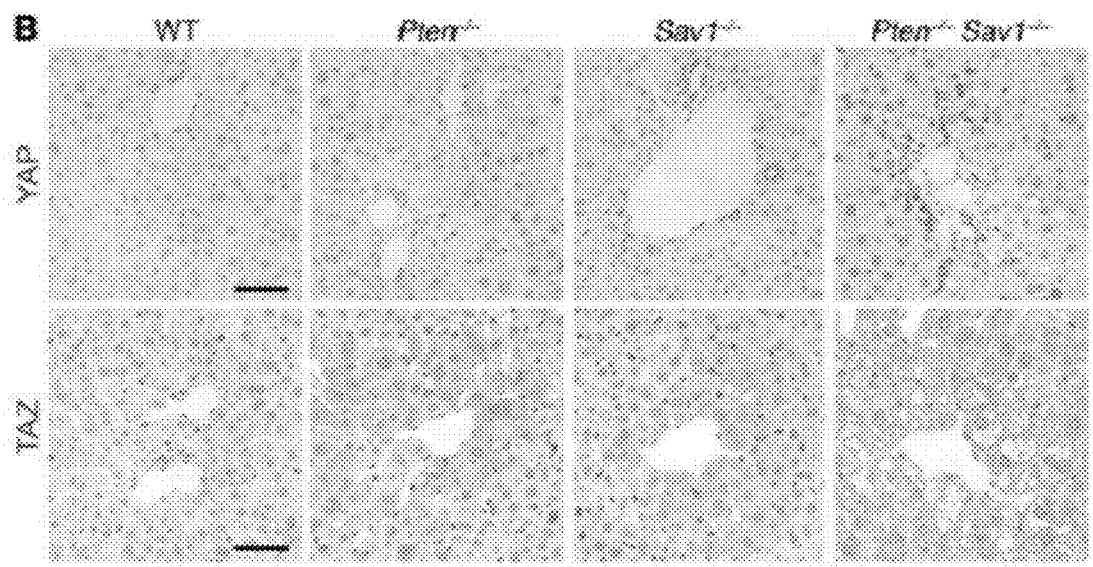

[FIG 3c]
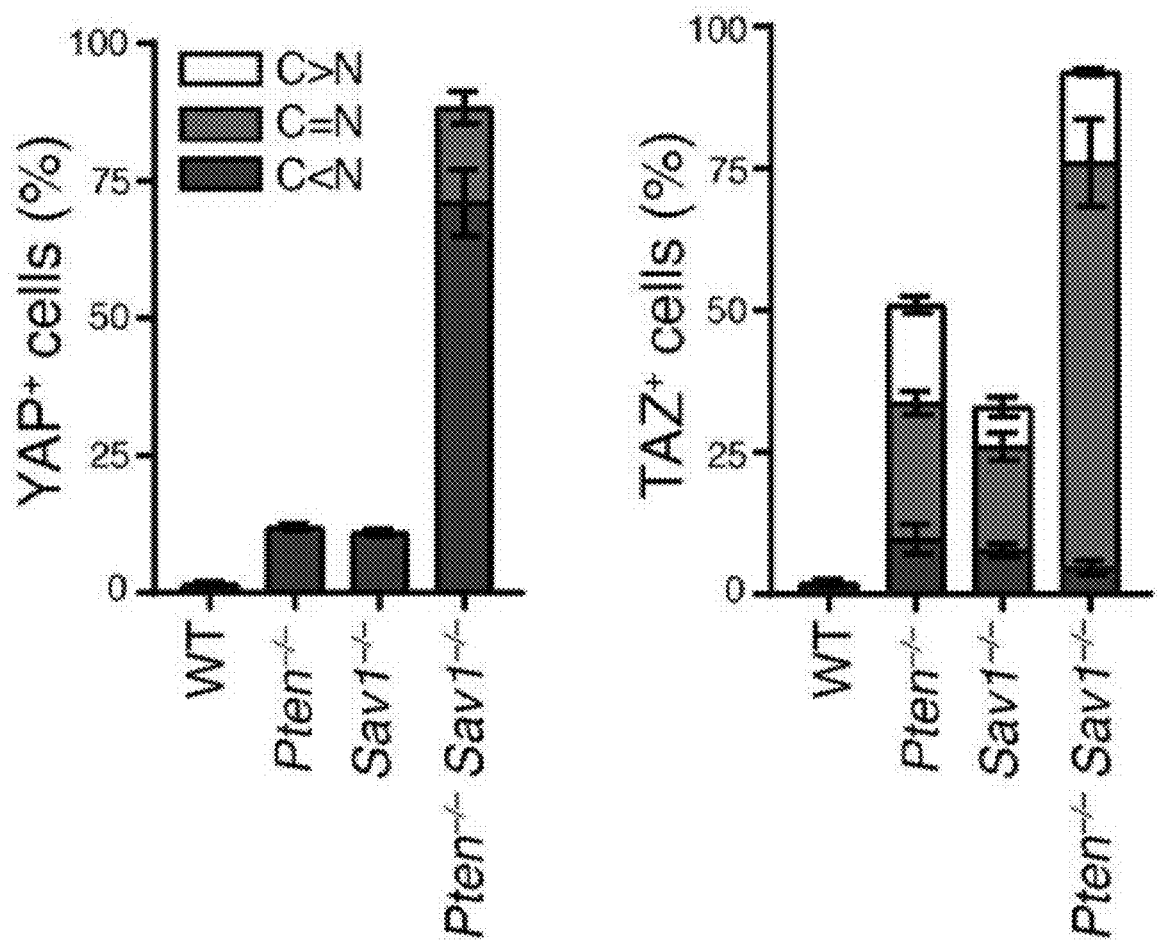

[FIG 3d]
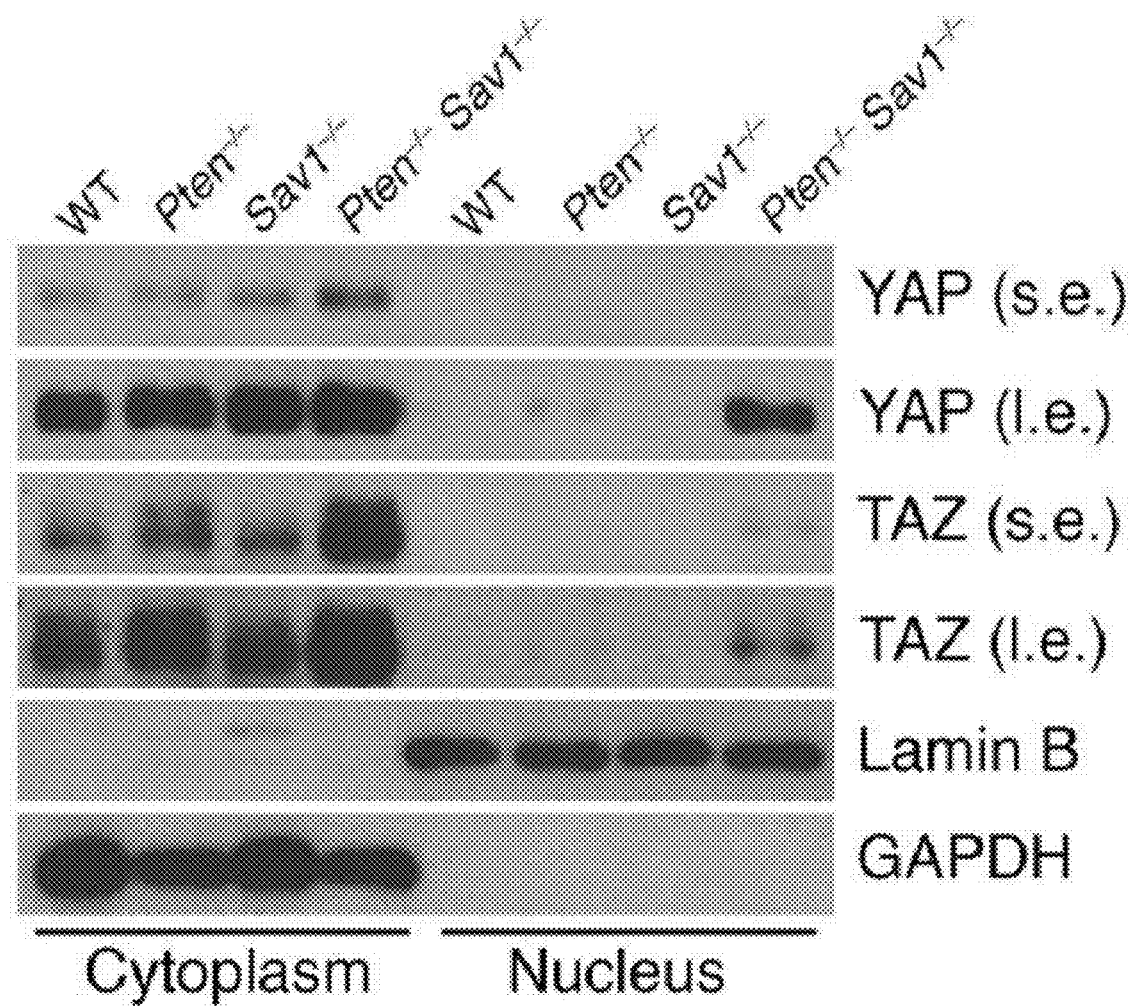

[FIG 3e]
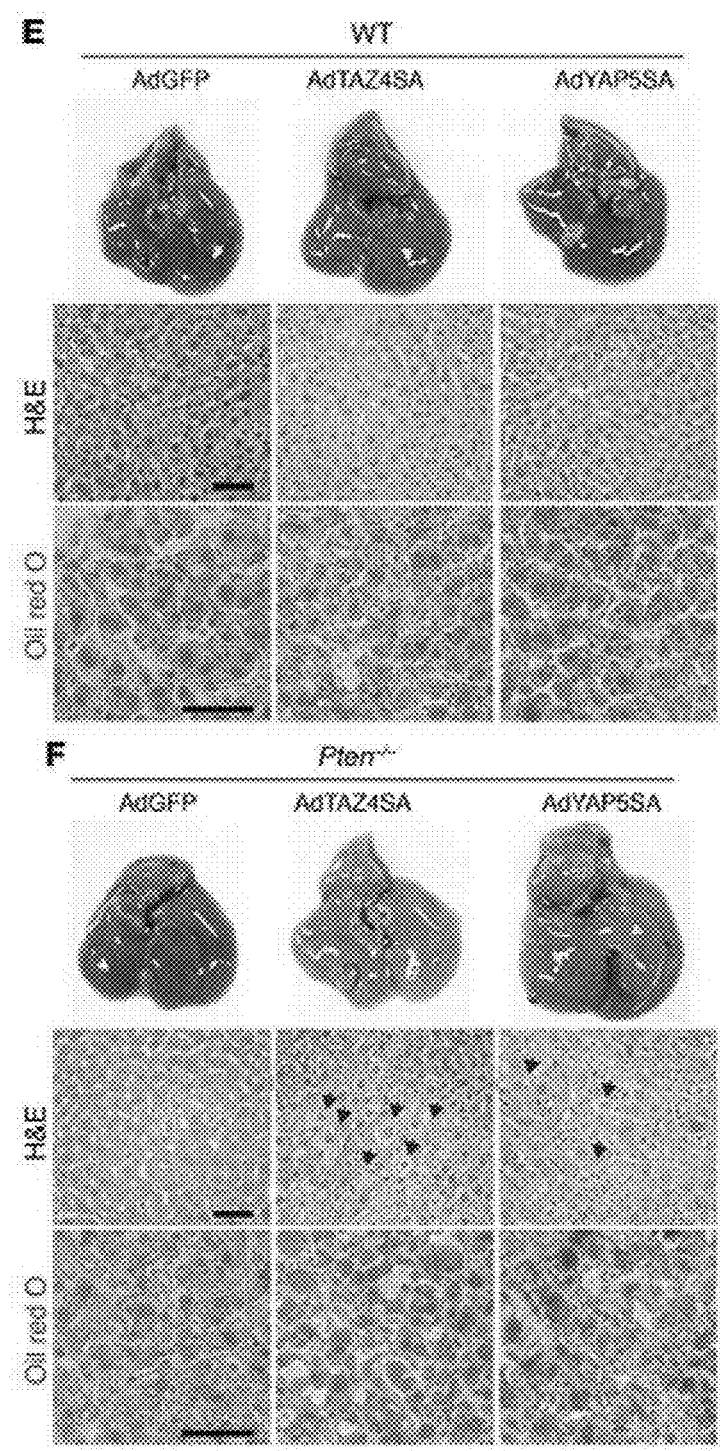

[FIG 3f]
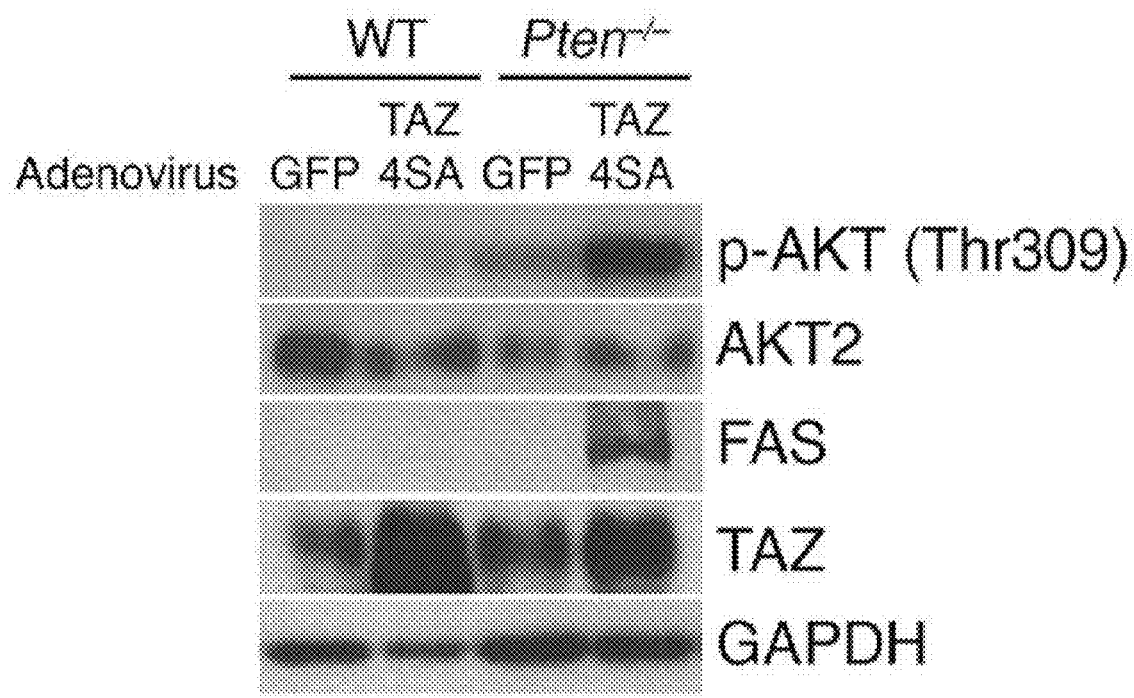

[FIG 3g]
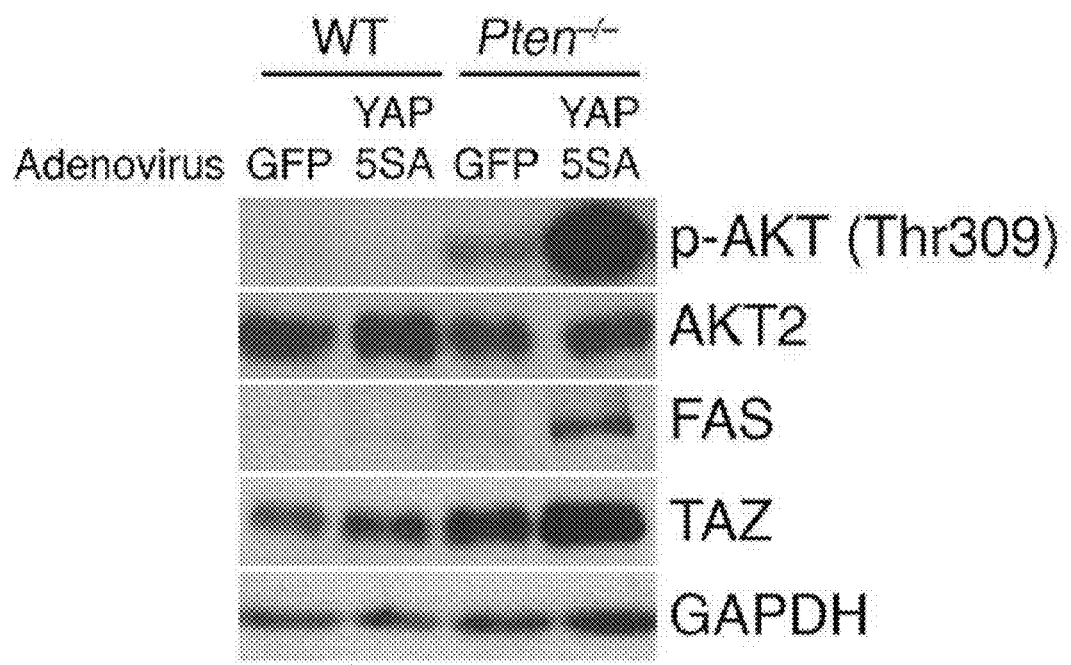

[FIG 4a]
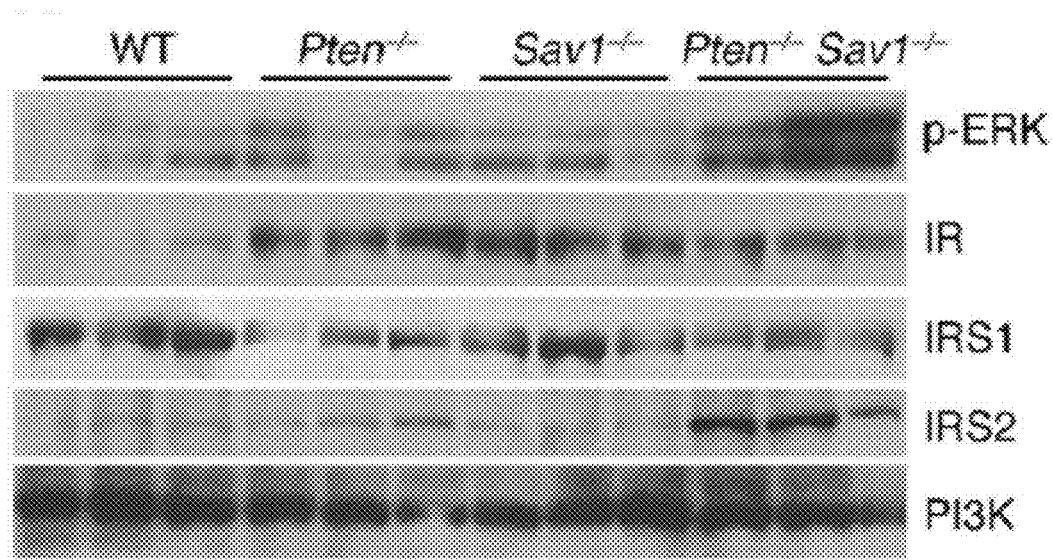

【FIG 4b】
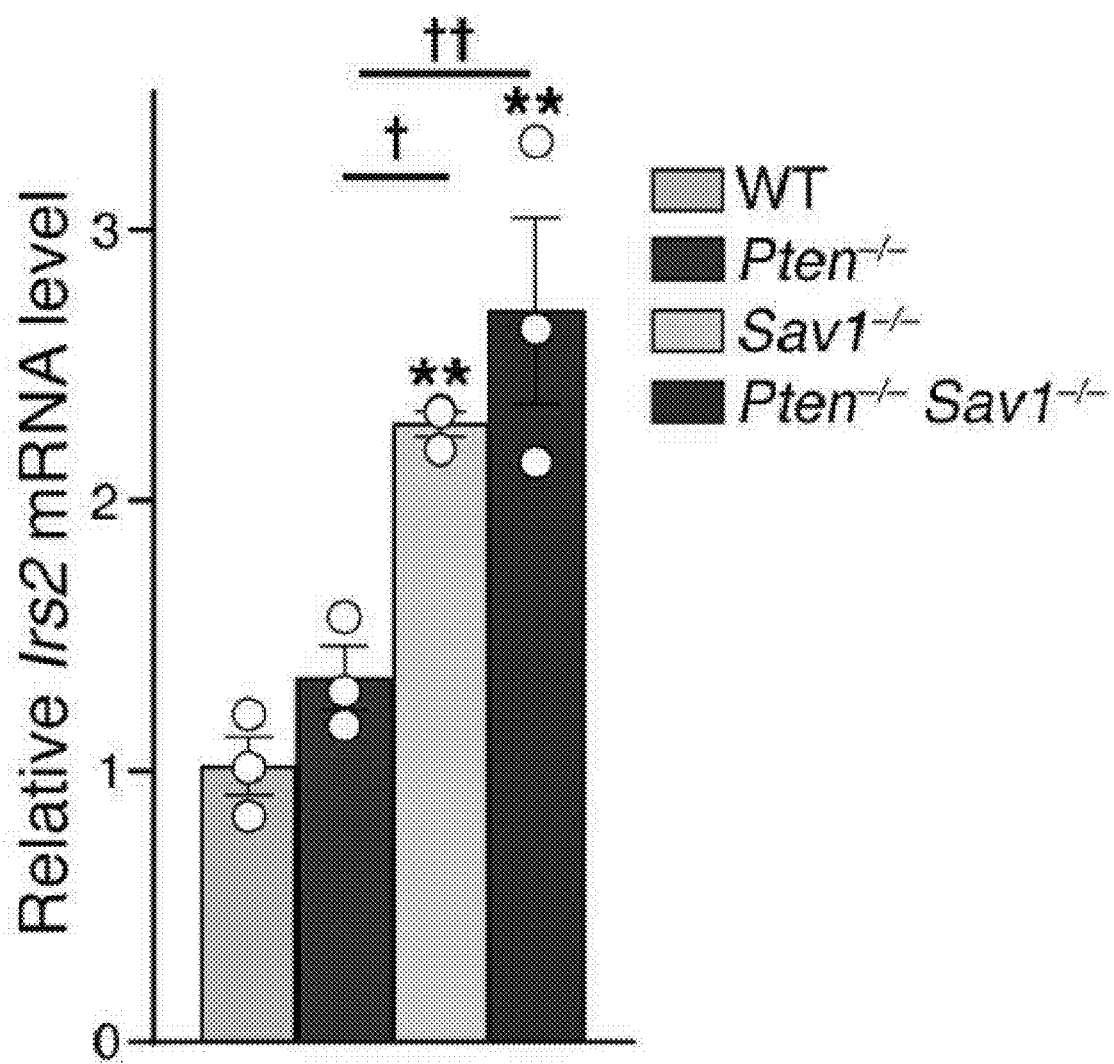

[FIG 4c]
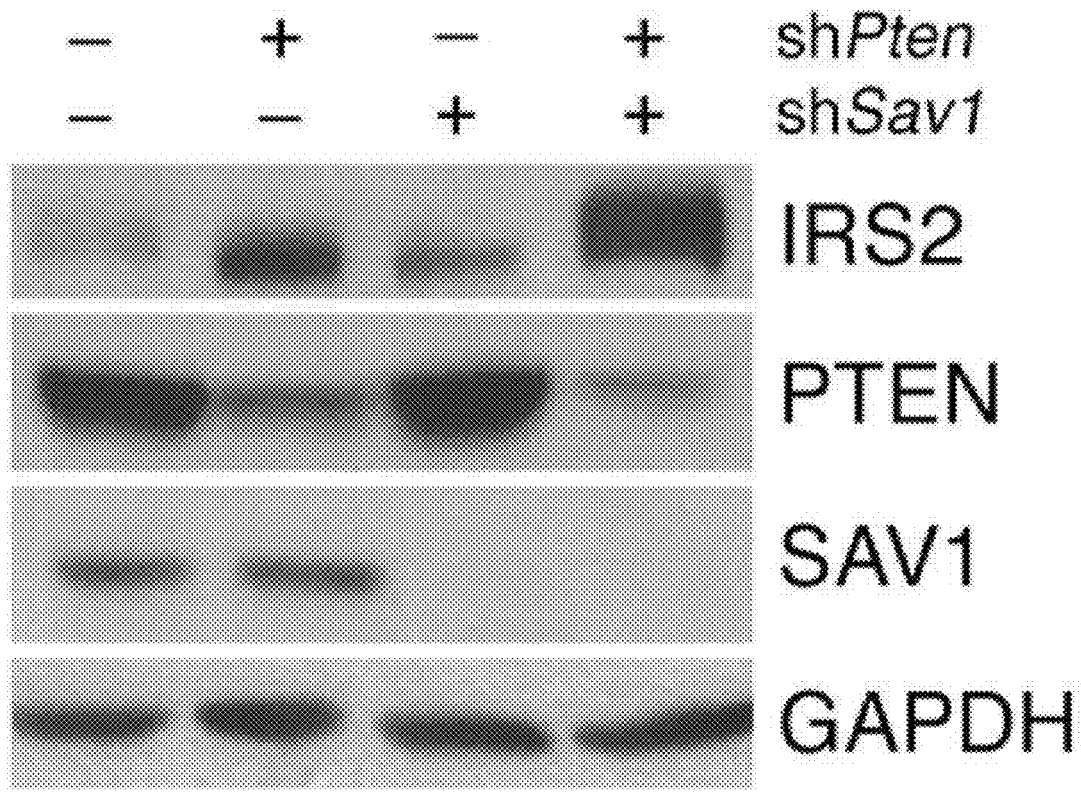

[FIG 4d]
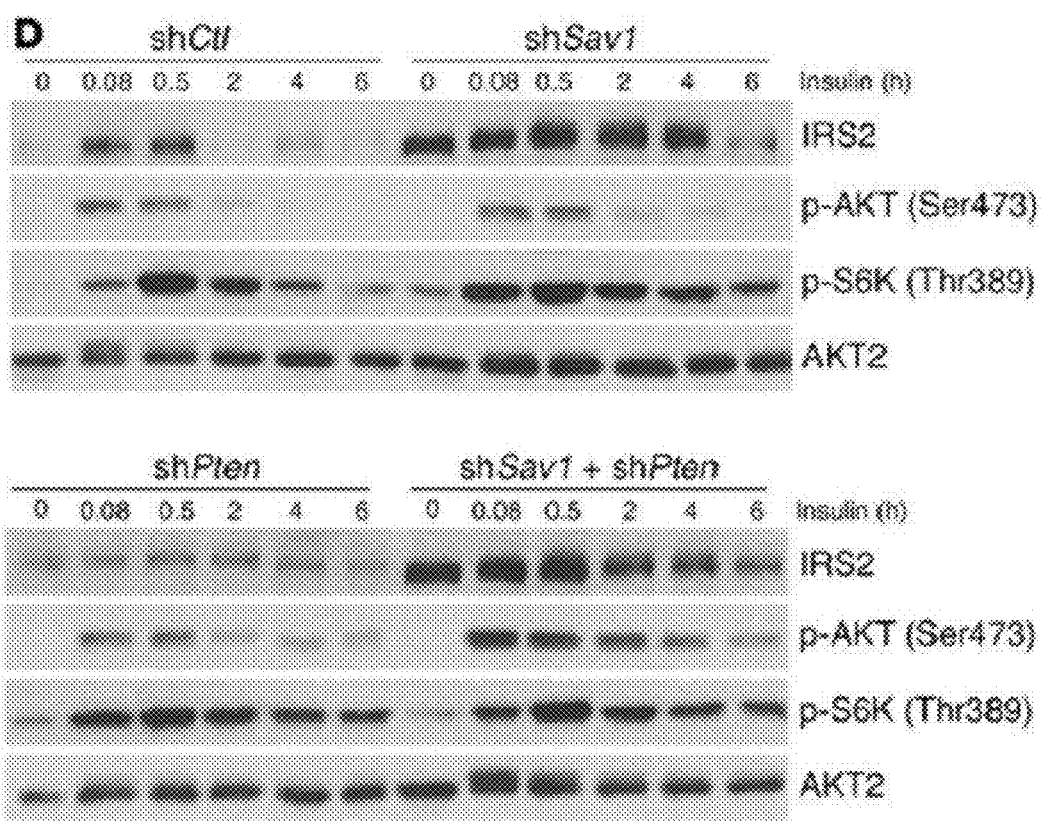

[FIG 4e]

[FIG 4f]
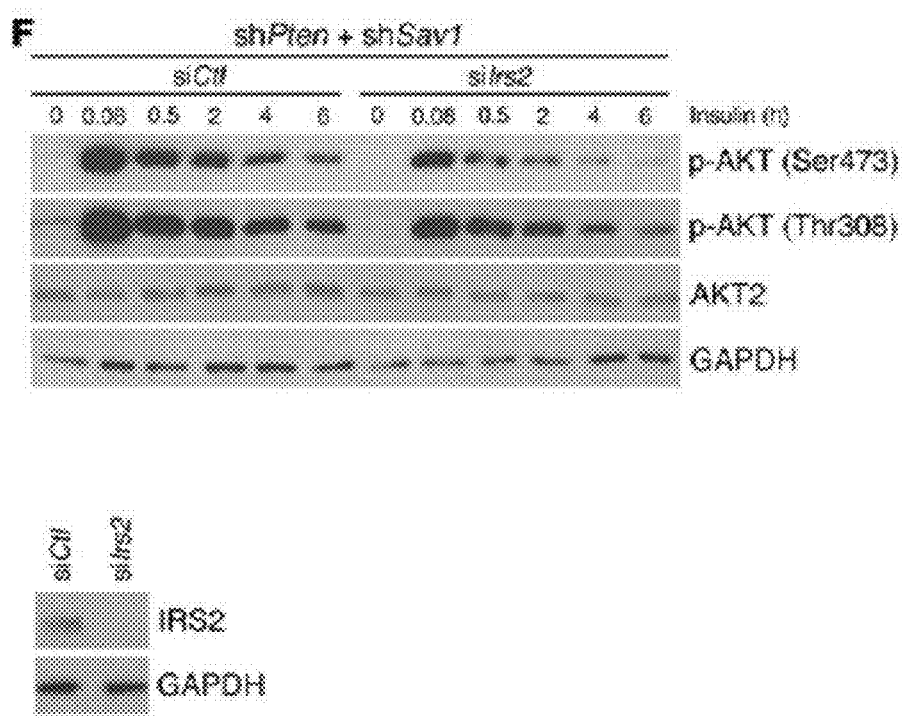

[FIG 4g]
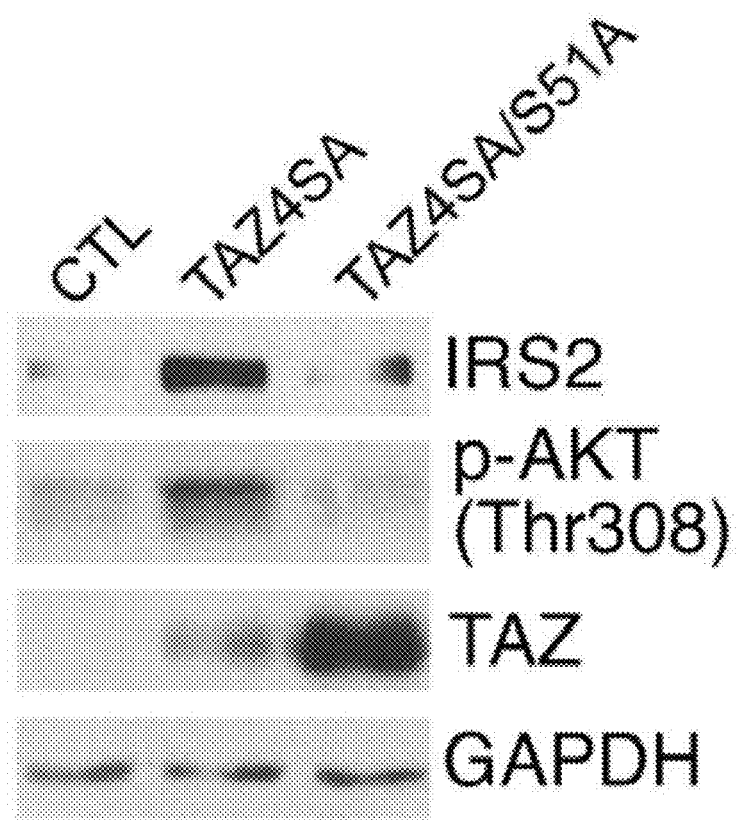

[FIG 4h]
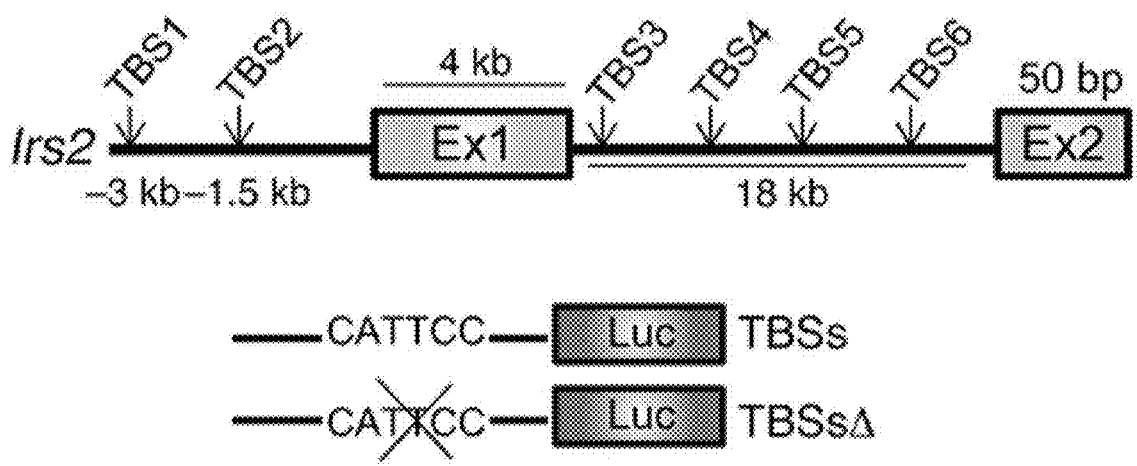

[FIG 4i]
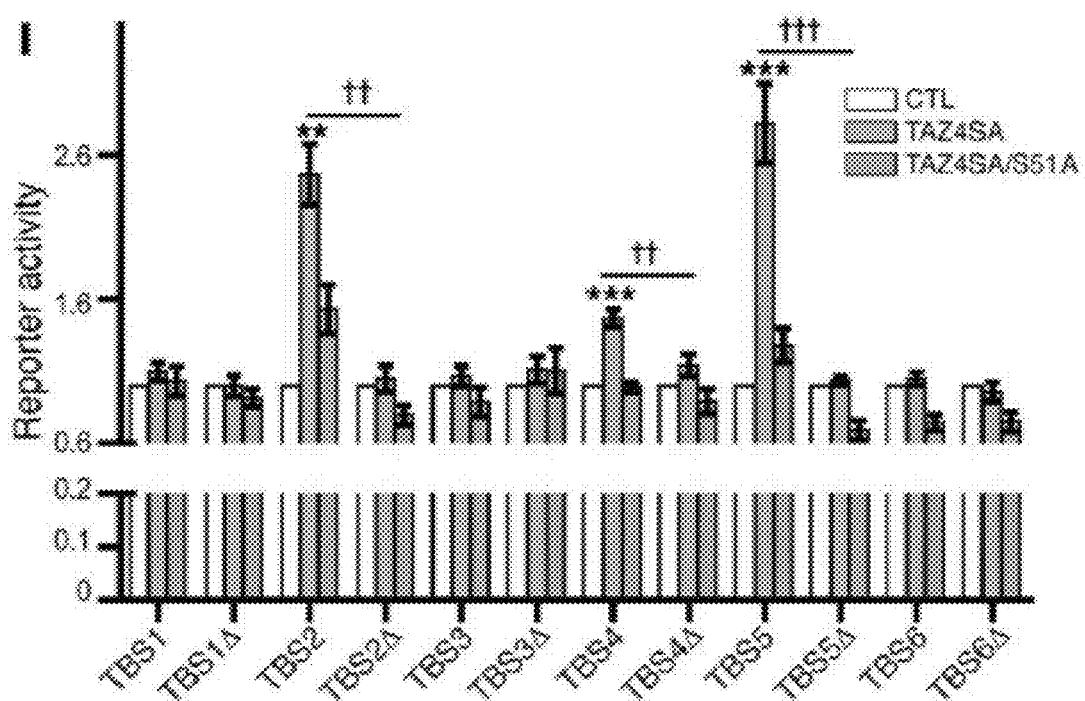

[FIG 4j]
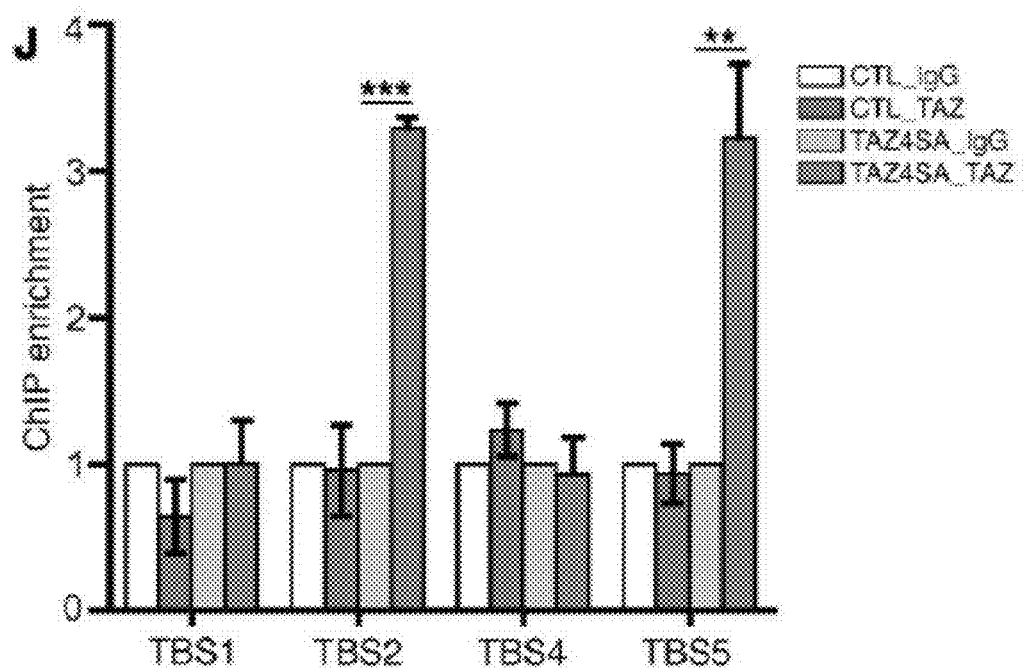

[FIG 5a]
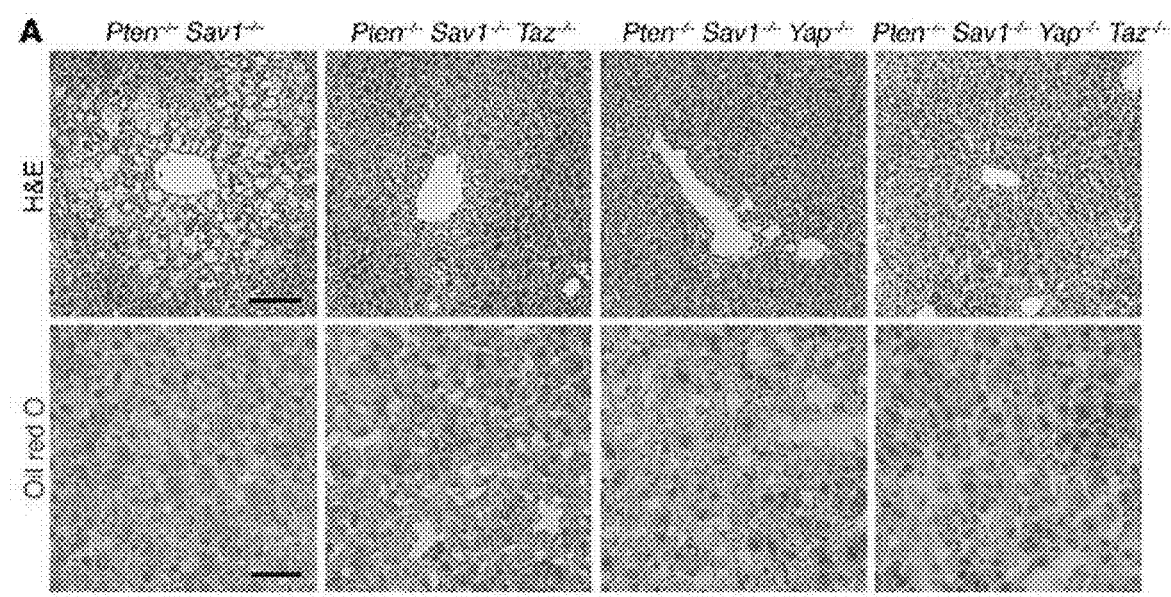

[FIG 5b]
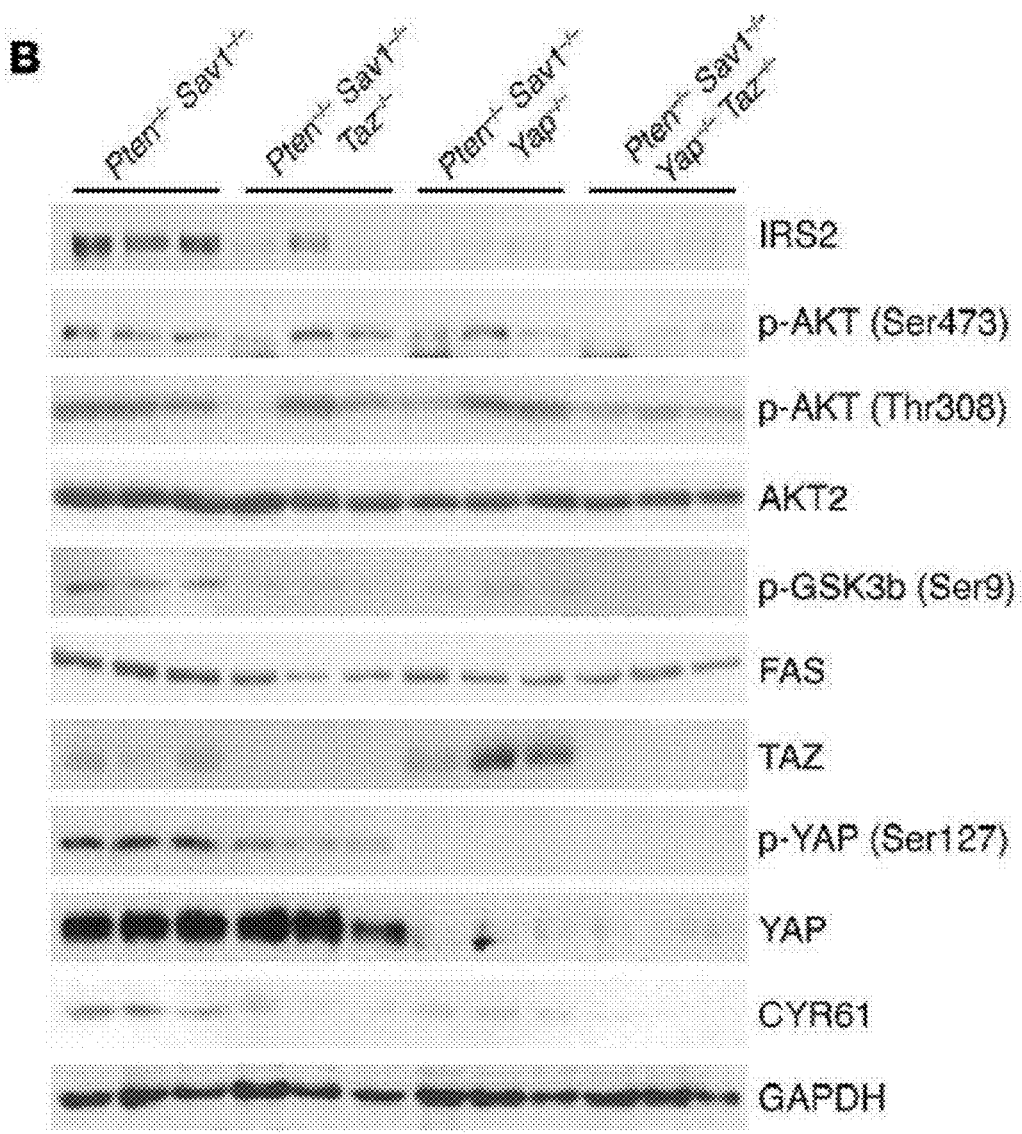

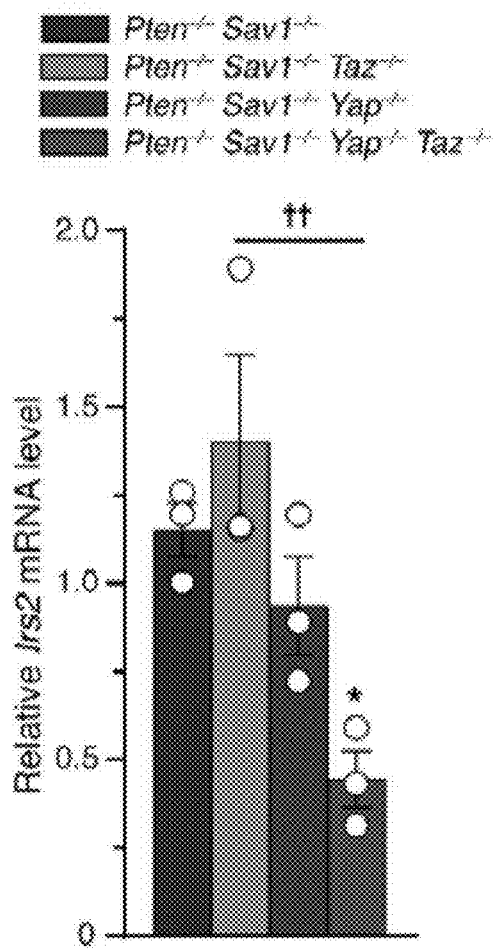

[FIG 6a]
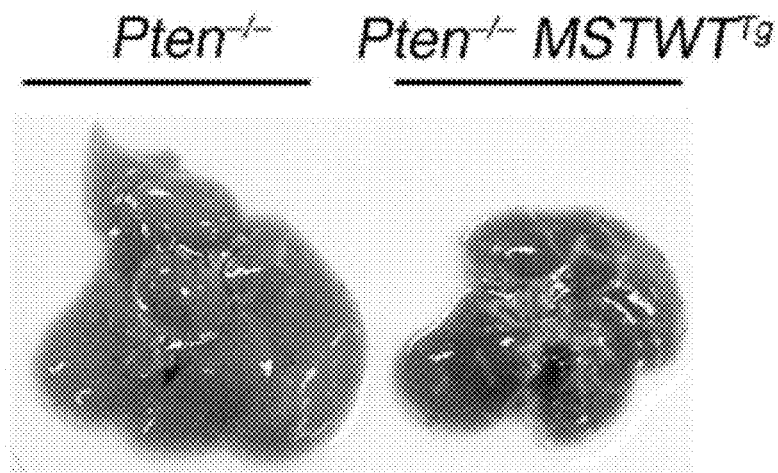

[FIG 6b]
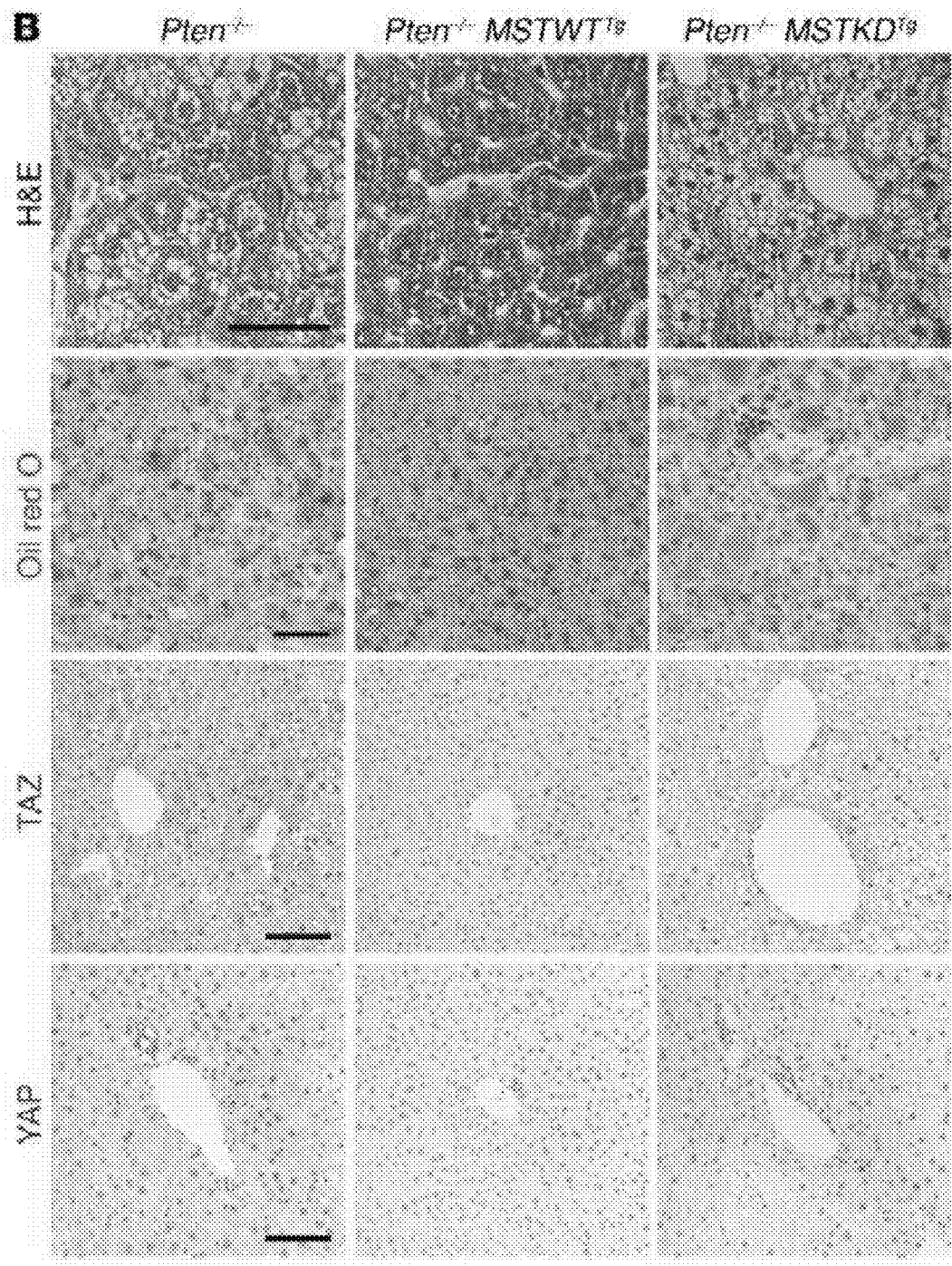

[FIG 6c]
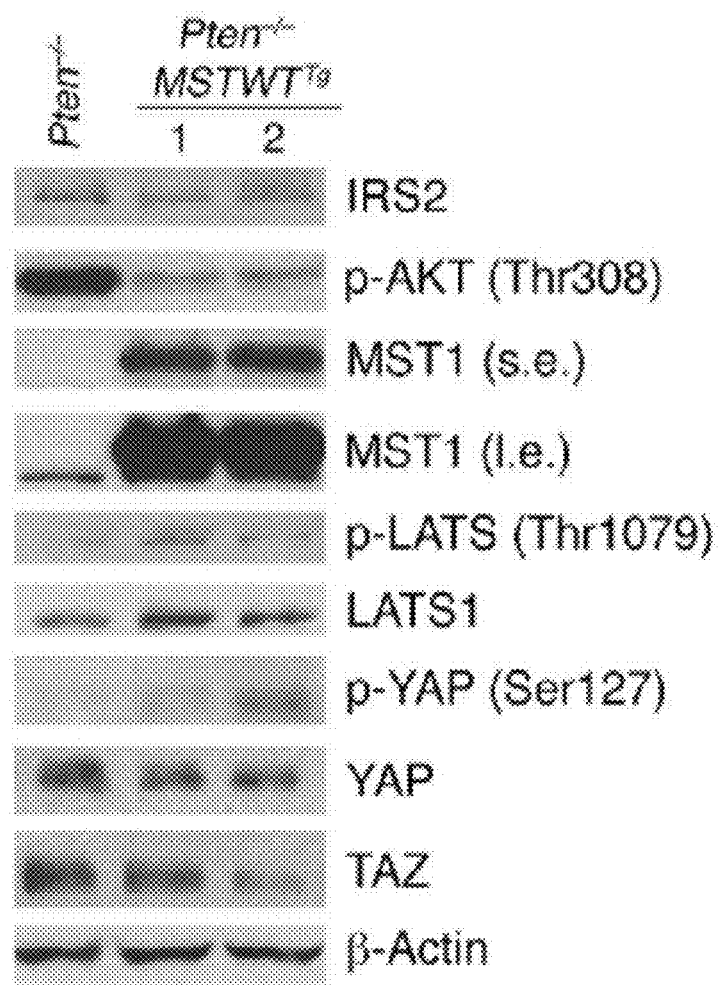

[FIG 7a]
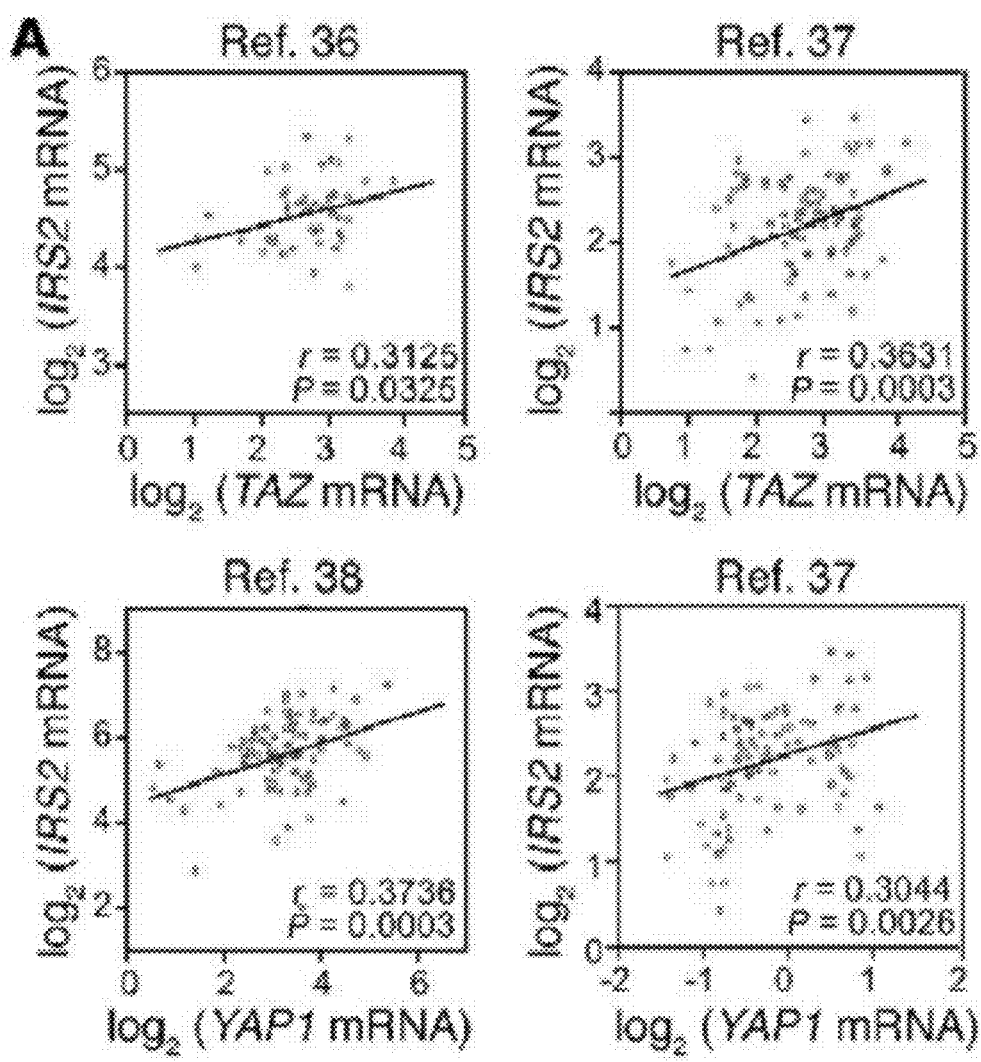

[FIG 7b]
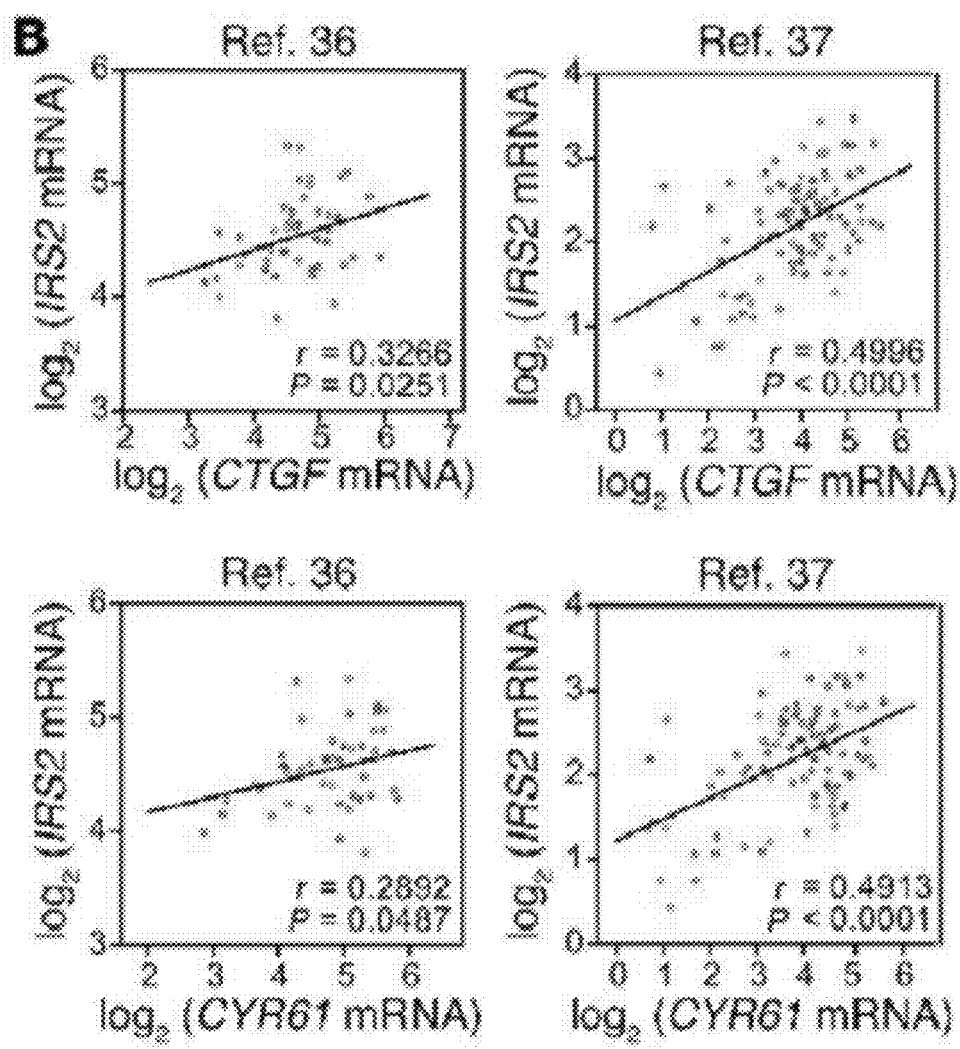

[FIG 7c]
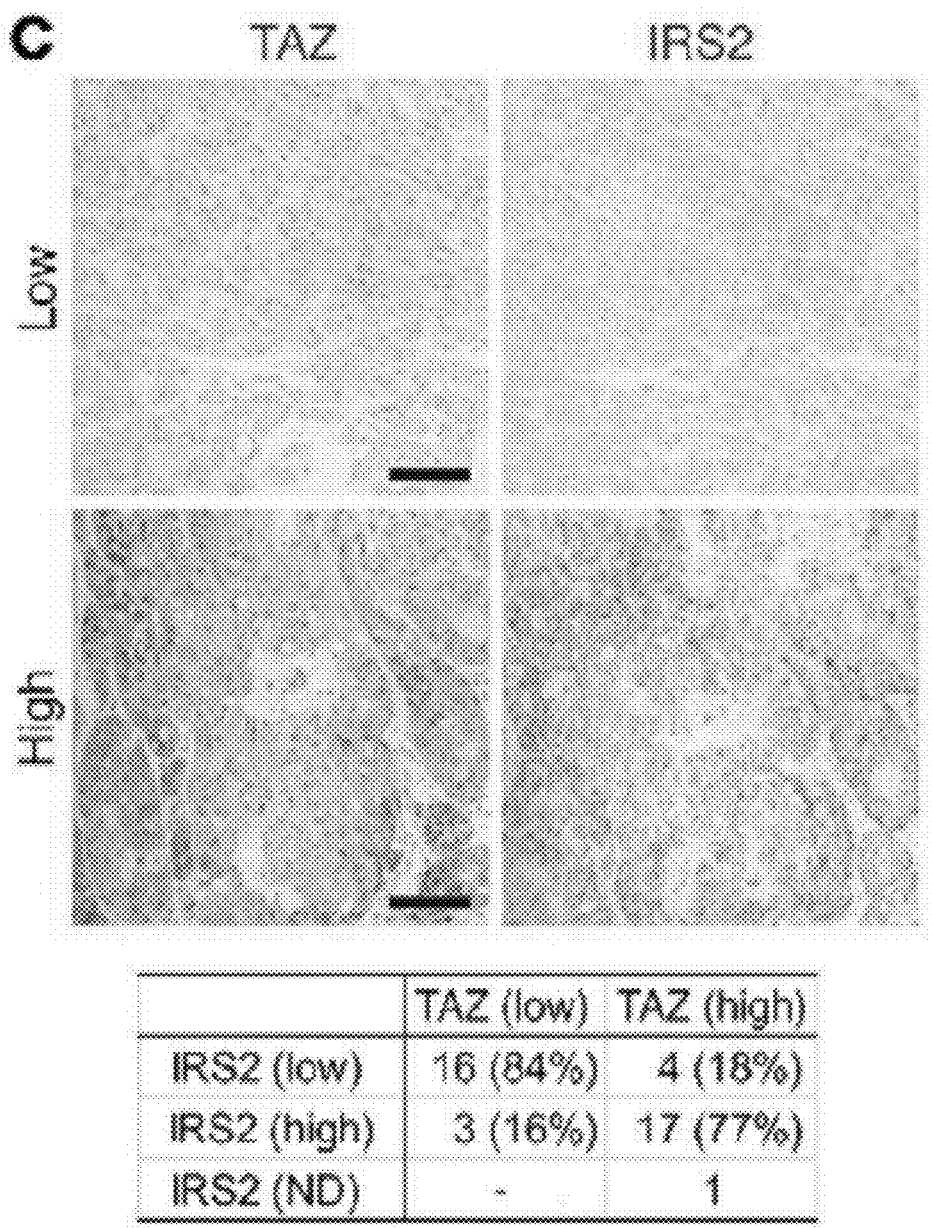

[FIG 7d]
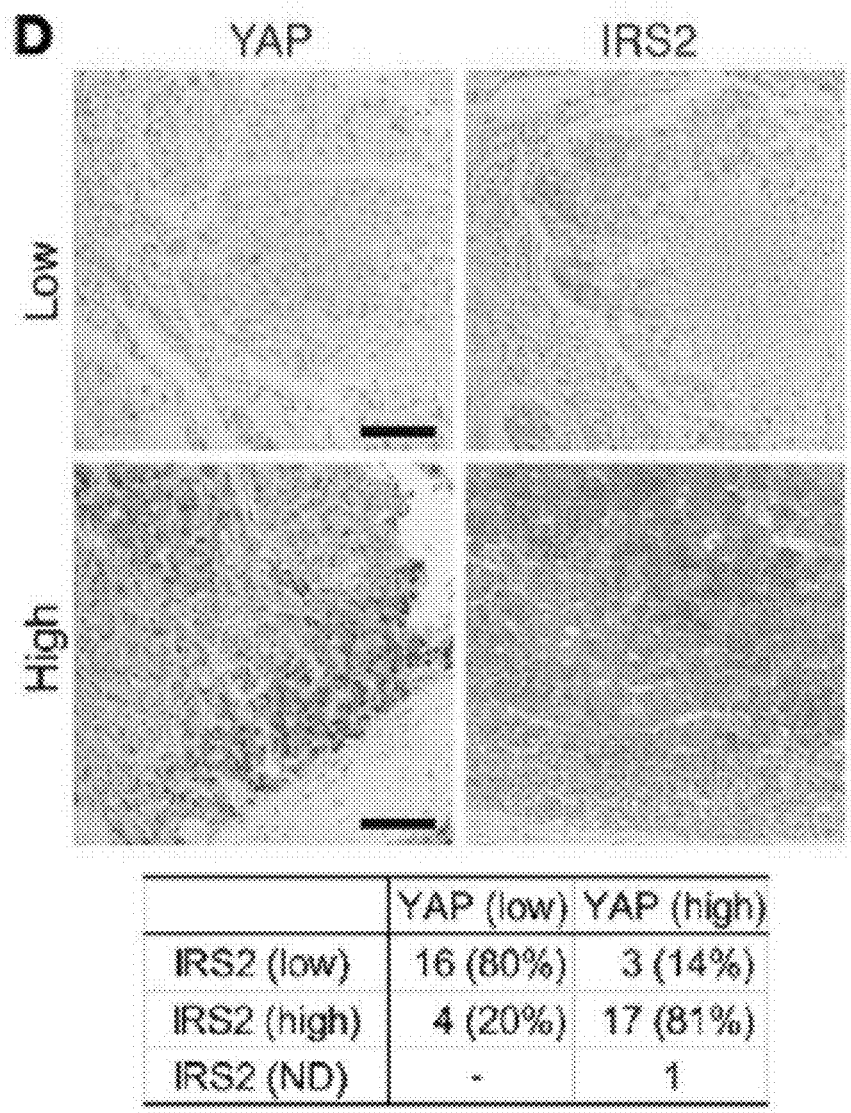

[FIG 7e]
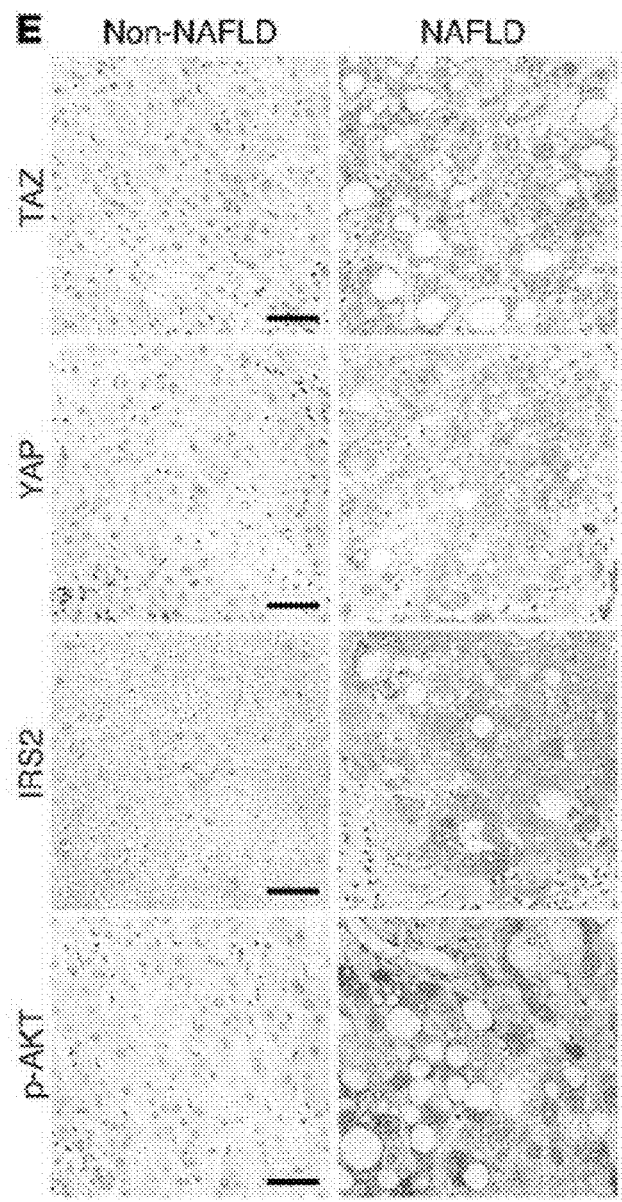

[FIG 7f]
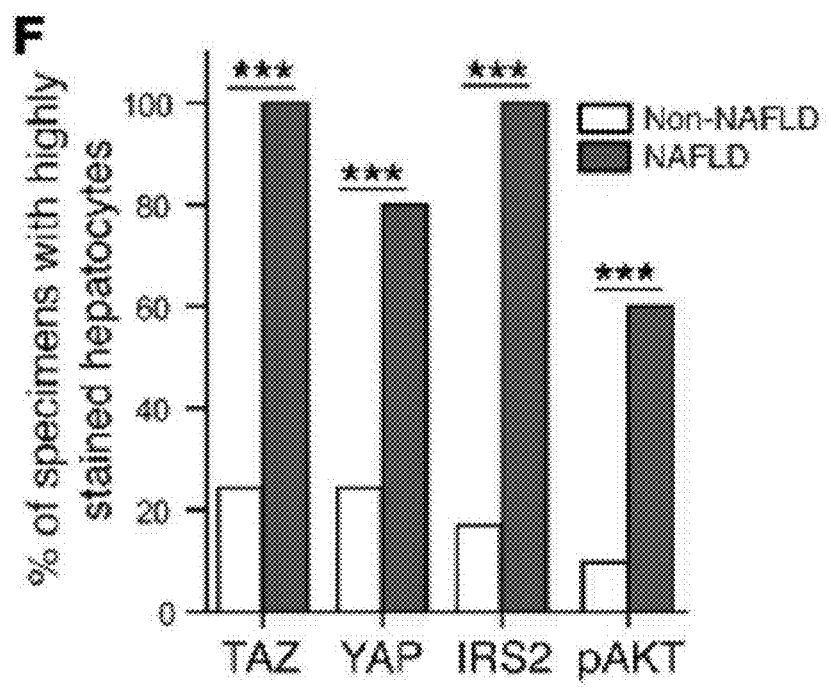

[FIG 8a]
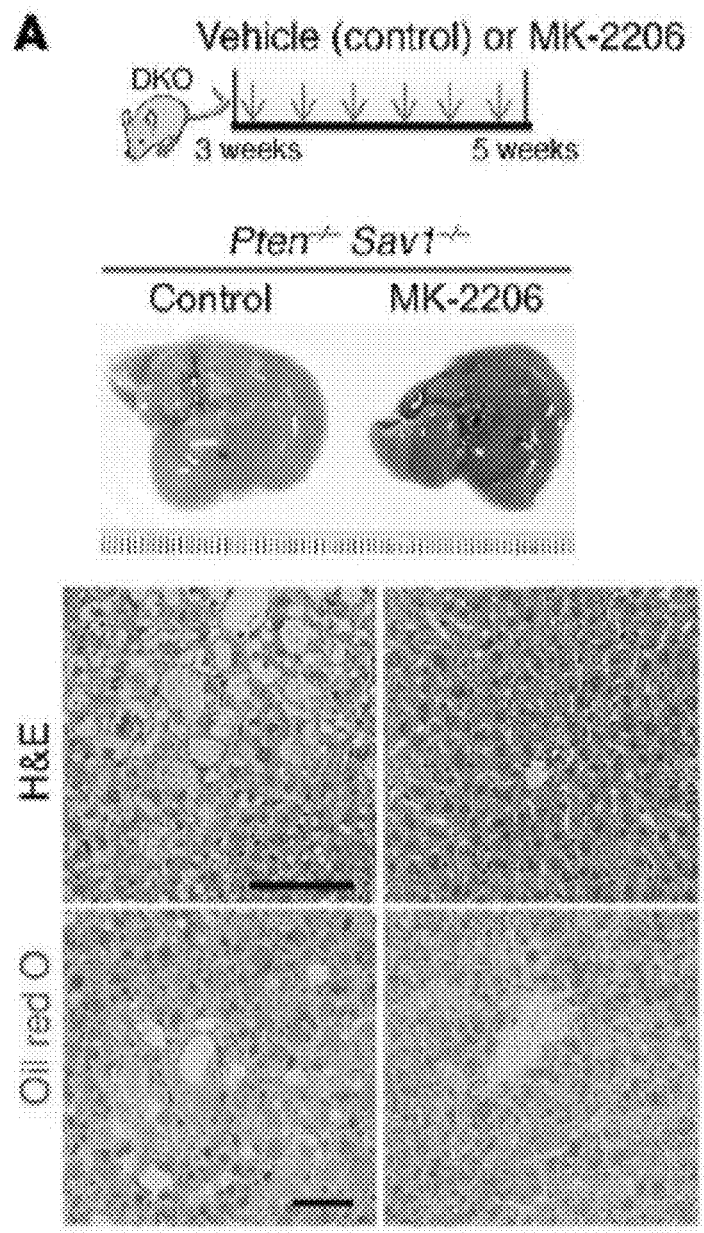

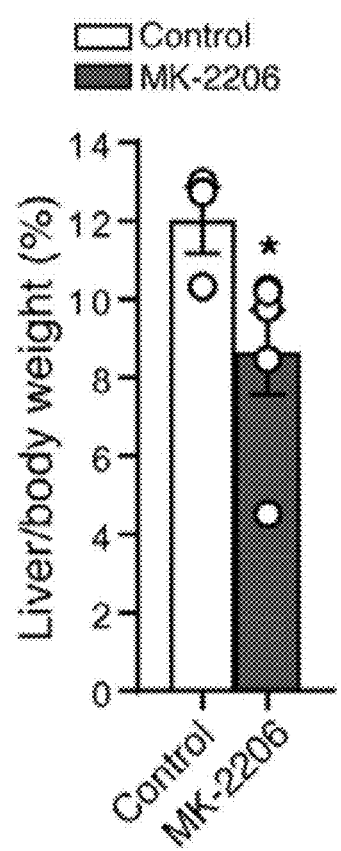
[FIG 8b]

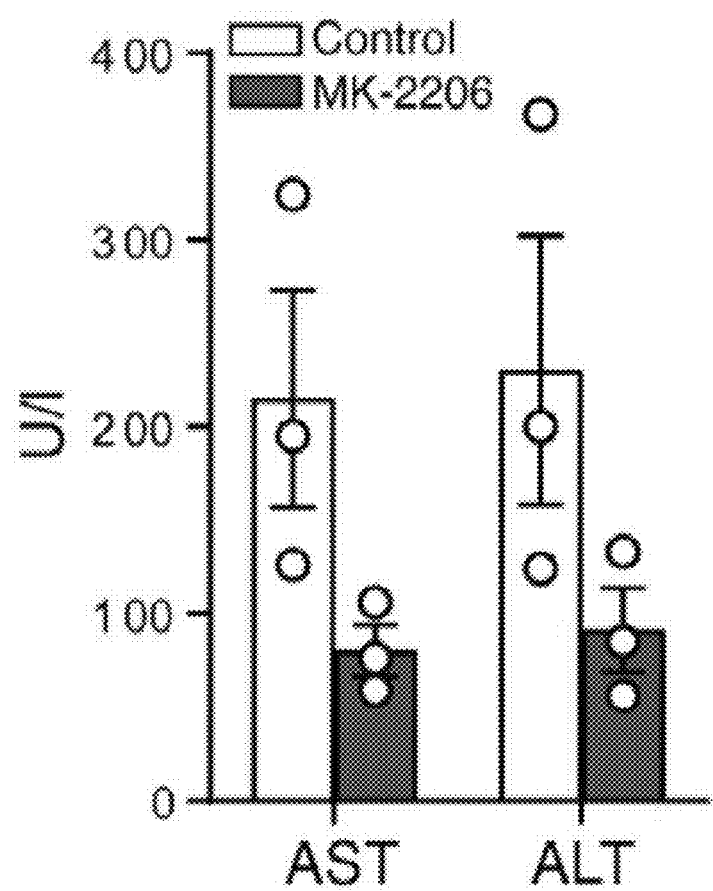
[FIG 8c]

[FIG 8d]
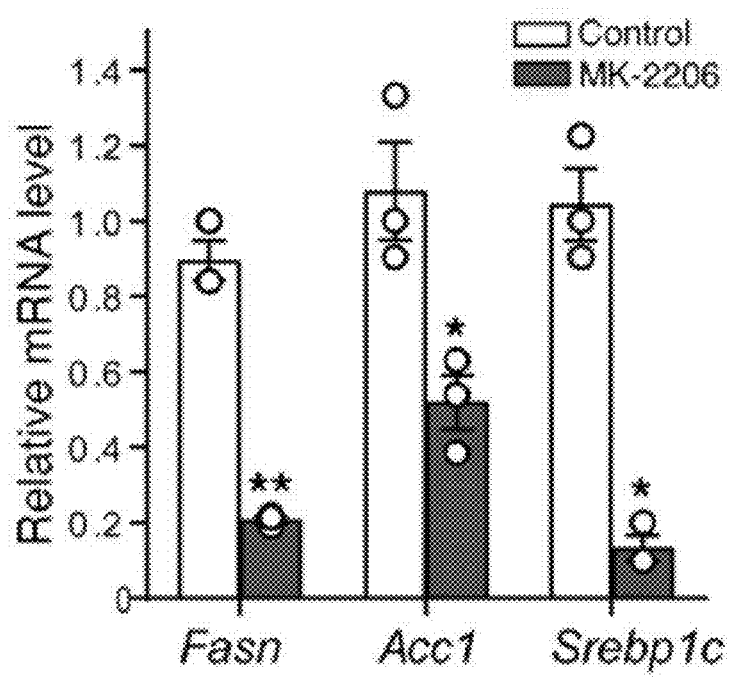

[FIG 8e]
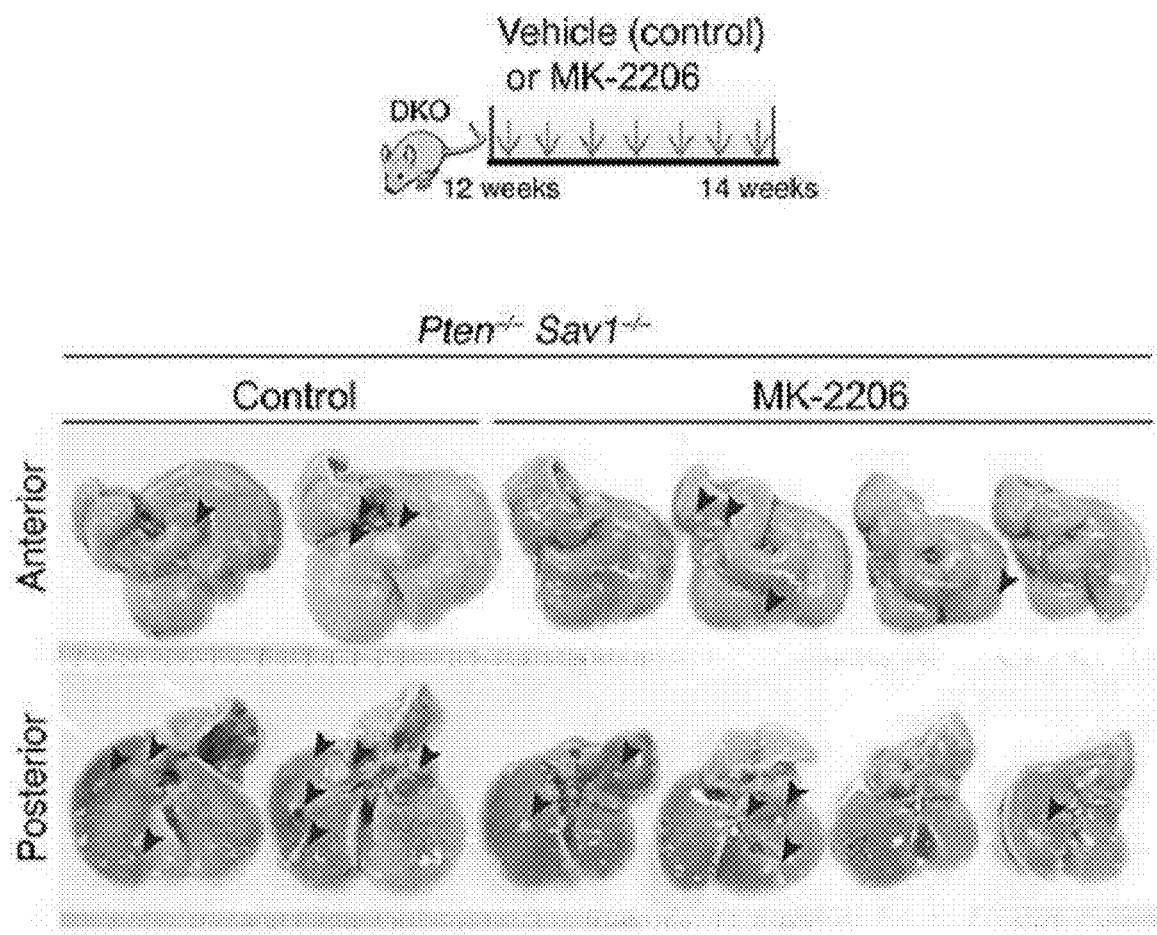

[FIG 8f]
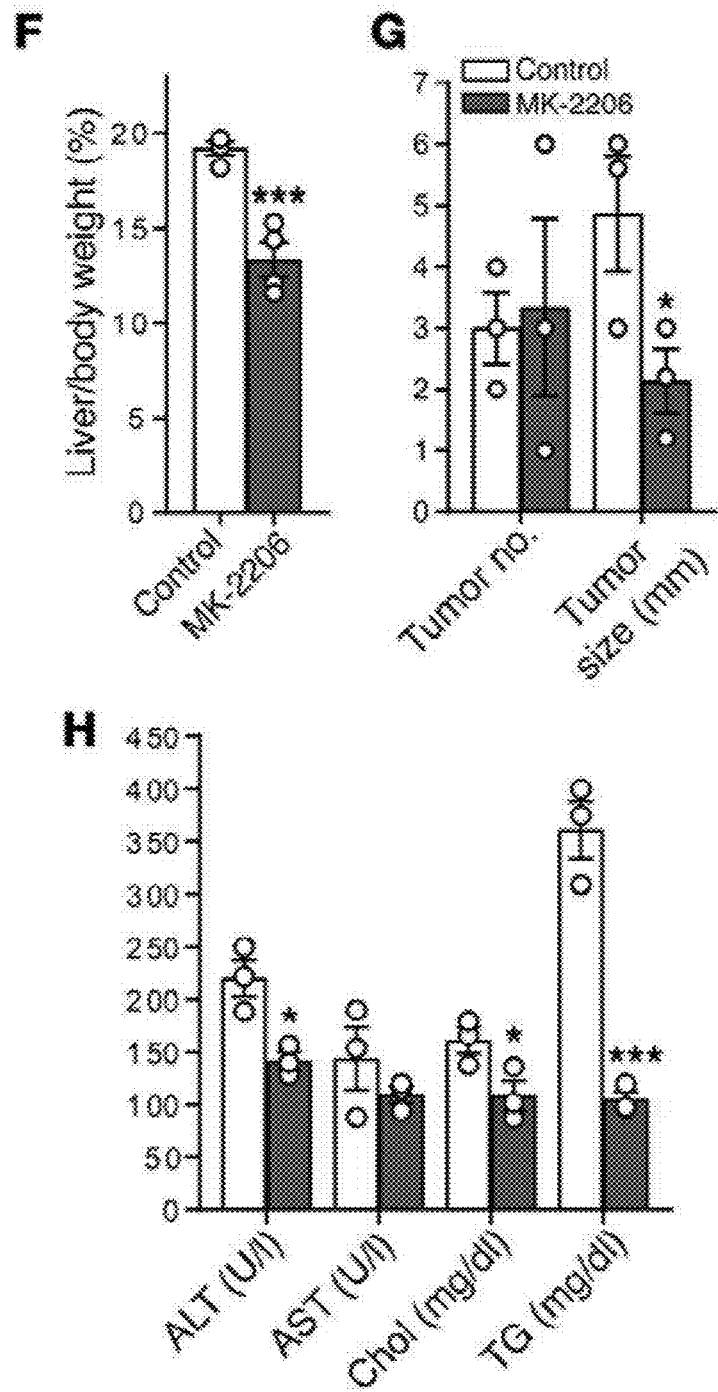

[FIG 8g]
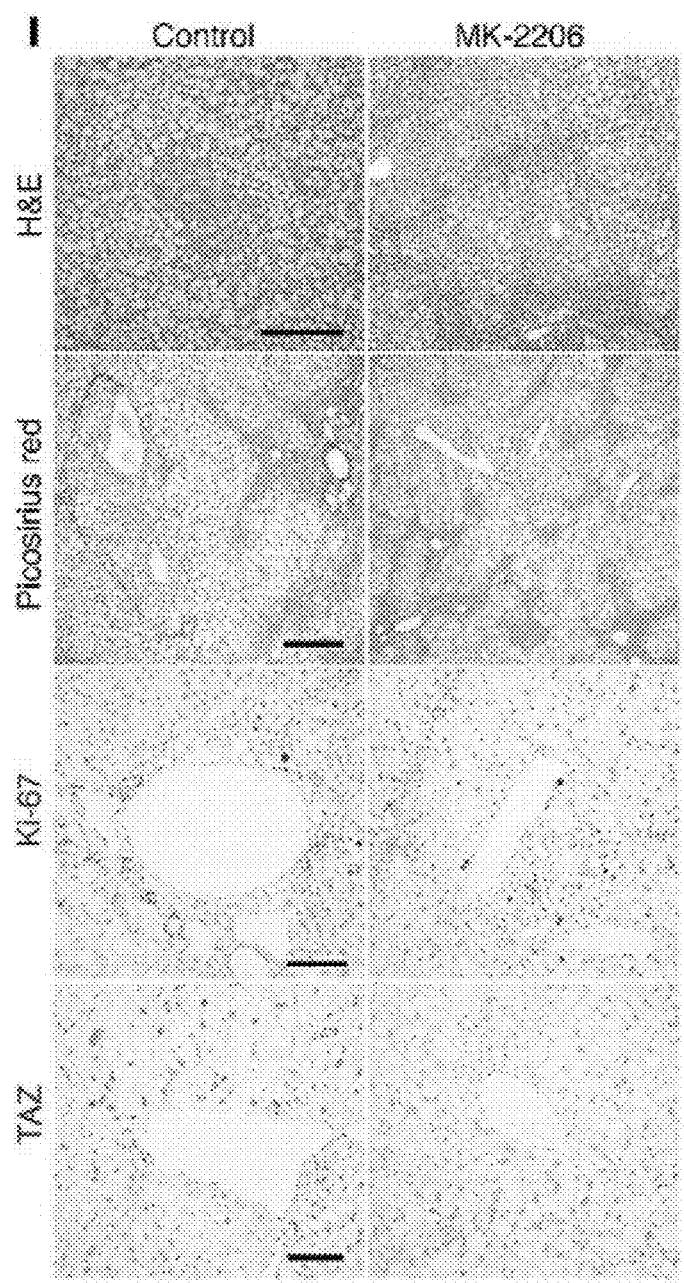

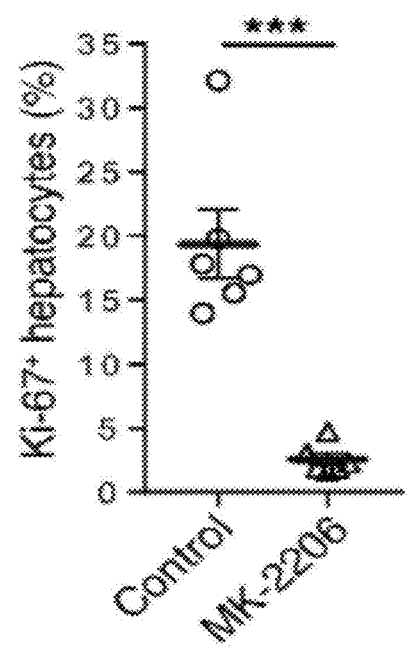
[FIG 8h]

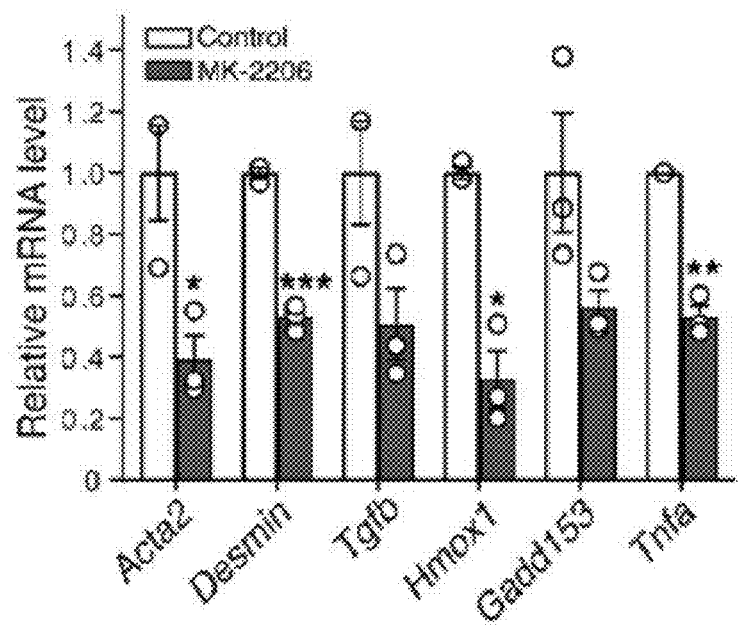
[FIG 8i]

[FIG 9a]
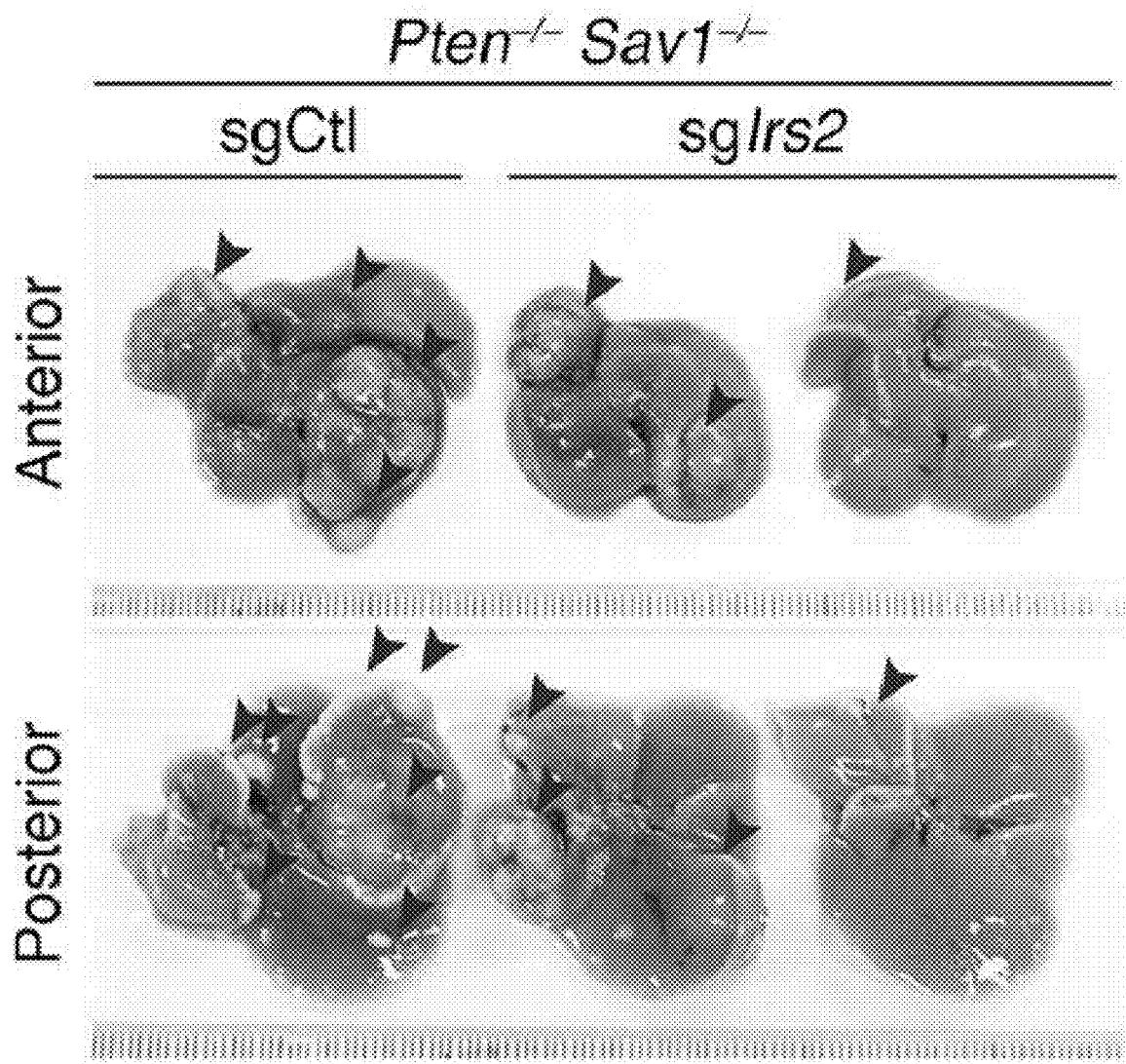

[FIG 9b]
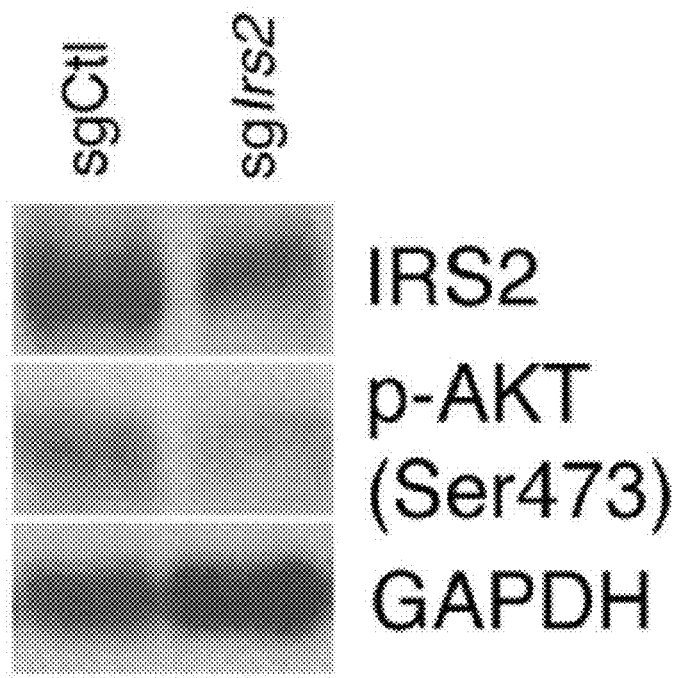

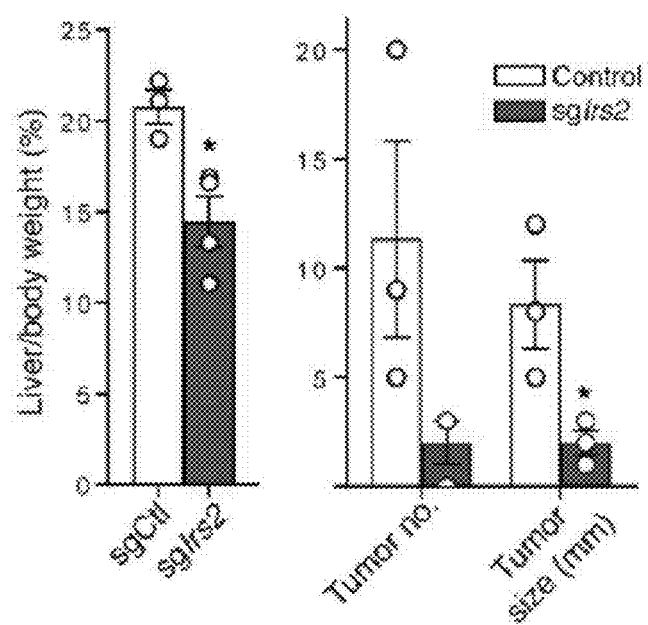
[FIG 9c]

[FIG 9d]
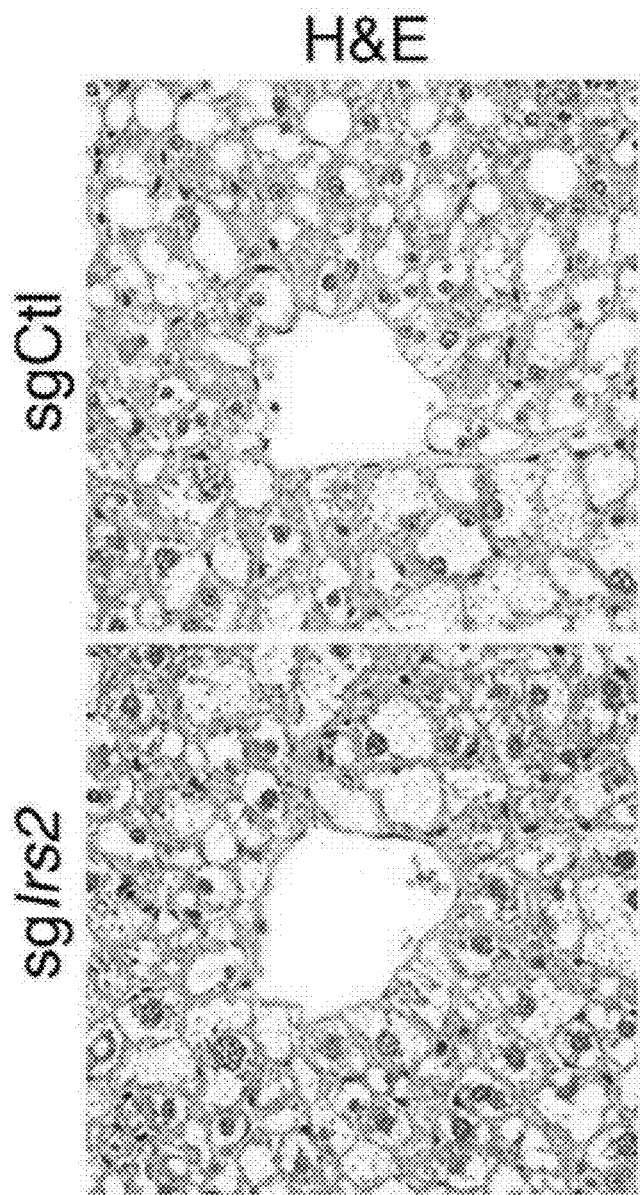

[FIG 10]
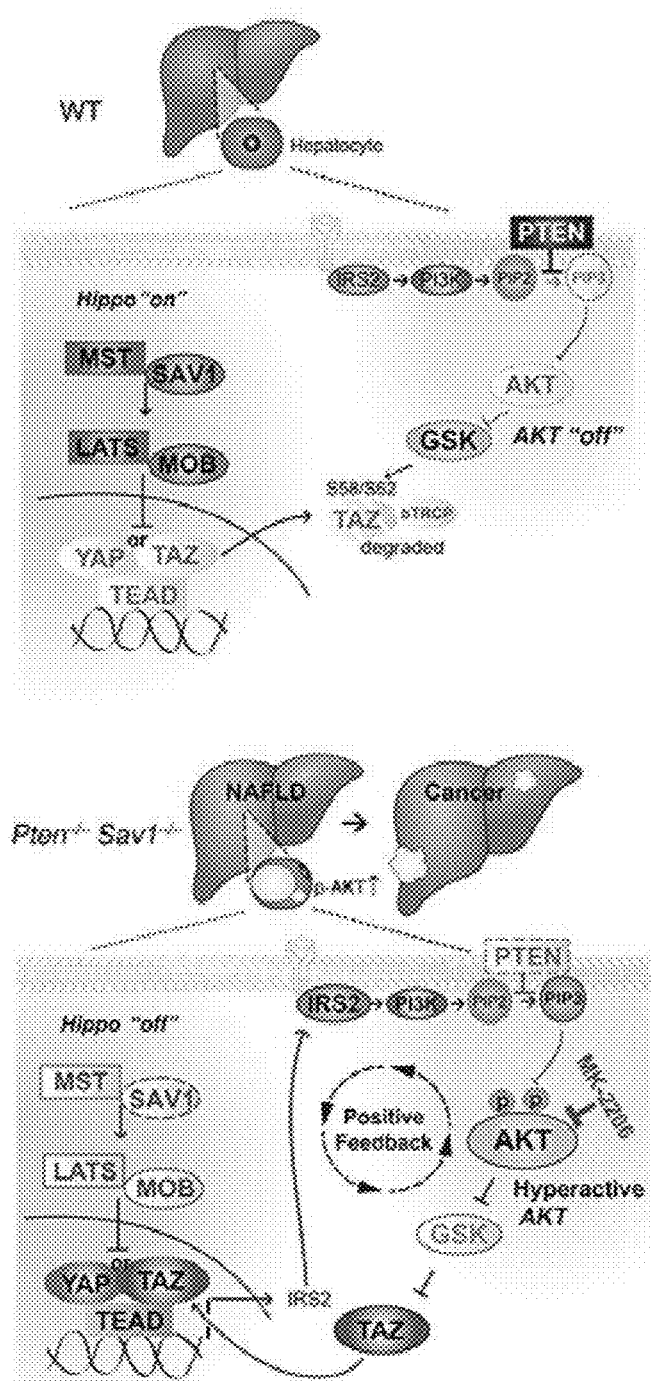

[FIG 11]
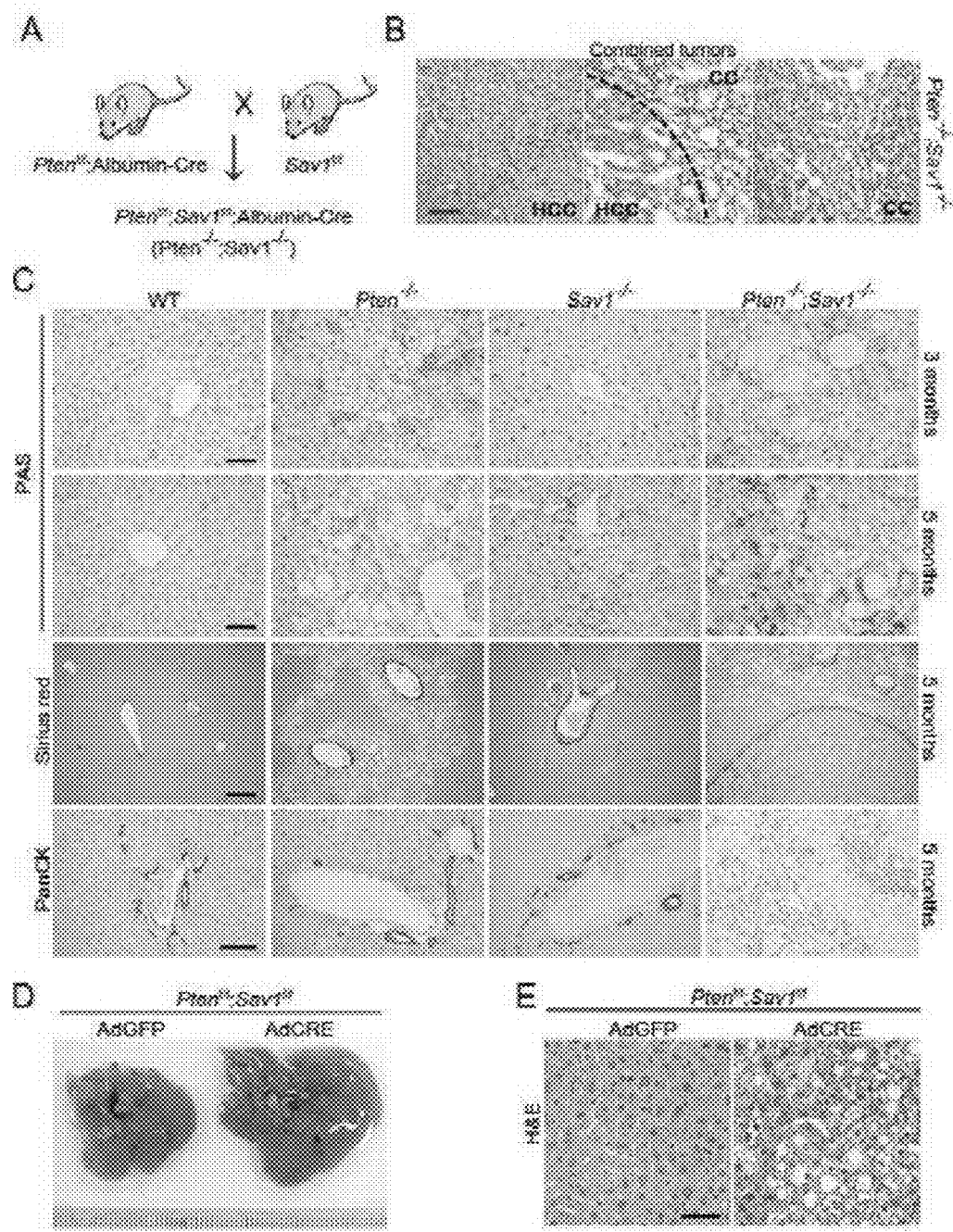

[FIG 12]
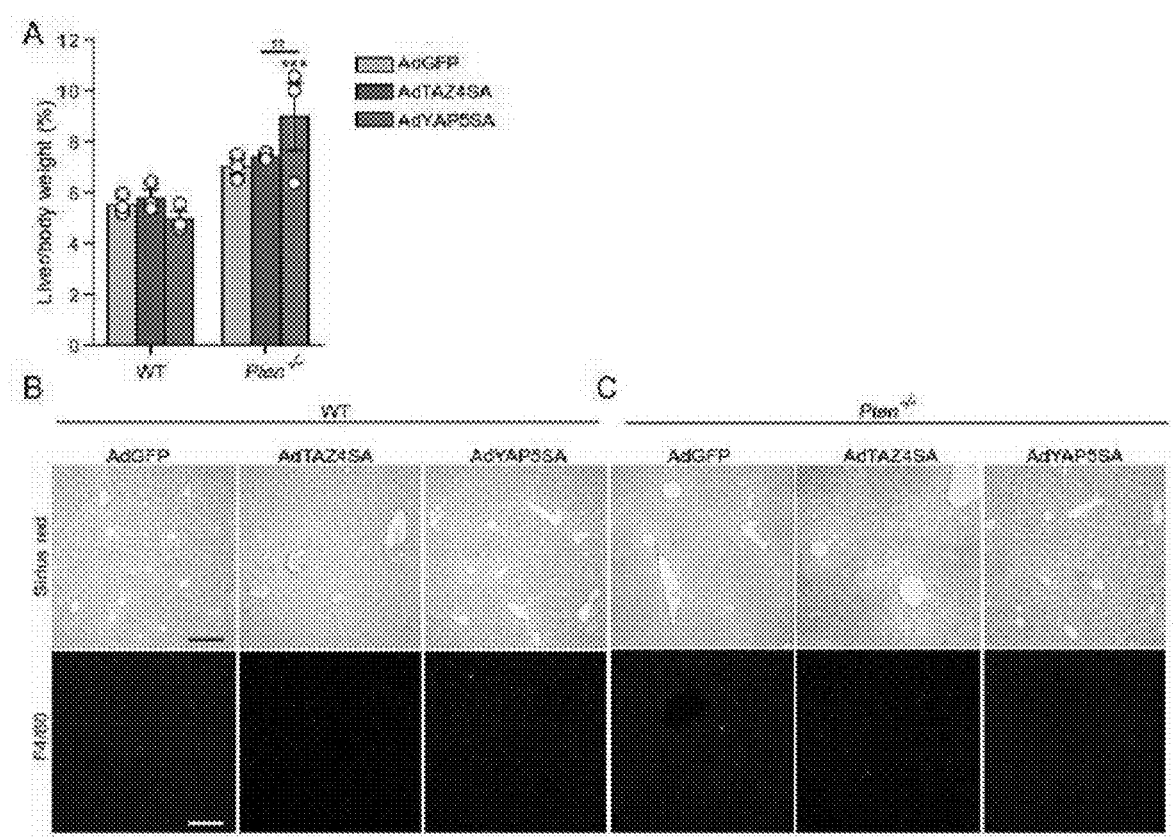

[FIG 13]
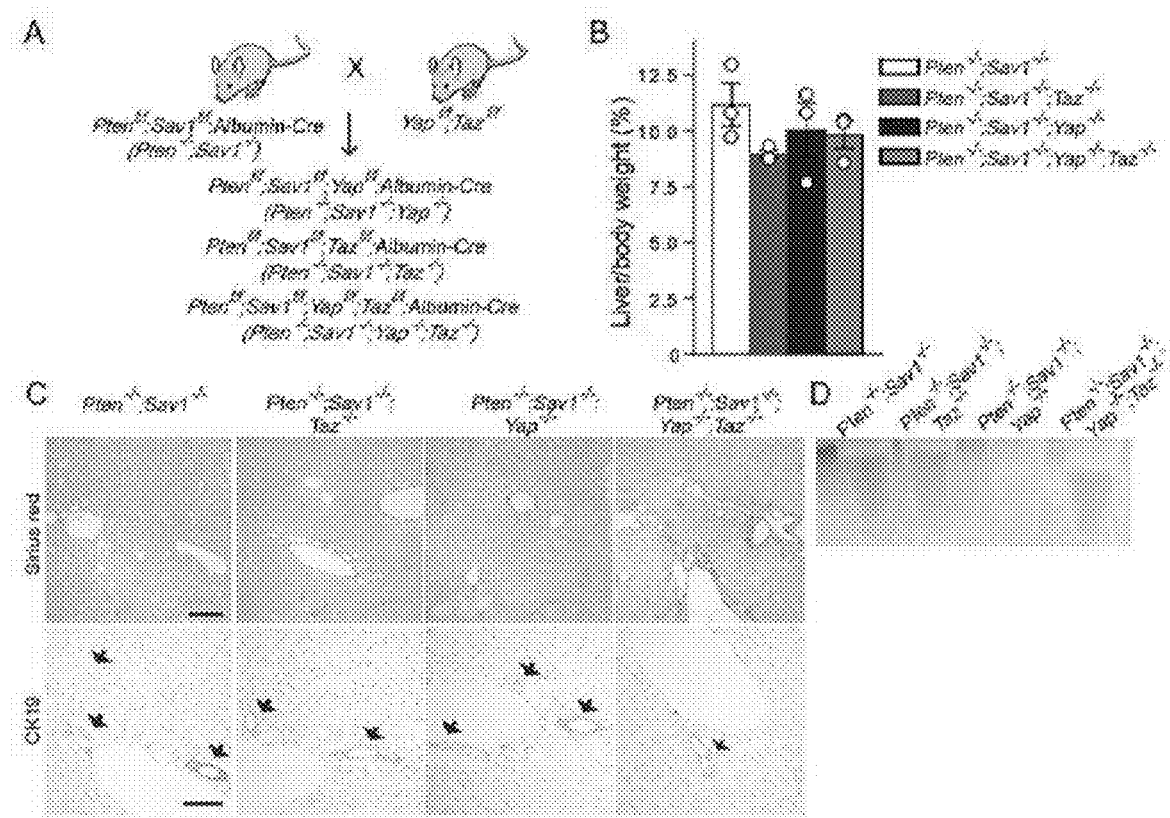

[FIG 14]
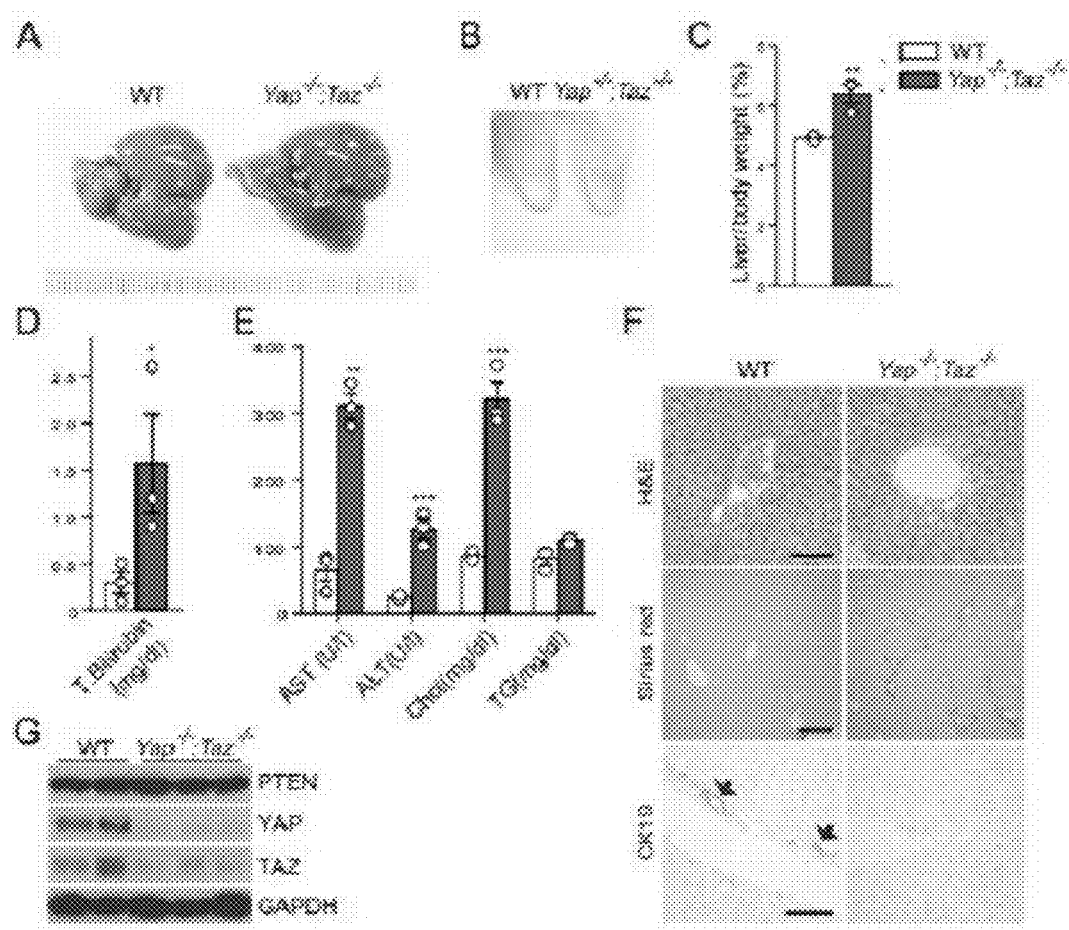

[FIG 15]
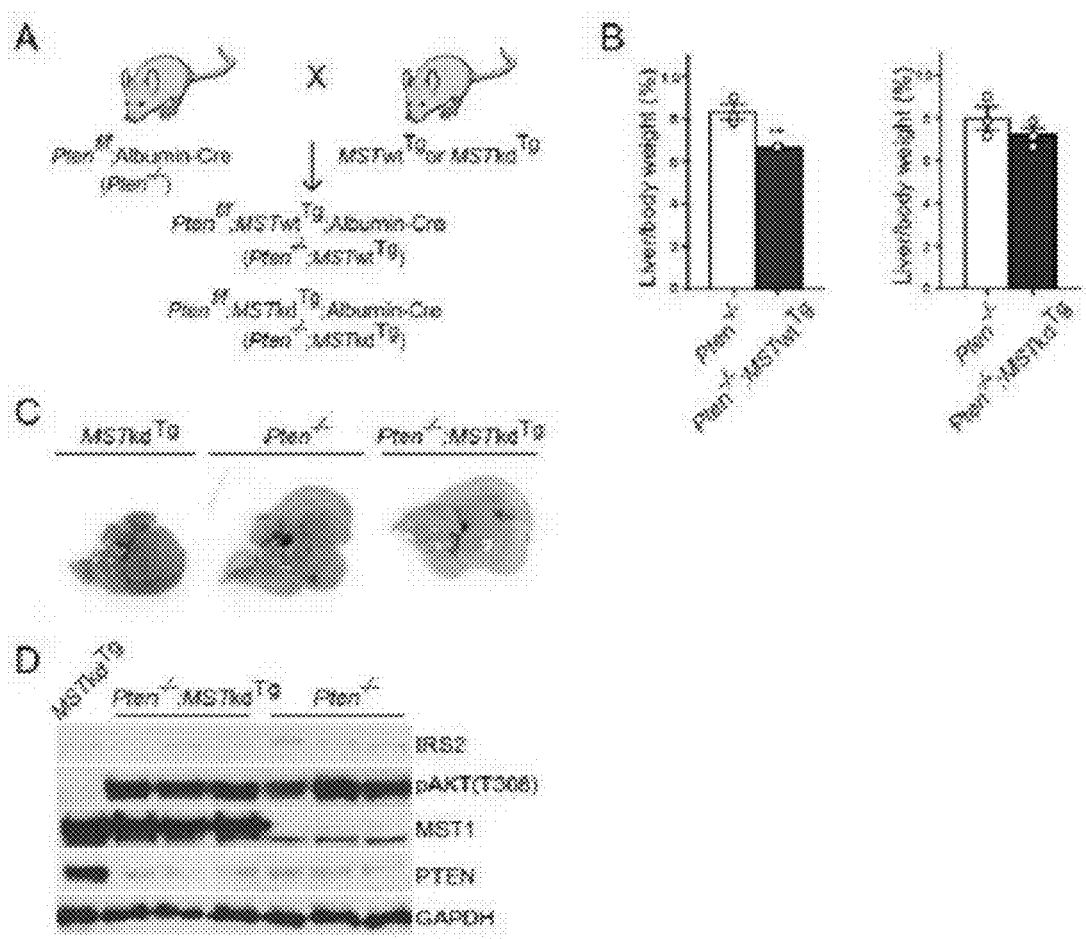

[FIG 16]
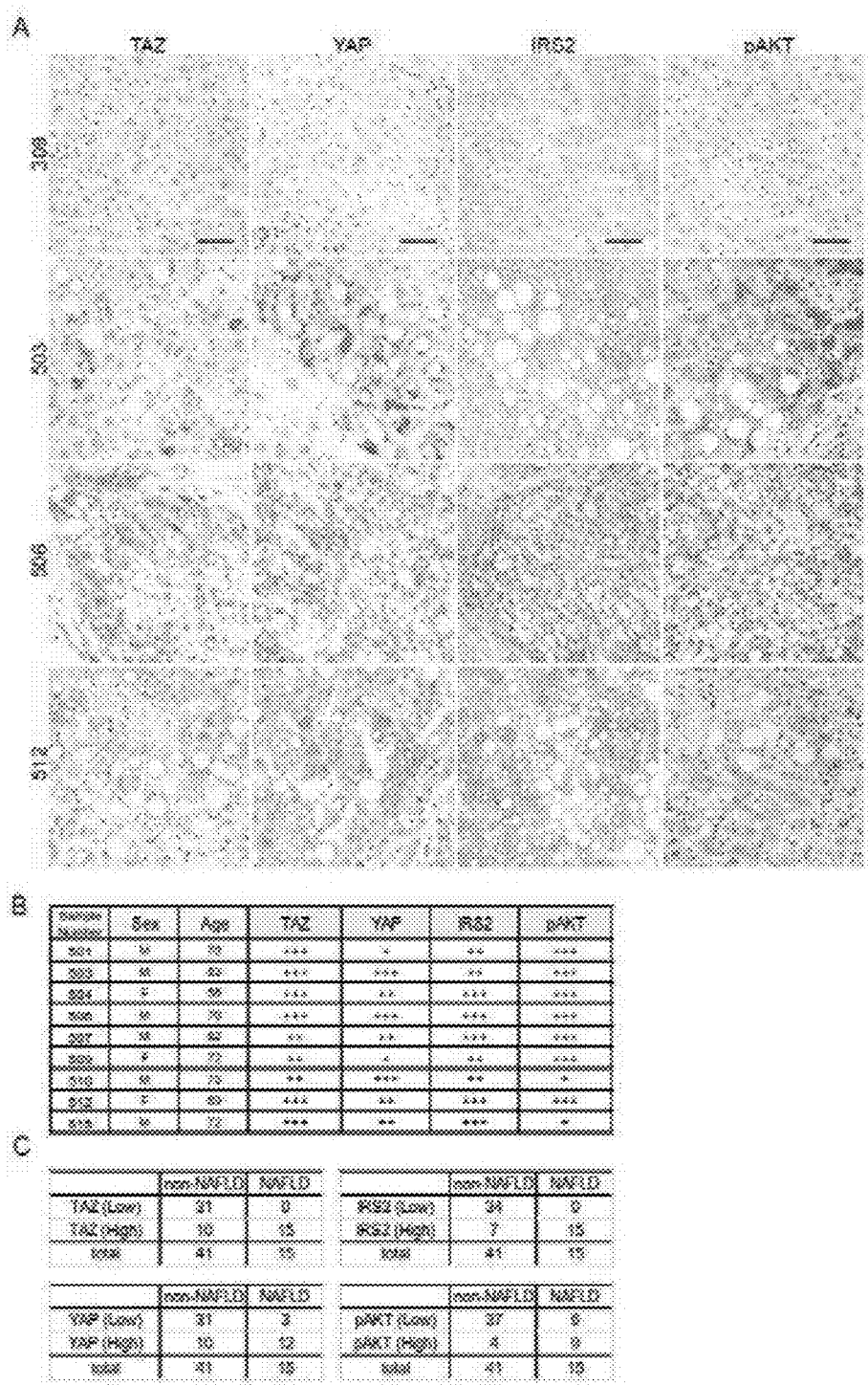

[FIG 17]
A
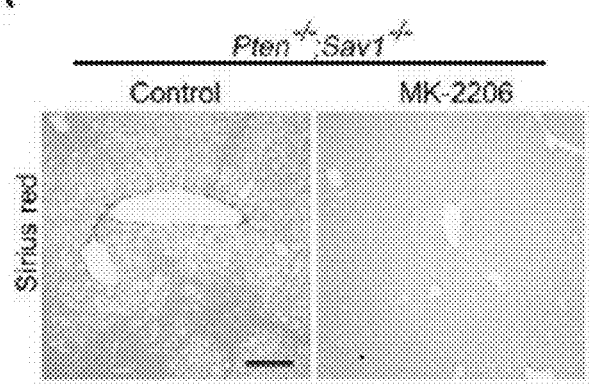
B
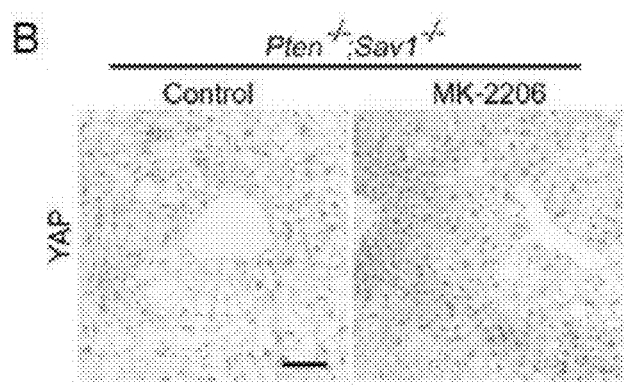

ANIMAL MODEL OF NON-ALCOHOLIC LIVER DISEASE AND COMPOSITION OF DIAGNOSIS, PREVENTION OR TREATMENT FOR NON-ALCOHOLIC LIVER DISEASE

CROSS-REFERENCE TO RELATED APPLICATIONS

This application claims the benefit of Korea Patent Application No. 10-2018-0070298 filed on Jun. 19, 2018 with the Korea Industrial Property Office, the entire disclosure of which is hereby incorporated by reference.

TECHNICAL FIELD

The present invention relates to an animal model of non-alcoholic liver disease caused by fat metabolism disorder which occurs by abnormal crosstalk between Hippo pathway and AKT pathway, a screening method for therapeutic agent using the animal model, and a method for diagnosis and screening of a therapeutic agent of non-alcoholic liver disease.

BACKGROUND ART

Liver cancer is the fifth most common tumor in the world, and their mortality is the second highest in all cancers. Liver cancer is divided into two major types: hepatocellular carcinoma (HCC), and cholangiocarcinoma (CC). In particular, HCC is the most important histological subtype of 70-85% of primary liver cancer. Chemotherapies with surgery have been tried in clinical practices, however, five-year survival rate of HCC patients is quiet low due to metastasis, recurrence, and resistance for chemotherapy and radiotherapy.

Non-alcoholic fatty liver disease (NAFLD) contains from simple steatosis in liver, to NASH(Non-alcoholic steatohepatitis), and cirrhosis; and it is seemed that their causes are obesity or fat accumulation in hepatocyte by insulin resistance, genetic reasons, and etc. The diagnosis of NAFLD is performed by ultrasound or biopsy. In particular, certifying the disease had not been caused by alcohol is important in order to distinguish from alcoholic liver disease (ALD). However, there are clinical difficulties because the certification is relying on patient's statement.

NASH which is progressed liver disease of NAFLD is predicted that its mortality would be increased, because it has high potential of progression to liver cancer through cirrhosis (Angulo P., Hepatology, 2010; 51:373-375). As the obesity population is increasing, the necessary for prevention of the diseases get higher, however, there is no effective method for prevention or treatment of NAFLD or NASH yet.

Most NAFLD patients show insulin resistance which represents higher concentration of insulin than normal range. It causes suppression of lipid degradation in fat tissue, and massive free fatty acids are flowed to liver, however, β-oxidation is suppressed due to high concentration of insulin and it results in lipid accumulation in liver. Meanwhile, insulin activates AKT and sterol regulatory element-binding protein 1c (SREBP1c) through IRS1 and IRS2. The SREBP1c, a transcription factor, are known as NAFLD causing factor by inducing de novo lipidogenesis by inducing lipidogenesis related fatty acid synthases and acetyl-CoA carboxylases (ACC) that converts excess glucose to neutral fat form and save them in liver.

On the other hand, the hippo signal transduction pathway contributes to cell proliferation, regulation of stem cell function, and cancer development. YAP/TAZ proteins are components of hippo signal transduction pathway, and it is known that overactivation of YAP/TAZ proteins induce cancer.

DISCLOSURE

Technical Problem

An object of the present invention is to provide methods of manufacturing an animal model of non-alcoholic liver disease.

Another object of the present invention is to provide a screening method of therapeutic agent for non-alcoholic liver disease comprising following steps: treating an animal model with a candidate substance;

measuring the expression level or the activity level of one or more proteins selected from the group consisting of YAP, TAZ, IRS2 and AKT from the liver tissue of the animal model treated with the candidate substance; and determining the candidate substance as the therapeutic agent for liver disease, when the expression level or the activity level is lower than that of a control liver tissue by comparing the expression level or the activity level of at least one protein selected from the group consisting of YAP, TAZ, IRS2, and AKT proteins in the liver tissue of the animal model treated with the candidate substance and the control liver tissue of the animal model untreated with the candidate substance

Technical Solution

To achieve the objects, the present invention provides an animal model of non-alcoholic liver disease that Pten and Sav1 genes were knocked out specifically in a liver, and method of manufacturing the animal model.

In addition, the present invention provides a screening method of therapeutic agent for non-alcoholic liver disease comprising following steps:

treating the non-alcoholic liver disease animal model with a candidate substance;

measuring the expression level or the activity level of one or more proteins selected from the group consisting of YAP, TAZ, IRS2 and AKT from the liver tissue of the animal treated with the candidate substance; and determining the candidate substance as the therapeutic agent for liver disease, when the expression level or the activity level is lower than that of a control liver tissue by comparing the expression level or the activity level of at least one protein selected from the group consisting of YAP, TAZ, IRS2, and AKT proteins in the liver tissue of the animal model treated with the candidate substance and the control liver tissue of the animal model untreated with the candidate substance.

Hereinafter, the present invention will be described in detail.

The present invention provides an animal model having double knock-out of Pten and Sav1 genes that causing non-alcoholic liver disease by activating YAP/TAZ proteins, promoting expression of IRS2 protein, and activating AKT protein. The non-alcoholic liver disease could be, for example, non-alcoholic fatty liver disease (NAFLD), non-alcoholic steatohepatitis (NASH), cirrhosis and liver cancer.

The animal model according to the present invention could be an animal model that having embryos with deposit number of KCTC 13522BP, specifically, the animal model could be an animal model whose embryo was deposited in the Korean Collection of Type Cultures (KCTC) of Korea Research Institute of Bioscience and Biotechnology (KRIBB) in 181, Ipsin-gil, Jeongeup-si, Jeollabuk-do, 56212, Republic of Korea, on May 9, 2018, and the deposit number was KCTC 13522BP.

In the present invention, the term "non-alcoholic liver disease" includes various liver diseases from simple fat accumulation in hepatocytes (fatty liver), to liver cancers through fatty liver (steatosis), non-alcoholic steatohepatitis (NASH). Preferably, non-alcoholic liver disease includes non-alcoholic fatty liver, NASH, cirrhosis or liver cancer, but not limited thereto.

In the present invention, the term "animal model" means a non-human animal having a disease quite similar with the disease of human. By physiological or genetical similarities, a biomedical disease model animal provides research materials about various causes, pathogenesis and diagnosis of diseases. Through disease animal model researches, genes related in certain disease and could be identified, interaction among the genes could be understand and the fundamental data for determining possibility of practical use by examining actual efficacy and toxicity of the candidate novel treating agent.

In the present invention, "animal" means any non-human mammals, preferably rodents such as mouse, rat, guinea pig, hamster, etc. Animals for the present invention, for example, could be used from commercial sources.

In the present invention, "defection" includes not only the whole deletion of genetic sequences, but also partial deletion when expression level of the protein coded by the gene is significantly decreased or completely deprived comparing with wild type. The gene defection could be performed by a method well known in the art.

In one embodiment of the present invention, it was revealed that every DKO mice that Pten and Sav1 genes were defected together had liver disease phenotype (Preparation Example 1, Example 1). The mouse provided by the present invention is preferable for an animal model that non-alcoholic liver disease is induced, because the mouse significantly promotes tumor than the previous Pten-deficient mouse.

The animal model could be characterized as occurrence of a cancer that progress to a tumor having both HCC and CC.

In one embodiment of the present invention, the DKO mouse that Pten and Sav1 genes were deleted together, showed rapid speed of tumorigenesis than Pten- or Sav1-defected mouse. Specifically, while $Pten^{-/-}$ or $Sav1^{-/-}$ mice developed liver tumors at 50 to 60 weeks, all DKO mice developed such tumors by 15 weeks (FIG. 1b). The result is differentiated with prior arts that non-alcoholic liver disease is induced by high-fat feedings, but does not reached to cirrhosis or liver cancer. Thus the DKO mice of the present invention have economic benefits that fatty liver, cirrhosis, and liver cancer were progressively developed despite feeds normal chow which is cheaper than high-fat chow.

In one embodiment of the present invention, while $Pten^{-/-}$ mice didn't appeared NAFLD phenotype until 3 months, DKO mice that Pten and Sav1 genes were detected together showed fatty acid accumulation only in 1-month-old livers (FIG. 1c). Accordingly, the present invention can provide non-alcoholic liver disease animal model having benefits on time-saving compare to prior art. When Pten and Sav1 genes were defected in adult mice using adenovirus expressing CRE recombinase, non-alcoholic fatty liver was developed, too (FIG. 11).

In one embodiment of the present invention, livers of DKO mice showed excessive accumulation of glycogen at the age of 1 month after birth and it grew progressively worse with time (FIG. 1c, FIG. 11). 3-month-old DKO livers showed increased apoptosis macrophage accumulation (FIG. 1c, FIG. 11). They showed advanced NAFLD and fibrosis and these results suggest progression to NASH.

In one embodiment of the present invention, results of liver to body weight ratio analysis, analysis of liver enzymes (AST and ALT) in serum of mice having each genotypes, quantification analysis of apoptotic cell and macrophage showed that AST and ALT in serum of the DKO mice of 3 months of age (FIG. 1d), and pan-CK-positive hepatic progenitor cells were increased in nonductal regions at 5 months of age (FIG. 11). Collectively, these results indicate that deletion of Sav1 accelerates the progression of $Pten^{-/-}$ livers through the steps NAFLD, NASH, cirrhosis, and cancer.

It is known that the mouse model provided by the present invention is preferable for an animal model that non-alcoholic liver disease is induced because it shows characteristics that faster progression speed of NAFLD and NASH than Pten- or Sav1-deleted mice, liver disease phenotype shown in every individual, and promoting progression to liver cancer.

Compare to the format animal model of non-alcoholic liver disease, the animal model of non-alcoholic liver disease provided by the present invention have following benefits:

(1) Inducing the disease with feeding normal chow unlike expensive high-fat chow that is used for the former method;

(2) Reducing time not only the onset time of non-alcoholic liver disease, but also time to development of liver cancer progressed from the non-alcoholic liver disease;

(3) Outstanding to mimic progression of liver disease in human because hepatosteatitis, cirrhosis, and liver cancer are progressively developed;

(4) Could be used as an animal model for screening of novel drugs because the mechanism of disease have been discovered, and a drug under clinical tiral showed effect on the animal model.

One example of the present invention provides method of manufacturing of an animal model of non-alcoholic liver disease comprising a step of preparing an animal model that Pten and Sav1 genes were defected specifically in a liver.

The step of preparing an animal model could be performed by any method as long as the method is objected to defect or knockout a certain gene specific to tissue in a non-human animal. For example, the method could use, but not limited to, a Cre recombinase expressed specifically in certain tissue, or adenovirus.

In case of using the Cre recombinase that is expressed specific to tissue in order to defect Pten and Sav1 genes specifically in a liver, an animal whose genotype is Albumin-Cre could be used.

More specifically, a method of manufacturing an animal model for non-alcoholic liver disease by defecting Pten and Sav1 genes specifically in a liver using the animal whose genotype is Albumin-Cre, could comprise the following three steps:

obtaining a first generation animal by mating an animal of $Pten^{f/f}$ genotype and an animal of Albumin-Cre genotype expressing CRE;

obtaining a second generation animal by mating the first generation animal and an animal of $Sav1^{f/f}$ genotype; and obtaining a third generation animal comprising Pten$^{f/f}$; Sav1$^{f/f}$;Albumin-Cre genotype by mating between the 2$^{nd}$ generation animals.

The animal of Albumin-Cre genotype is useful for liver-specific knockout of a certain gene, due to their characteristic that Cre recombinase is expressed specifically in a liver.

The second generation animal gained by mating the first generation animal and an animal of Sav1$^{f/f}$ genotype could be an animal comprising Pten$^{f/+}$;Sav1$^{f/+}$;Albumin-Cre or Pten$^{f/+}$;Sav1$^{f/+}$ genotype.

The step of obtaining a third generation animal could be a step of obtaining by mating an animal of the second generation comprising Pten$^{f/+}$;Sav1$^{f/+}$;Albumin-Cre genotype, and an animal of the second generation comprising Pten$^{f/+}$;Sav1$^{f/+}$ genotype.

In one embodiment of the present invention, a Pten$^{f/f}$; Sav1$^{f/f}$;Albumin-Cre mouse was gained and used as a double knock-out (DKO) mouse. All mice having the DKO genotype showed liver disease phenotype regardless their gender, however, only male mice were used in the embodiments of the present invention.

The method of manufacturing an animal model of non-alcoholic liver disease provided by the present invention could be characterized by normal feeding to the 3$^{rd}$ generation animal without expensive high-fat feedings.

The method of manufacturing an animal model provided by the present invention has an economic benefit which is able to provide an animal model progressively developing fatty liver, NASH and liver cancer, with normal feedings which are cheaper than high-fat feedings.

In addition, the method of manufacturing animal model provided by the present invention has a benefit that able to provide an animal model having 100% of non-alcoholic liver disease onset possibilities, progressing the disease fast, and mimicking well the progression to liver cancer.

One example of the present invention provides a screening method of therapeutic agent for non-alcoholic liver disease comprising following steps:

Treating a candidate substance to the animal model;

Measuring expression or activity level of one or more proteins selected from the group consisting of YAP, TAZ, IRS2, and AKT from the liver tissue of the animal treated with the candidate substance; and Determining the candidate substance as a treating agent when the expression or activity level of the protein is lower than that of control liver tissue by comparing the measured expression or activity level of at least one protein selected from the group consisting of YAP, TAZ, IRS2 and AKT with the control liver tissue that the candidate substance was not treated.

The proteins that objected to measure the expression or activity level could be at least one protein selected from the group consisting YAP, TAZ, IRS2, and AKT proteins, preferably, proteins of 1$^{st}$ group which are at least one protein selected from the group consisting of YAP and TAZ, and proteins of 2$^{nd}$ group which are at least one protein selected from the group consisting of IRS2 and AKT.

The step of measuring expression or activity level of proteins could be performed by a method measuring mRNA transcription level. The mRNA could be a mRNA transcribed from a gene coding the protein, or a mRNA transcribed from a target gene regulated by the protein. Preferably, YAP/TAZ proteins regulates Irs2 gene, IRS2 protein regulates AKT activity regulates TAZ stability. The method measuring mRNA transcription level could be, but are not limited to, one or more methods selected from the group consisting of PCR, reverse transcription PCR (RT-PCR), real-time PCR, RNase protection assay (RPA), microarray, and northern blotting.

The step of measuring expression or activity level of proteins could be, but are not limited to, performed by one or more methods selected from the group consisting of Western blotting, radioimmunoassay (RIA), radioimmunodiffusion, ELISA, immunoprecipitation (IP), flow cytometry, immunofluorescence, ouchterlony, complement fixation assay, and protein chip.

The candidate substance could be a repressor for AKT protein activity.

In the present invention, the term "candidate substance" means a substrate for testing as a therapeutic agent for non-alcoholic fatty liver disease, and could comprise any molecules, such as extract, protein, oligopeptide, small organic molecule, polysaccharide, polynucleotide, and wide range of compounds, etc. The candidate substance could comprise for example, at least one substance selected from the group consisting of primer, probe, aptamer, antisense oligonucleotide, polymeric compound, protein, peptide, nucleic acid molecule, virus, and antibody. The candidate substance can comprise synthetic materials as well as natural materials.

Effect of Invention

An animal model according the present invention shows liver disease phenotype in 100% of percentage by using crosstalk of Hippo and AKT signaling pathways, and having economical and timely advantages because the animal model shows faster disease progression than former animal models which are each pathway-defected. The animal model could be usefully used for diagnosing method of non-alcoholic liver disease, screening of treating agents, and development of novel drugs. In addition, by the interaction between Hippo signaling and metabolic pathway had been discovered, effective treating agent, diagnosing method, and screening method of therapeutic agent for non-alcoholic liver disease could be provided.

BRIEF DESCRIPTION OF DRAWINGS

The patent or application file contains at least one drawing executed in color. Copies of this patent or patent application publication with color drawing(s) will be provided by the Patent and Trademark Office upon request and payment of the necessary fee.

FIG. 1a shows livers from 5-month-old mice of the indicated genotypes. DKO (Pten$^{-/-}$;Sav1$^{-/-}$) livers show advanced tumor development.

FIG. 1b shows tumor-free rate (top) and survival rate (bottom) for mice of the indicated genotypes.

FIG. 1c shows Oil Red 0 (lane 1), PAS (lane 2) staining result of livers from of 1-month-old mice as well as H&E (lane 3), Picrosirius red (lane 4), TUNEL (lane 5) and F4/80 (lane 6) staining result of livers from 3-month-old mice. Scale bars are 100, 50, 100, 200, 200, and 100 um respectively, from the top.

FIG. 1d shows a graph of liver-to-body weight ratio for mice at 2 and 4 months of age (E) and a graph of liver enzymes (aspartate aminotransferase [AST] and alanine aminotransferase [ALT]) in the serum of 3-month-old mice of the indicated genotypes (F), and a graph of quantification of apoptotic cells and macrophages following the TUNEL and F4/80 staining above (G).

FIG. 2a shows a heatmap of differentially expressed genes in the livers of 3-month-old mice as revealed by microarray analysis.

FIG. 2b shows the GSEA for Pten$^{-/-}$;Sav1$^{-/-}$ (DKO) livers compared with Pten$^{-/-}$ livers. Upregulated gene signatures in DKO mouse livers are depicted using MSigDB (Broad Institute). NES, normalized enrichment score; NOM p-val, nominal P value; FDR q-val, FDR q value.

FIG. 2c shows the result of immunoblot analysis of AKT signaling components and lipogenesis-related proteins in the livers of 3-month-old mice.

FIG. 2d shows the result of immunohistochemical staining of p-AKT (Ser473) and immunofluorescence staining of PIP$_3$ in the livers of 3-month-old mice. Scale bars: 50 um (left), 100 um (right).

FIG. 2e shows the result of qPCR analysis of relative mRNA levels for lipogenesis- or inflammation-related genes in the livers of 3-month-old mice.

FIG. 3a shows the result of immunoblot analysis of Hippo pathway components in livers from 3-month-old mice of the indicated genotypes.

FIG. 3b shows the result of immunohiotochemical staining analysis of YAP/TAZ. Scale bar: 50 um FIG. 3c shows the result of quantification of YAP/TAZ localization from FIG. 3b. C: cytoplasm; N: Nucleus.

FIG. 3d shows the expression result of YAP and TAZ after nuclear/cytoplasmic fractionation in livers from 1-month-old mice of indicated genotypes LaminB and GAPDH were control in nucleus and cytoplasm, respectively.

FIG. 3e shows the result of microscopic appearance and H&E and Oil red O staining of livers from 6-week-old wild type (WT) mice and Pten$^{-/-}$ mice 4 days after injection with adenoviruses (Ad) encoding GFP, TAZ4SA, or YAP5SA at 6 weeks of age. Arrows indicate hepatocytes with excessive lipid droplets.

FIGS. 3f and 3g show the results of immunoblot analysis of livers as in FIG. 3e.

FIG. 4a shows the result of immunoblot analysis of insulin signaling molecules in the livers of 3-month-old mice.

FIG. 4b shows the result of qPCR analysis of Irs2 mRNA levels in the same livers as in FIG. 4a.

FIG. 4c shows the result of IRS2 immunoblot analysis of AML12 cells, the normal hepatocyte cell line, that Pten and/or Sav1 expression are suppressed by infecting the cells with lentiviruses encoding shPten and/or shSav1.

FIG. 4d shows the result immunoblot analysis for AKT activity induced by insulin of AML 12 cells manufactured in FIG. 4c.

FIG. 4e shows the result of immunoblot analysis of AKT activity of AML12 cells that IRS2 expression is increased.

FIG. 4f shows the result of immunoblot analysis that the AKT activity was reduced in the AML 12 cells of FIG. 4c that showed decreased expression of Pten and Sav1 when the expression of Irs2 was suppressed by using siRNA.

FIG. 4g shows the result of immunoblot assay of comparing the increase of IRS2 in AML12 cells that TAZ4SA or TAZ4SA/S51A was overexpressed, and in control (CTL)

FIG. 4h is a schematic diagram of Luciferase (Luc) reporter constructs that include regions of the Irs2 distal promoter and first intron of TEAD binding region (TBSs) or deleted region (TBSsΔ). Ex: exon.

FIG. 4i shows the result of luciferase reporter analysis for expression pattern of Luc in FIG. 4h when the CTL, TAZ4SA, or TAZ4SA/S51A was overexpressed.

FIG. 4j shows a result of ChIP-qPCR analysis of whether TAZ binds to the Irs2 distal promoter or intron analyzed in FIG. 4i. After overexpressing control or TAZ4SA in AML12 cells, and the cells were subjected to immunoprecipitation with antibodies recognizing TAZ or IgG. qPCR was performed after the immunoprecipitation.

FIG. 5a represents the result of H&E and Oil red O staining of livers from 1-month-old mice. Scale bars: 100 um (top), 50 um (bottom).

FIG. 5b represents the immunoblot analysis result of IRS2/AKT and YAP/TAZ signal transduction pathway.

FIG. 5c shows the result of the qPCR analysis of relative Irs2 mRNA levels in the livers of mice as in FIG. 5a.

FIG. 6a shows the macroscopic appearance of livers from 2-month-old Pten$^{-/-}$, Pten$^{-/-}$ MSTWT$^{Tg}$ mice.

FIG. 6b shows the H&E staining, Oil red O staining and YAP and TAZ IHC results of the livers of mice as in FIG. 6a. Scale bars: 50 um (top 2 rows), 100 um (bottom 2 rows).

FIG. 6c shows the result of immunoblot analysis of livers from mice as in FIG. 6a. β-actin was used as a loading control.

FIG. 7a shows scatter plots of log$_2$ (mRNA abundance) values for IRS2 versus TAZ or YAP1 in tissue specimens from patients with liver cancer or cirrhosis, HCC, or both HCC and cirrhosis.

FIG. 7b shows scatter plots of log 2 (mRNA abundance) values for IRS2 versus CTGF or CYR61 in the samples as in FIG. 7a.

FIG. 7c shows the IHC result of TAZ and IRS in HCC patients' specimens, and a comparison of their corresponding levels of expression using the $\chi^2$ test. Scale bars: 100 um. ND: not detected.

FIG. 7d shows the IHC result of YAP and IRS in HCC patients' specimens, and a comparison of their corresponding levels of expression using the $\chi^2$ test. Scale bars: 100 um. ND: not detected.

FIG. 7e represents the images of HCC specimens with associated NAFLD that had high TAZ, YAP, IRS2, and p-AKT IHC intensities compared with HCC specimens not associated with NAFLD (Non-NAFLD). Scale bar: 50 um.

FIG. 7f shows a graph of quantification of the percentage of specimens from FIG. 7e.

FIG. 8a represents the experimental design used to treat 3-week-old DKO mice for 2 weeks with MK-2206 or vehicle (control). Macroscopic appearance of the liver as well as H&E and Oil red O staining are shown. Scale bar: 50 um.

FIG. 8b is a graph of liver-to-body weight ratio percentage in control and MK-2206.

FIG. 8c is a graph showing the analysis of liver enzymes in the serum in control and MK-2206.

FIG. 8d is a graph representing qPCR analysis result of lipogenesis-related gene expression in the liver of control (white bars) and MK-2206 (red bars).

FIG. 8e shows the schematic diagram of experimental design used to treat 12-week-old DKO mice for 2 weeks with MK-2206 or vehicle (top), and macroscopic appearance of their livers (bottom). Black arrows indicate tumor nodules.

FIG. 8f shows the result of liver-to-body weight ratio (F), liver tumor number and size (G), serum analysis (H) of the experiment shown in FIG. 8e. Chol, Cholesterol; TG, triglycerides.

FIG. 8g shows the results of H&E, Picrosirius red, Ki-67, and TAZ immunohistochemistry staining Scale bars: 300, 400, 100, 100 um (top to bottom, respectively).

FIG. 8h is a graph representing the quantification analysis of Ki-67$^+$ hepatocytes of specimen as in FIG. 7g.

FIG. 8i is a graph representing the qPCR analysis of the expression of genes related to fibrosis (Acta2, Desmin, and Tgfb), cell death or injury (Hmox1 and Gadd153), or inflammation (Tnfa).

FIG. 9a shows the result of the macroscopic appearance of the liver 7 weeks after injection of AAV virus encoding Cas9 and an sgRNA against Irs2 (sgIrs2) or an sgCtl into 5-week-old DKO mice. Black arrowheads indicate tumor nodules.

FIG. 9b represents the immunoblot result of experiment as in FIG. 9a.

FIG. 9c shows two graphs representing liver-to-body weight ratio (left) and liver tumor number and size (right) as in FIG. 9a.

FIG. 9d shows the result of H&E staining of livers of the FIG. 9a. Magnification ×40.

FIG. 10 represents schematic diagrams for the positive feedback loop linking Hippo/YAP/TAZ and IRS2/AKT signaling in the liver of DKO (Pten$^{-/-}$;Sav1$^{-/-}$) mice. Hippo signaling interacts with AKT signaling by regulating IRS2 expression and prevents NAFLD and liver cancer progression.

FIG. 11 shows that liver-specific Pten and Sav1 double-knockout (DKO) mice show accelerated development of liver dysfunction. (A) Schematic for the generation of liver-specific DKO mice. (B) Representative H&E staining of combined hepatocellular carcinoma (HCC) and cholangiocarcinoma (CC) tumor types in DKO mouse livers. Scale bar, 100 um. (C) PAS, Sirius red, and panCK immunohistochemical staining of the livers of mice at the indicated ages. Scale bars: 50 μm (PAS), 200 μm (Sirius red), and 100 μm (panCK). n=5 for each group in all analyses. (D-E) Acute adult-stage deletion of Pten and Sav1 induces fatty liver. Microscopic appearance (D) and H&E staining (E) of livers from 6-week-old Pten$^{f/f}$;Sav1$^{f/f}$ mice injected with adenovirus encoding CRE and GFP (control). Scale bars, 50 μm.

FIG. 12 shows that a short-term increase of YAP or TAZ activity promotes fatty liver development without fibrosis or inflammation. The liver-to-body weight ratio (A) as well as representative Sirius red staining and F4/80 immunofluorescence staining (green fluorescence) of the liver (B, C) are shown for 6-week-old WT (B) or Pten$^{-/-}$ (C) mice (n=3) 4 days after injection with adenoviruses encoding GFP, TAZ4SA, or YAP5SA. Nuclei in (B) and (C) were stained with 4',6-diamidino-2-phenylindole (blue fluorescence). Scale bars, 200 μm (top panels) or 100 μm (bottom panels).

FIG. 13 shows that Pten$^{-/-}$;Sav1$^{-/-}$;Yap$^{-/-}$;Taz$^{-/-}$ livers develop pronounced fibrosis. (A) Schematic for the generation of Pten$^{-/-}$;Sav1$^{-/-}$;Yap$^{-/-}$;Taz$^{-/-}$ mice. (B-D) Liver-to-body weight ratio (B), Sirius red and CK19 immunohistochemical staining of the liver (C), and isolated serum color (D) for 1-month-old mice (n=3) of the indicated genotypes. Scale bars (C), 200 μm (top) or 100 μm (bottom); arrows indicate ducts.

FIG. 14 shows that the ablation of both Yap and Taz leads to ductal malformation and severe fibrosis. (A-G) Macroscopic appearance of the liver (A), isolated serum color (B), liver-to-body weight ratio (C), serum analysis (D, E), H&E, Sirius red, and CK19 immunohistochemical staining of the liver (F), and immunoblot analysis of the liver (G) for 1-month-old WT or liver-specific Yap$^{-/-}$;Taz$^{-/-}$ mice (each group, n=3). Scale bars (F), 100 μm (top and bottom) or 200 μm (middle); arrows indicate ducts. T. Bilirubin, total bilirubin; Chol, cholesterol; TG, triglycerides.

FIG. 15 shows that expression of a kinase-dead form of MST1 does not rescue the fatty liver phenotype of Pten mice. (A) Schematic for the generation of Pten$^{-/-}$;MST wt$^{Tg}$ or Pten$^{-/-}$;MSTkd$^{Tg}$ mice. (B) Liver-to-body weight ratio for 2-month-old mice (each group, n=3) of the indicated genotypes. Data are means±s.e.m. (C-D) Macroscopic appearance (C), and immunoblot analysis (D) of the livers from 2-month-old mice (n=3) of the indicated genotypes.

FIG. 16 shows the comparison of IHC intensities of TAZ, YAP, IRS2, and pAKT (S473) protein levels between NAFLD-associated HCC and non-NAFLD HCC. (A) Representative immunohistochemical staining of TAZ, YAP, IRS2, and pAKT (S473) in human HCC not associated with NAFLD (sample No. 309) or associated with NAFLD (sample No. 503, 506, 512). Scale bars, 50 (B) Immunohistochemistry signal intensity scores for TAZ, YAP, IRS2, and pAKT in human HCC associated with NAFLD. −, no expression; +, low expression; ++, moderate expression; +++, high expression. (C) The number of specimens with intense staining of TAZ, YAP, IRS2, and pAKT in the human HCC associated with NAFLD compared to HCC not associated with NAFLD.

FIG. 17 represents the effects of MK-2206 treatment on the liver of DKO mice. (A) Representative Sirius red staining of the liver of DKO mice treated for 2 weeks with MK-2206 or vehicle beginning at 3 weeks of age. Scale bar, 200 μm. (B) Representative YAP staining of the liver of DKO mice treated for 2 weeks with MK-2206 or vehicle beginning at 12 weeks of age. Scale bar, 100 μm.

MODE FOR INVENTION

Hereinafter, the present invention will be described by Preparation Examples and Examples in detail. However, the following Preparation Examples and Examples are intended to illustrate the present invention, and should not be construed as limiting the present invention.

<Preparation Example 1> Generation of Liver-Specific Knockout and Transgenic Mice (1) Generation of Liver-Specific Knock Mouse and DKO Mouse Sav1$^{f/f}$(PNAS, May 4, 2010. 107 (18) 8248-8253), Pten$^{f/f}$(The journal of Clinical Investigation, 2004; 113(12): 1774-1783), Yap$^{f/f}$(Science Signaling, 2011 Oct. 25; 4(196): ra70), Taz$^{f/f}$(PNAS, Aug. 20, 2013. 110(34) 13839-13844), MSTwt$^{Tg}$, and MSTkd$^{Tg}$(PLoS One. 2009 Nov. 24; 4(11): e8011) mice were generated as previously described in each paper. Mice were crossed as indicated to obtain the desired genotypes.

For example, DKO(PTEN$^{-/-}$, Sav1$^{-/-}$) mice was obtained from the 2$^{nd}$ generation mice that obtained by mating of the 1$^{st}$ generation mice (Pten$^{f/+}$;Sav1$^{f/+}$;Albumin-Cre and Pten$^{f/+}$;Sav1$^{f/+}$) that obtained by mating of Pten$^{f/f}$;Albumin-Cre mice and Sav1$^{f/f}$ mice. Only male mice were used for the present invention, and mice with the DKO genotype had 100% liver disease phenotype.

The mice were genotyped by PCR analysis using the primers listed in Table 1 (Mice genotyping).

(2) Generation of Transgenic Mice

Adenovirus for overexpression of CRE, YAP5SA, TAZ4SA, or GFP (control) and AAV-saCas9-sgIrs2 or sgCtl in the mouse liver were injected into the tail vain of 6- and 5-에-old mice, respectively. The mice were deprived of food for 16 hours at day 4 (YAP5SA, TAZ4SA, and GFP) or week 4 (CRE and GFP) after adenovirus injection. MK-2206 (Selleckchem; S1078) was prepared in 30% Captisol (CyDex Pharmaceuticals; RC-0C7) and administered to DKO mice by intraperitoneal injection at a dose of 66 mg/kg every other day for 2 weeks, beginning at 3 or 12 weeks of age.

TABLE 1

| Gene | Sense | SEQ ID NO | Antisense | SEQ ID NO |
|---|---|---|---|---|
| RT-qPCR | | | | |
| Srebp1a | 5'-GGCCGAGATGTGCGAACT-3' | 1 | 5'-TTGTTGATGAGCTGGAGCATGT-3' | 2 |
| Srebp1c | 5'-GGAGCCATGGATTGCACATT-3' | 3 | 5'-CAGGAAGGCTTCCAGAGAGG-3' | 4 |
| Srebp2 | 5'-GCGTTCTGGAGACCATGGA-3' | 5 | 5'-ACAAAGTTGCTCTGAAAACAAATCA-3' | 6 |
| Fasn | 5'-GCCTACACCCAGAGCTACCG-3' | 7 | 5'-GCCATGGTACTTGGCCTTG-3' | 8 |
| Acc1 | 5'-CAACGAGATTTCACTGTGGCT-3' | 9 | 5'-TTCTGCATTGGCTTTAAGGTCT-3' | 10 |
| Scd1 | 5-CCGGAGACCCCTTAGATCGA-3' | 11 | 5'-TAGCCTGTAAAGATTTCTGCAAACC-3' | 12 |
| Tnfa | 5'-CATCTTCTCAAAATTCGAGT-3' | 13 | 5'-TGGGAGTGACAAGGTACAA-3' | 14 |
| Il6 | 5'-TCCACGATTTCCCAGAGAAC-3' | 15 | 5'-AGTTGCCTTCTTGGGACTGA-3' | 16 |
| Irs2 | 5'-CAAGAGCCCTGGCGAGTACA-3' | 17 | 5'-CCGCGGATGCCAGTAGTG-3' | 18 |
| Acta2 | 5'-ATGCTCCCAGGGCTGTTTTCCCAT-3' | 19 | 5'-GTGGTGCCAGATCTTTTCCATGTCG-3' | 20 |
| Desmin | 5'-CTAAAGGATGAGATGGCCCG-3' | 21 | 5'-GAAGGTCTGGATAGGAAGGTTG-3' | 22 |
| Tgfb | 5'-CTCCCGTGGCTTCTAGTGC-3' | 23 | 5'-GCCTTAGTTTGGACAGGATCTG-3' | 24 |
| Hmox1 | 5'-GCTCGAATGAACACTCTGG-3' | 25 | 5'-GTTCCTCTGTCAGCATCAC-3' | 26 |
| Gadd 153 | 5'-CTGGAAGCCTGGTATGAGGAT-3' | 27 | 5'-CAGGGTCAAGAGTAGTGAAGGT-3' | 28 |
| Luciferase reporter structure | | | | |
| TBS1 | 5'-CTTATCTGGCAGCAGGAAGGAGAG-3' | 29 | 5'-CACACCCTCGCACACATATCCCTC-3' | 30 |
| TBS2 | 5'-CACCCTTGCACACGTAGAGACGCT-3' | 31 | 5'-ACCGTGTTCACCCAGCACCCGGG-3' | 32 |
| TBS3 | 5'-CCTGGCAGTGTCCCATAGTTGA-3' | 33 | 5'-CAGCTGCTGCTTCTTTAGGGG-3' | 34 |
| TBS4 | 5'-GCAGCAGCTGAAGTGCTAAAGA-3' | 35 | 5'-GCTGCTTTCCTCTCATTGCTC-3' | 36 |
| TBS5 | 5'-GCCTCTGAGCCAACATCTCTCT-3' | 37 | 5'-TATGACCTCCCACCCACTTCA-3' | 38 |
| TBS6 | 5'-CATGGCTCGTTTCTCCTTCTGG-3' | 39 | 5'-GAGTACTCAGGCCCAGGATGC-3' | 40 |
| ChIP-qPCR | | | | |
| TBS1 | 5'-ATCTATGGTCTTCAGAATCACAC-3' | 41 | 5'-CCAGAGTTTATCTTACAATTTAACCT-3' | 42 |
| TBS2 | 5'-CACAGTTTACACAAAGGGTAAAGCA-3' | 43 | 5'-GCTCTGGATGCGTAAACAAAACA-3' | 44 |
| TBS4 | 5'-GCAGCAGTTGATTCCCATCCT-3' | 45 | 5'-ACAATGGGGCAGGGAAGGTA-3' | 46 |
| TBS5 | 5'-GTAAAACCCAGAAACCCCACTTTC-3' | 47 | 5'-TGCTCTGCTTCTCTCACTAGGA-3' | 48 |
| Mice genotyping | | | | |
| Sav1 | 5'-TGGTTTGCTTTTTAGTGGCC-3' | 49 | 5'-TGCTGGTTTTGTCTCACTAA-3' | 50 |
| Pten | 5'-CTCCTCTACTCCATTCTTCCC-3' | 51 | 5'-ACTCCCACCAATGAACAAAC-3' | 52 |
| Yap1 | 5'-ACATGTAGGTCTGCATGCCAGAGGAGG-3' | 53 | 5'-AGGCTGAGACAGGAGGATCTCTGTGAG-3' | 54 |
| Taz | 5'-GGCTTGTGACAAAGAACCTGGGGCTATCTGAG-3' | 55 | 5'-CCCACAGTTAAATGCTTCTCCCAAGACTGGG-3' | 56 |
| Cre | 5'-GTGTTGCCGCGCCATCTGC-3' | 57 | 5'-CACCATTGCCCCTGTTTCACTATC-3' | 58 |
| MSTTg | 5'-GCTCTAGAGCCTCTGCTAACCA-3' | 59 | 5'-CCAGGGACCAGATGTCTGC-3' | 60 |
| Adenovirus-sgIrs2 | | | | |
| Ex1-1 | 5'-CACCGATCGCCCTCTACACCAAGG-3' | 61 | 5'-AAACCCTTGGTGTAGAGGGCGATC-3' | 62 |
| Ex1-2 | 5'-CACCGCCGCCGCAGCCTCCGCGGC-3' | 63 | 5'-AAACGCCGCGGAGGCTGCGGCGGC-3' | 64 |

<Preparation Example 2> Histology, Immunostaining, and TUNEL Staining

For immunohistochemical staining, 4-μm liver sections on slides were serially rehydrated with xylene and ethanol before heat-induced antigen retrieval (10 mM sodium citrate, pH 6.0; Duchefa). The antigen retrieval step was skipped for slides stained with the anti-IRS2 antibody. Blocking was performed with 0.3% BSA in PBS for the p-AKT-specific antibody and 5% goat serum in 3% BSA including 0.3% Triton-X for all other antibodies. After quenching endogenous peroxidases with hydrogen peroxide (Merck), the samples were incubated with a primary antibody in blocking solution. After washing and incubation with an HRP-conjugated anti-rabbit secondary antibody (Jackson Immunoresearch; 1:500), DAB (Vector Laboratories) was added for antigen detection. Finally, the slides were counterstained with hematoxylin. The antibodies used for immunohistochemical and immunohistofluorescence staining included those specific to Ser473 phosphorylated AKT (p-AKT) (Cell Signaling Technology; 4060); TAZ (Millipore Sigma; HPA007415); YAP (Cell Signaling Technology; 4912); Ki-67 (Abcam; 16667); pan-CK (Dako; Z0622); CK19 (Abcam; 15464); F4/80 (Abcam; 105155); PIPS (Echelon; Z-P345); and IRS2 (Abcam; 84906). For Oil red O staining, cryosections (10-μm thickness) of liver tissue were fixed with cold 10% formalin, dehydrated with 100% propylene glycol (MilliporeSigma; 398039), washed with 85% propylene glycol, and then stained with 0.5% Oil red O (MilliporeSigma; O0625). The sections were counterstained with Mayer's hematoxylin (MilliporeSigma; MHS1). Staining with Picrosirius red was performed with a solution of 0.1% Direct Red (MilliporeSigma; 365548) and 0.1% Fast Green (MilliporeSigma; F7252) in picric acid and subsequently incubated in 0.5% acetic acid. For PAS staining, the sections were incubated with 0.5% periodic acid followed by the Schiff reagent (MilliporSigma; 3952016). TUNEL staining was performed with the In Situ Cell Death Detection Kit (Roche; 11684795910).

<Preparation Example 3> Immunoblot Assay

Liver or AML12 cell lysates were prepared with Proprep Lysis Buffer (Intron Biotechnology) and NETN buffer (20 mM Tris-HCl [pH 7.4], 100 mM NaCl, 1 mM EDTA, 0.5% nonidet P-40), respectively. For nuclear/cytoplasmic fractionation analysis, frozen liver tissue was added to lysis buffer (10 mM HEPES [pH 7.8], 10 mM KCl, 1.5 mM MgCl2, 0.5 mM DTT, and protease inhibitors) for cytoplasmic extraction. After grinding the tissue with a hand pestle, the tissues were mixed with 0.3% NP-40 by vortexing for 5 seconds, and the cytoplasmic fraction was obtained from the supernatant after centrifugation. After 2 washes in PBS, the pellet was boiled in sample buffer and used as the nuclear fraction. The primary antibodies for the immunoblot analyses included those specific to p-AKT (catalog 4051 or 4056), AKT2 (catalog 3063), p-GSK3β (catalog 9336), p-S6K (catalog 9205), FAS (catalog 3189), p-ACC (catalog 3661), PTEN (catalog 9559), MST1 (catalog 3682), p-YAP (catalog 4911), YAP (catalog 4912), TAZ (catalog 4883), LATS2 (catalog 5888), p-LATS (catalog 8654), and p-ERK (catalog 4376) (all from Cell Signaling Technology); to IR (catalog 07-724), the p85 subunit of PI3K (catalog 06-195), IRS1 (catalog 06-248), and IRS2 (catalog 06-506) (all from MilliporeSigma); to SREBP1 (catalog 28481), FAS (catalog 196854), ACC (catalog 45174), and GAPDH (catalog 125247) (all from Abcam); to lamin B (catalogs 6217), CTGF (catalog 14939), and CYR61 (catalog 13100) (all from Santa Cruz Biotechnology); to β-actin (catalog A5316; MilliporeSigma); and to α-tubulin (catalog LF-PA0146; Abfrontier). The SAV1-specific antibody was developed in our laboratory. See complete unedited blots in the supplemental material.

<Preparation Example 4> Adenovirus and AAV Preparation

The CRE, human TAZ4SA, and YAP5SA cDNAs were cloned separately into the pAdtrack-CMV-GFP vector. The resulting vectors were then recombined with the pADEasy-1 vector in BJ5183-AD-1 electroporation-competent cells (Agilent Technologies; 240005 and 200157). The recombinant DNA was linearized with PacI and introduced into 293AD cells by transfection with polyethyleneimine (Polyscience; 23966). After checking the cells for GFP expression, we pelleted them with centrifugation, resuspended them with 10% glycerol in PBS, and lysed them with 4 freeze-thaw cycles (LN$_2$ and a 47° C. water bath) to release their viruses. To amplify the adenoviruses, the present inventors repeated this step with increasing numbers of cells. The adenoviruses were finally purified by ultracentrifugation at 46,000×g for 2 hours at 4° C. on a discontinuous gradient from 2.2 to 3.0 M CsCl (Amresco) in 10 mM HEPES (MilliporeSigma). The adenovirus-containing layer was removed with a syringe needle, and the viruses were washed twice in a solution containing 10 mM Tris-HCl (pH 8.0) and 2 mM MgCl2 using an Amicon Ultra Centrifugal Filter (MilliporeSigma; UFC810024). Virus titration was performed by counting exposed 293AD or target cells positive for GFP with a fluorescence microscope. A total of $1\times10^9$ to $1\times10^{10}$ PFU were used for tail-vein injections. For the generation of an AAV encoding saCas9-sgRNA against Irs2, we used the pX602-AAV-TBG::NLS-SaCas9-NLS-HA-OLLAS-bGHpA;U6::BsaI-sgRNA vector, which was purchased from Addgene (plasmid 61593). The steps for AAV generation, concentration, and purification were performed as previously described (Nature, v.520, p.186-191). Genomic copies of AAV ($2\times10^{10}$ to $2\times10^{11}$) were used for tail-vein injections into 5-week-old mice that were analyzed 7 weeks later. The oligonucleotide sequences for sgIrs2 are listed in Table 1.

<Preparation Example 5> Generation of Stable Knockdown or Overexpression of Cell Lines To generate knockdown constructs, the plko.1 vector was digested with EcoRI and AgeI and ligated with annealed oligonucleotides encoding SAV1 or PTEN shRNAs (5'-CCGGCGGCTACATCTCTAGGGAATTCTCGAGAAT-TCCCTAGAGATGTAGCCGTTT TT-3' (SEQ ID NO: 65) and 5'-CCGGCAACCGATACTTCTCTC-CAAACTCGAGTTTGGAGAGAAGTATCGGTTGTTT TT-3' (SEQ ID NO: 66), respectively). The shRNA constructs were transfected into 293T cells, together with psPAX2 and pMD2G. After 2 days, viral particles were harvested from the culture media by filtration. The viruses were then used to infect AML12 cells in the presence of polybrene (6 μg/ml) (MilliporeSigma; H9268), and stable cell lines were obtained via antibiotic selection with 10 μg/ml puromycin (Gibco, Thermo Fisher Scientific; A11138-03) or 50 μg/ml hygromycin B (Thermo Fisher Scientific; 1068 7010). The present inventors cloned TAZ4SA, TAZ4SA/S51A, and YAP5SA into pMSCV-puro vector (catalog 631461; Clontech), or purchased IRS2 construct (catalog DU4859; MRC PPU Reagents) for generating AML12 stable cell line expressing those genes, respectively. Next, the resulting constructs were used to prepare recombinant retroviruses for infection and subsequent puromycin selection of infected cells.

<Preparation Example 6> Knockdown of IRS2 with siRNA in AML12 Cells

An AML12 cell line stably expressing shPten and shSav1 was transfected with 20 nM siRNA (ST Pharm Oligo Center) using RNAiMAX (Invitrogen, Thermo Fisher Scientific; 13778-150) according to the manufacturer's instructions. Two days later, the cells were deprived of serum for sixteen hours and then treated with insulin (100 nM). The oligonucleotide sequence information was provided by Calvin J. Kuo (Stanford University School of Medicine, Calif., USA) (Nature Medicine, 2013; 19(10):1331-1337). An AML12 cell line was purchased from ATCC and maintained in DMEM (Gibco, Thermo Fisher Scientific; Ser. No. 12/100, 046) containing 10% FBS (Gibco, Thermo Fisher Scientific; Ser. No. 12/483,020), 1% (w/v) penicillin-streptomycin (Gibco, Thermo Fisher Scientific; Ser. No. 15/140,122), 0.005 mg/ml insulin (Gibco, Thermo Fisher Scientific; Ser. No. 12/585,014), 0.005 mg/ml transferrin (MilliporeSigma; T8158), 5 ng/ml selenium (MilliporeSigma; S5261), and 40 ng/ml dexamethasone (MilliporeSigma; D4902) in a humidity-controlled environment (37° C., 5% $CO_2$). The cell line was confirmed to be *mycoplasma* free with a *Mycoplasma* PCR Detection Kit (Intron; 25233).

<Preparation Example 7> Luciferase Assay

The indicated portions of the Irs2 genomic locus, including 6 potential TBSs, were cloned into the pGL3-Basic vector (Promega). Each mutant construct was generated by deletion of specific TBSs. 293T cells were cotransfected with a *Renilla* plasmid, a TEAD-encoding plasmid, and the constructs of interest. Twenty-four hours later, the cells were harvested, lysed, and assayed with the Dual Luciferase Reporter Assay System (Promega; E1960).

<Preparation Example 8> ChIP-qPCR Analysis

Two days after retrovirus infection, AML12 cells were fixed with 1% (v/v) formaldehyde for 10 minutes and then neutralized with 12 5 mM glycine for 5 minutes at room temperature. The cells were washed with PBS and then lysed with ChIP dilution buffer (50 mM HEPES [pH 7.5], 155 mM NaCl, 1% (v/v) Triton X-100, 0.1% sodium deoxycholate, 1 mM EDTA) containing 1% (w/v) SDS. The DNA in the cell lysates was fragmented by sonication using a Bioruptor sonicator. The cell lysates were centrifuged at 20,000×g for 15 minutes at 4° C., and the resulting supernatants were further diluted with ChIP dilution buffer. The supernatants were then incubated overnight at 4° C. with either the TAZ antibody (MilliporeSigma; HPA007415) or IgG (Santa Cruz Biotechnology). The next day, protein A/G beads (Gendepot) were added, and the samples were incubated for an additional 3 hours at 4° C. The beads were then isolated with centrifugation, washed with ChIP wash buffer (10 mM Tris-HCl [pH 8.0], 250 mM LiCl, 0.5% nonidet P-40, 0.5% sodium deoxycholate, 1 mM EDTA), and suspended in SDS lysis buffer (50 mM Tris-HCl [pH 8.0], 10 mM EDTA, 1% SDS) for overnight incubation at 65° C. The beads were then removed, and the remaining material was incubated for 2 hours at 55° C. with proteinase K (20 mg/ml) and glycogen (20 mg/ml). After a final 1-hour incubation with RNaseA at 37° C., the DNA was purified using standard procedures and analyzed by qPCR using the primers listed in Table 1.

<Preparation Example 9> Gene Expression Profiling and GSEA

Total RNA was extracted from livers with Ribo-EX (GeneAll) and subjected to microarray analysis with MouseRef-8, version 2.0 BeadChip (Illumina). To identify differentially expressed genes, the raw values from all groups of mice were normalized to the mean values for each gene set and log 2 transformed. For the heatmap, the values of 25,697 genes were rank-ordered by their average value for the $Pten^{-/-}\ Sav1^{-/-}$ samples, and 500 high-rank and 500 low-rank values were selected. The Multi-Experiment Viewer program was used to generate the heatmap, and representative genes from the GO_Insulin receptor signaling pathway, KEGG_Insulin signaling pathway, GO_Glucose homeostasis, Reactom_Metabolism of carbohydrates, or Cordenonsi_YAP conserved signature gene clusters were selected from the Broad Institute's Molecular Signatures Database. GSEA was performed using the GenePattern tool from the Broad Institute, with version 5.2 of the Molecular Signature Database libraryies. $Pten^{-/-}\ Sav1^{-/-}$ mice were compared with $Pten^{-/-}$-mice, and representative upregulated genes with a nominal P value of less than 0.05 and a FDR q of less than 0.25 are presented.

<Preparation Example 10> Statistics

Because of individual variation between mice, we used at least 3 to 5 mice per group for all experiments (e.g., immunoblot analyses, qPCR, H&E staining, Oil red O staining, Picrosirius red staining, IHC, etc.). We used only 2 mice per group for the microarray analyses. Group sizes were determined in accordance with previous studies, and no mice were excluded. For the comparison of liver specific mutant mice with WT mice, we used WT littermates for all experiments. We did not randomize the mouse experiments. The H&E staining experiments and microarray analyses were conducted by researchers who were blinded to the mouse genotypes. All data met the assumptions of each statistical test, and the variations between groups were similar. All in vitro experiments were replicated at least 3 times, except for the luciferase assay, which was replicated 5 times. Data are presented as the mean±SEM and analyzed using 1-way ANOVA followed by Tukey's multiple comparisons test, a 2-tailed Student's t test, or a $\chi^2$ test, as appropriate. Statistical analyses were performed with GraphPad Prism 7 (GraphPad Software). P values of less than 0.05 were considered statistically significant. All graphs were generated with GraphPad Prism 7.

Example 1: Deletion of Both Pten and Say 1 in the Liver Promotes NAFLD, NASH, and Tumorigenesis To investigate any potential crosstalk between the Hippo and AKT pathways in vivo, the present inventors first generated liver-specific PTEN and SAV1 double-knockout mice ($Pten^{-/-}\ Sav1^{-/-}$, referred to herein as DKO mice) (FIG. 11, A). There results were represented in FIG. 11, that are: (A) Schematic for the generation of liver-specific DKO mice; (B) Representative H&E staining of combined hepatocellular carcinoma (HCC) and cholangiocarcinoma (CC) tumor types in DKO mouse livers; (C) PAS, Sirius red, and panCK immunohistochemical staining of the livers of mice at the indicated ages; (D-E) Acute adult-stage deletion of Pten and Sav1 induces fatty liver; Microscopic appearance (D) and H&E staining (E) of livers from 6-week-old $Pten^{f/f};Sav1^{f/f}$ mice injected with adenovirus encoding CRE and GFP (control). The embryo of the mouse model were deposited in the Korean Collection of Type Cultures (KCTC) of Korea Research Institute of Bioscience and Biotechnology (KRIBB) in 181, Ipsin-gil, Jeongeup-si, Jeollabuk-do 56212, Republic of Korea, on May 9, 2018, and received the deposit number KCTC 13522BP.

The livers from 5-month-old mice of each genotype are shown in FIG. 1a. Consistent with previous observations, SAV1-deficient ($Sav1^{f/f}$;Albumin-Cre, or $Sav1^{-/-}$) mice had a slight enlargement of the liver, whereas PTEN-deficient (Pten$^{f/f}$;Albumin-Cre, or Pten$^{-/-}$) mice developed fatty livers (FIG. 1a). In contrast, the DKO mice had highly advanced liver tumors at 5 months of age, with significantly increased liver weights at 2 and 4 months of age (FIG. 1a). The tumor-free rate and survival rate for each genotype are shown in FIG. 1b. While Sav1−/− and Pten−/− mice developed liver tumors at 50 to 60 weeks, all DKO mice developed such tumors by 15 weeks (FIG. 1b). Thus, DKO mice showed a marked acceleration of tumorigenesis with a corresponding reduction in survival (FIG. 1b). In addition, while Pten$^{-/-}$ mice developed only HCC, Sav1$^{-/-}$ mice and DKO mice developed both HCC and CC (FIG. 11).

Given that Pten−/− liver cancer proceeds through NAFLD and NASH, the present inventors examined young DKO mice for phenotypic changes occurring prior to tumor development. The results of tissue staining for each age of indicated genotypes are shown in FIG. 1c. One-month-old DKO livers showed excessive fatty acid accumulation (Oil red O), similar to what was observed in NAFLD. This phenotype, however, did not appear in Pten−/− mouse livers until 3 months of age (H&E) (FIG. 1c, lanes 1 and 3).

Example 2: Increased AKT Signaling Accelerates the Development of Fatty Liver in Pten$^{-/-}$;Sav1$^{-/-}$ Mice The present inventors performed gene expression profiling on the DKO mice to explore the mechanism underlying their early development of NAFLD. A heatmap of differentially expressed genes in the livers of 3-month-old mice as revealed by microarray analysis is shown in FIG. 2a. The DKO livers had increased expression of genes related to insulin signaling (i.e., Pdk4, Igfbp1, and Irs2) and reduced expression of genes related to carbohydrate or glucose metabolism (i.e., Pygb, Slc2a2, Pklr, and Aacs) (FIG. 2a). The result of GSEA that performed by the method of Preparation Example 9, for Pten$^{-/-}$;Sav1$^{-/-}$ (DKO) livers compared with Pten$^{-/-}$ livers is shown in FIG. 2b. The present inventors found concentration of gene signatures related to lipogenesis and insulin signaling, including IRS targets and gene sets related to steroid biosynthesis, lipid biosynthesis, and fatty acid metabolism (FIG. 2b and Table 2).

TABLE 2

| Upregulated genes in Pten$^{-/-}$; Sav1$^{-/-}$ | ES | NOM (P value) | FDR (q value) | Collection |
|---|---|---|---|---|
| TNFA_SIGNALING_VIA_NFKB | 2.72 | 0 | 0 | Hallmark |
| ACYL_COA_METABOLIC_PROCESS | 2.49 | 0 | 0.029 | C5.BP:GO |
| STEROID_BIOSYNTHETIC_PROCESS | 2.43 | 0 | 0.039 | C5.BP:GO |
| GUO_TARGETS_OF_IRS1_AND_IRS2 | 2.37 | 0 | 0.015 | C2.CGP |
| LIPID_BIOSYNTHETIC_PROCESS | 2.34 | 0 | 0.058 | C5.BP:GO |
| REGULATION_OF_CELL_GROWTH | 2.29 | 0.004 | 0.069 | C5.BP:GO |
| REGULATION_OF_TOR_SIGNALING | 2.29 | 0 | 0.067 | C5.BP:GO |
| AKT_UP.V1_UP | 2.26 | 0.006 | 0.042 | C6:OS |
| FATTY_ACID_METABOLIC_PROCESS | 2.09 | 0.002 | 0.119 | C5.BP:GO |
| LIPID_HOMEOSTASIS | 2.00 | 0.010 | 0.165 | C5.BP:GO |
| PHOSPHATIDYLINOSITOL_3_PHOSPHATE_BINDING | 1.85 | 0.023 | 0.244 | C5.MF:GO |
| CHOLESTEROL_HOMEOSTASIS | 1.82 | 0.013 | 0.035 | Hallmark |
| IL6_JAK_STAT3_SIGNALING | 1.69 | 0.029 | 0.060 | Hallmark |
| CORDENONSI_YAP_CONSERVED_SIGNATURE | 1.58 | 0.042 | 0.243 | C6:OS |

Acute deletion of Pten and Sav1 in the adult stage using a CRE-encoding adenovirus also consistently led to the development of NAFLD (FIG. 11). DKO mouse livers also had an excessive accumulation of glycogen (PAS) at 1 month of age (FIG. 1c, lane 2) that grew progressively worse with time (Supplemental FIG. 1C). Moreover, 3-month-old DKO livers showed increased apoptosis (TUNEL) and macrophage accumulation (F4/80) (FIG. 1c, lanes 5 and 6, FIG. 11). Because these are associated with advanced NAFLD (H&E) and fibrosis (Picrosirius red) (FIG. 1c, lanes 3 and 4), they suggested progression to NASH.

The liver-to-body weight ratio for mice atg 2 and 4 months of age (left), the liver enzymes (AST and ALT) in the serum of the indicated genotypes (right top), and the graph of quantification of apoptotic cells and macrophages following the TUNEL and F4/80 staining (right bottom) are shown in FIG. 1d. DKO mice showed significantly increased serum AST and ALT levels at 3 months of age (FIG. 1d) as well as increased pan-cytokeratin-positive (pan-CK-positive) hepatic progenitor cells in nonductal regions at 5 months of age (FIG. 11). Collectively, these results indicate that deletion of Sav1 accelerates the progression of Pten−/− livers through the steps of NAFLD, NASH, cirrhosis, and cancer. The present inventors therefore decided to focus on the development of NAFLD as a precursor of liver tumorigenesis.

Based on the above results, the present inventors studied whether AKT acts as important factor in dysregulation of liver metabolism found in DKO mice.

The immunoblot analysis result of AKT signaling components and lipogenesis-related proteins in the livers of 3-month-old mice is shown in FIG. 2c. As expected, Pten deletion led to activation of AKT, as evidenced by increased levels of p-AKT (FIG. 2c). Surprisingly, DKO livers showed even greater AKT activation than did Pten−/− livers, while neither Sav1−/− nor WT livers showed any such activation, presumably because of the presence of PTEN (FIG. 2c). Consistent with this result, DKO livers also showed greater increases downstream of AKT signaling than did Pten−/− livers, including increased phosphorylation of glycogen synthase kinase (p-GSK3β), increased processing of SREBP1c, and upregulation of FAS and ACC (FIG. 2c). This increase in p-GSK3β in DKO livers is also consistent with their excessive accumulation of glycogen (FIG. 1c, PAS staining).

In FIG. 2d, IHC of p-AKT and immunofluorescence staining of PiP$_3$ in the livers of 3-month-old mice are shown. Using IHC, the present inventors also observed increase in p-AKT and PIP$_3$ in DKO hepatocytes but not biliary cells or infiltrated immune cells (FIG. 2d). The result suggesting that the dysregulation of liver metabolism in DKO mice depends on cell-autonomous signaling.

The result of qPCR analysis of relative mRNA levels for lipogenesis- or inflammation-related genes in the livers of 3-month-old mice is shown in FIG. 2e. DKO livers showed increased expression of lipogenesis-related genes (i.e., Fasn, Acc1, and Scd1) and SREBP family genes (i.e., Srebp1a, Srebp1c, and Srebp2) (FIG. 2e). They also showed increased expression of inflammation-related genes such as IL-6 (Il6) and TNF-α (Tnfa), indicating the progression of chronic NAFLD to NASH (FIG. 2e). In summary, DKO livers showed increased AKT activation, lipogenesis, glycogenesis, and inflammation.

Example 3: YAP/TAZ Enhance AKT Activation and the Development of Fatty Liver in the Absence of PTEN To identify the mechanism underlying the enhanced AKT activation in DKO livers, the status of the various hippo pathway components were observed. The result of immunoblot analysis of Hippo pathway components in livers from 3-month-old mice of each genotype is shown in FIG. 3a.

Consistent with the role of SAV1 as an upstream regulator of LATS, SAV1-deficient livers (from both Sav1−/− and DKO mice) showed reduced LATS activation (pLATS) that was also associated with increased levels of YAP but low levels of p-YAP (FIG. 3a). Both Pten$^{-/-}$ and Sav1$^{-/-}$ mice showed increased levels of TAZ compared with expression levels in WT mice, but the increase in TAZ in DKO mice was even greater (FIG. 3a).

FIG. 3b shows the result of immunohiotochemical staining analysis of YAP/TAZ. The present inventors confirmed the increased levels of YAP and TAZ in DKO livers via IHC (FIG. 3b).

The result of quantification of YAP/TAZ localization from FIG. 3b is shown in FIG. 3c, and the expression result of YAP and TAZ after nuclear/cytoplasmic fractionation in livers from 1-month-old mice is shown in FIG. 3d. Interestingly, we found high levels of YAP expression only in the nuclei of DKO mouse liver cells compared with liver cells from the other groups, but the present inventors found abundant TAZ in both the cytoplasm and nuclei (FIGS. 3c and 3d).

The increased expression of YAP/TAZ targets CTGF and CYR61 provided further confirmation of the upregulation of YAP/TAZ activity in DKO livers (FIG. 3a).

To determine whether YAP and TAZ directly promote fatty liver development via AKT activation, the present inventors used an adenovirus to induce overexpression in the liver of active TAZ (TAZ4SA) or a version of YAP (YAP5SA) that cannot be inhibited by LATS. In WT mice, it was found that liver size and morphology remained unaffected 4 days after injection of the viruses inducing the expression of TAZ4SA or YAP5SA (FIG. 3e, FIGS. 12 A and B).

On the other hand, in Pten−/− mice under the same experimental conditions, the expression of TAZ4SA or YAP5SA induced hepatomegaly, promoted the development of NAFLD without fibrosis or inflammation (FIG. 3e, FIGS. 12 A and C), and elicited marked increases in p-AKT and FAS (FIGS. 3f and 3g). The fact that TAZ4SA and YAP5SA did not affect p-AKT levels in WT livers (FIGS. 3f and 3g) suggests that PTEN was able to rapidly convert PIP$_3$ to PIP$_2$ and thereby prevent AKT activation. This observation suggests that PTEN deficiency is a suitable genetic background in which to study the role of YAP/TAZ in AKT signaling and metabolic dysfunction. These results also support the finding that the upregulation of YAP/TAZ promotes fatty liver development in the Pten$^{-/-}$ background by increasing AKT activity.

Example 4: Transcriptional Regulation of Irs2 by YAP/TAZ

The next addressed question was how YAP and TAZ potentiate AKT activity in Pten$^{-/-}$ livers. The result of immunoblot analysis of insulin signaling molecules in the livers of 3-month-old mice is shown in FIG. 4a, and the result of qPCR analysis of Irs2 mRNA levels in the same livers as in FIG. 4a is shown in FIG. 4b. In DKO livers, the present inventors observed a marked increase in PIP3, a direct upstream activator of AKT (FIG. 3d). The present inventors also observed increased levels of p-ERK (FIG. 4a), a downstream target of PIP3. The present inventors therefore hypothesized that YAP and TAZ may serve as upstream regulators of AKT. DKO mice showed dramatic increases in IRS2, but not IR, IRS1, or PI3K (FIG. 4a).

In addition, the increase in Irs2 mRNA observed in DKO mice was more significant than the increase observed in Sav1$^{-/-}$ or Pten$^{-/-}$ mice (FIG. 4b). This is reminiscent of the pattern observed for YAP/TAZ expression in these same animals (FIGS. 3a and 3b) and is consistent with the microarray analysis showing that DKO mice expressed higher levels of Irs2 mRNA and IRS target genes than did Pten$^{-/-}$ mice (FIG. 2a). Together, these results suggest that YAP/TAZ activation in DKO livers increases insulin signaling by upregulating IRS2.

Next, the present inventors used the normal mouse hepatocyte cell line AML12 to further clarify the molecular relationship between YAP/TAZ and IRS2 in vitro. The result of IRS2 immunoblot analysis of when Pten and/or Sav1 expression are suppressed by infecting the cells with lentiviruses encoding shPten and/or shSav1 is shown in FIG. 4c. The present inventors found slight increase in IRS2 expression associated with the depletion of either PTEN or SAV11 in this cell line, but an even greater increase in IRS2 expression associated with the simultaneous knockdown of both PTEN and SAV1 (FIG. 4c).

In FIG. 4d, the result of immunoblot analysis for AKT activity induced by insulin of AML 12 cells manufactured is shown. While SAV1 depletion did not affect insulin-induced AKT activation, depletion of both SAV1 and PTEN enhanced AKT activation by dramatically increasing IRS2 expression (FIG. 4d).

FIG. 4e shows the result of immunoblot analysis of AKT activity of AML12 cells that IRS2 expression is increased and FIG. 4f shows the result of immunoblot analysis that the AKT activity was reduced in the AML 12 cells of FIG. 4c that showed decreased expression of Pten and Sav1 when the expression of Irs2 was suppressed by using siRNA. The present inventors also found that overexpression of IRS2 induced AKT activation (FIG. 4e) and knockdown of IrS2 in PTEN and SAV1-depleted cells attenuated their insulin-induced activation of AKT (FIG. 4f).

Since the transcription factor TEAD binds YAP/TAZ for target gene transcription, it was asked whether YAP/TAZ can directly regulate Irs2 expression through TEAD. The result of immunoblot assay of cells that TAZ4SA or TAZ4SA/S51A was overexpressed, and in control (CTL) is shown in FIG. 4g. TAZ4SA, but not the TEAD-binding deficient mutant (TAZ4SA/S51A), could enhance IRS2 expression and AKT phosphorylation.

FIG. 4h is a schematic diagram of Luciferase (Luc) reporter constructs that include regions of the Irs2 distal promoter and first intron of TEAD binding region (TBSs) or deleted region (TBSsΔ). There are 6 potential TEAD-binding sites (TBSs) within the distal promoter and first intron of Irs2 (FIG. 4h).

The result of luciferase reporter analysis for expression pattern of Luc in FIG. 4h when the CTL, TAZ4SA, or TAZ4SA/S51A was overexpressed is shown in FIG. 4i. TAZ4SA, but not TAZ4SA/S51A, activated reporter constructs containing TBS2, TBS4, or TBS5, but it could not activate reporters lacking these binding sites (TBSsΔ) (FIG. 4i).

FIG. 4j is a graph showing a result of ChIP-qPCR analysis of whether TAZ binds to the Irs2 distal promoter or intron analyzed in FIG. 4i. By performing ChIP-quantitative PcR (qPCR) analysis, the present inventors found that TAZ binds TBS2 and TBS5 of Irs2 (FIG. 4j). These results indicate that YAP/TAZ-TEAD complex directly induces the transcription of Irs2, thereby promoting AKT signaling.

Example 5: Deletion of Yap/Taz or Activation of Hippo Signaling Attenuates Fatty Liver Development by Downregulation of IRS2

To confirm the role of YAP/TAZ in the DKO mouse phenotype, the DKO mice that also carried conditional Yap and/or Taz alleles were generated. A schematic diagram of method to generate $Pten^{-/-};Sav1^{-/-};Yap^{-/-};Taz^{-/-}$ mice is shown in A panel of FIG. 13.

The result of H&E and Oil red O staining of livers from 1-month-old mice is shown in FIG. 5a, the immunoblot analysis result of IRS2/AKT and YAP/TAZ signal transduction pathway is shown in FIG. 5b, and the result of the qPCR analysis of relative Irs2 mRNA levels in the livers of mice as in FIG. 5a is shown in FIG. 5c. The present inventors observed mild improvement in the fatty liver phenotypes of 4-week-old Pten−/− Sav1−/− Taz−/− (PST triple-knockout [TKO]) and Pten−/− Sav1−/− Yap−/− (PSY TKO) mice compared with that seen in DKO mice (FIG. 5a). In contrast, deletion of both Yap and Taz in DKO mice (PSYT quadruple-knockout [QKO]) rescued the DKO fatty liver phenotype (FIG. 5a).

QKO mice also had a reduced abundance of IRS2, p-AKT, p-GSK3β, and FAS (FIG. 5B), and less upregulation of Irs2 mRNA than did DKO mice (FIG. 5C). DKO and either PST or PSY TKO livers did not differ in their p-AKT levels (FIG. 5b), presumably because of some sort of compensatory regulation of YAP or TAZ in TKO livers. We detected a reduced p-YAP/YAP ratio in PST TKO mice compared with DKO mice, suggesting that PST TKO mice have more active YAP. In PSY TKO mice, it was TAZ that appeared in greater abundance than was observed in DKO mice (FIG. 5b).

Liver-to-body weight ratio (B), Sirius red and CK19 immunohistochemical staining of the liver (C), and isolated serum color (D) for 1-month-old mice of the indicated genotypes are shown in FIG. 13. Unexpectedly, although we did not see any reduction in the liver-to-body weight ratio of PSYT QKO mice compared with that of DKO mice, QKO mice developed severe liver fibrosis, and their serum was much yellower than that of WT mice (FIG. 13). As previously reported, Yap−/− Taz−/− mice do not form biliary ducts (CK19-negative) and have chronic liver damage and fibrosis (FIG. 14, A-F). The fibrotic changes we observed in PSYT QKO livers were likely due to the toxicity that arose because of YAP/TAZ ablation-induced malformation of the biliary duct cells (FIG. 13). Despite this complication, our results indicate that loss of Yap/Taz can rescue the NAFLD phenotype in hepatocytes of DKO mice.

Next, to determine whether the components of the Hippo pathway upstream of YAP/TAZ inhibit AKT signaling, we generated Pten−/− mice expressing transgenes encoding either a WT ($MST-WT^{Tg}$) or kinase-dead mutant ($MSTkd^{Tg}$) form of human MST1, which is a binding partner of SAV1 and an activator of the Hippo pathway.

The mating method of above is shown in the A panel of FIG. 15. (B) Liver-to-body weight ratio for 2-month-old mice (each group, n=3) of the indicated genotypes. Data are means±s.e.m. (C-D) Macroscopic appearance (C), and immunoblot analysis (D) of the livers from 2-month-old mice (n=3) of the indicated genotypes are shown in each indicated panels of FIG. 15. MST1 is a binding partner of SAV1 but also a kinase component of Hippo pathway.

Pten−/− MSTWTTg livers, but not Pten−/− MSTkdTg livers, were smaller and had less lipid droplet accumulation than did Pten−/− livers (FIGS. 6a and 6b, FIG. 15 panels B and C). In contrast to $Pten^{-/-}$ $MSTkd^{Tg}$ livers, $Pten^{-/-}$ $MSTWT^{Tg}$ livers also showed lower AKT activation and IRS2 expression than did $Pten^{-/-}$ livers (FIG. 6c, FIG. 15). In addition, overexpression of $MST1WT^{Tg}$, but not $MSTkd^Tg$, increased LATS activation and decreased YAP/TAZ abundance (FIGS. 6b and 6c).

Together, these data indicate that enhanced Hippo pathway activity inhibits AKT signaling, probably by inhibiting YAP/TAZ-mediated regulation of IRS2 and, consequently, attenuates the development of NAFLD.

Example 6: YAP/TAZ and IRS2/p-AKT are Positively Correlated in HCC Patients' Specimens To extend the results in mice to humans, it was examined that the hepatic expression of YAP, TAZ and IRS2 in HCC patients' samples. Scatter plots of $log_e$ (mRNA abundance) values for IRS2 versus TAZ or YAP1 in tissue specimens from each patients are shown in FIG. 7a. The human HCC and cirrhosis databases showed positive correlations between IRS2 and YAP or TAZ mRNA levels (FIG. 7a).

In addition, scatter plots of log 2 (mRNA abundance) values for IRS2 versus CTGF or CYR61 in the samples of FIG. 7a are shown in FIG. 7b. The significantly positive correlations between IRS2 levels and the downstream targets of YAP/TAZ (e.g. CTGF and CYR61) are found (FIG. 7b).

The IHC result of TAZ and IRS2 of HCC patient sample is shown in FIG. 7c, and the IHC result of YAP and IRS2 of the same sample is shown in FIG. 7d. IRS2 protein levels were also positively correlated with TAZ/YAP levels in human HCC samples: 77% of specimens with high TAZ levels and 81% of specimens with high YAP levels also expressed high levels of IRS2 (FIGS. 7c and 7d).

To extend the result of NAFLD-HCC mice to the patients' tissue, the samples of HCC from NAFLD or from non-NAFLD were obtained and expression level was detected. The result images and a quantificated graph are shown in FIGS. 7e and 7f, respectively.

The comparison of IHC intensities of TAZ, YAP, IRS2, and pAKT(S473) protein levels between NAFLD-associated HCC and non-NAFLD HCC is shown in FIG. 16. HCC specimens with associated NAFLD show significantly higher IHC intensities for TAZ, YAP, IRS2, and p-AKT (Ser473) than did HCC samples without NAFLD. These results suggest that YAP and TAZ are critical in the development of fatty liver and its progression to liver cancer in humans via the upregulation of IRS2 and subsequent AKT activation.

Example 7: Inhibition of AKT Signaling of Silencing of IRS2 Attenuates the Development of Liver Cancer Given the lack of treatments for NASH, the present inventors next asked whether pharmacological inhibition of AKT could ameliorate fatty liver and slow cancer progression in DKO mice. To this end, the present inventors administered the pan-AKT inhibitor MK-2206 (phase II clinical trials) intraperitoneally to 3-week-old DKO mice. The schematic image of specific experimental method is shown in FIG. 8a (top).

Macroscopic appearance of the liver (middle) as well as H&E and Oil red O staining (bottom) are shown in FIG. 8a. FIGS. 8b to 8d are graphs of the result of liver-to-body weight ratio percentage, the analysis of liver enzymes in the serum, the qPCR analysis of lipogenesis-related gene expression in the liver of control (white bars) and MK-2206 (red bars), respectively. FIG. 17 shows Sirius red and YAP staining result of mice. The present inventors found that MK-2206-treated DKO mice had less fatty liver, decreased liver weight, and reduced liver fibrosis as well as improved liver function and lower expression of lipogenesis-related genes (i.e. Fasn, Acc1, and Srebp1c) than did vehicle-treated DKO (control) mice (FIGS. 8a to 8d, FIG. 17).

Further, to investigate the suppression of liver cancer, MK-2206 was injected to 12-week-old DKO mice that 80% of them had liver tumor (FIG. 1b). The experimental method and the macroscopic result are shown in FIG. 8e. The graphs of FIG. 8f are the result of the result of liver-to-body weight ratio (F), liver tumor number and size (G), serum analysis (H) of the experiment shown in FIG. 8f. The graph representing the quantification analysis of Ki-67$^+$ hepatocytes of specimen is shown in FIG. 8h, and a graph representing the qPCR analysis of the expression of genes related to fibrosis (Acta2, desmin, and Tgfb), cell death or injury (Hmox1 and Gadd153), or inflammation (Tnfa) is shown in FIG. 8i. The MK-2206-treated DKO mice showed reduced fatty liver and tumorigenesis, as revealed by their reduced liver size, normalized liver color, and reduction in tumor nodule size (FIGS. 8e to 8f). MK-2206-treated DKO livers had fewer hepatocytes with excessive lipid droplets (H&E), reduced fibrosis (Picrosirius red), fewer Ki-67-positive cells, and lower levels of hepatocyte TAZ expression without a corresponding change in YAP expression (FIGS. 8g to 8h, FIG. 17, panel B).

These effects were also accompanied by reduced expression of genes related to fibrosis (i.e., Acta2, desmin, and Tgfb), cell death or injury (i.e., Hmox1 and Gadd153), and inflammation (i.e., Tnfa) (FIG. 8i). Together, these results indicate that, like Hippo pathway activation (FIGS. 6a to 6c), AKT inhibitor treatment markedly attenuates the development of NAFLD and liver cancer in DKO mice.

To clarify the role that IRS2 plays in the development of NAFLD and cancer in DKO mice in vivo, we generated an adeno-associated virus (AAV) encoding *Staphylococcus aureus* Cas9 (saCas9) and single-guide RNA (sgRNA) against Irs2 (sgIrs2) to abrogate IRS2 expression in the DKO mouse liver. The analysis results after injection of AAV virus encoding Cas9 and an sgRNA against Irs2 (sgIrs2) or an sgCtl into 5-week-old DKO mice are shown in FIGS. 9a to 9d.

Specifically, FIG. 9a is a picture of macropic appearance of liver, FIG. 9b is the result of immunoblot, FIG. 9c are two graphs representing liver-to-body weight ratio (left) and liver tumor number and size (right), and FIG. 9d is the result of H&E staining of livers. Importantly, the present inventors found that deletion of Irs2 in DKO livers rescued the cancerous phenotypes of control virus-injected (sgCtl-injected) DKO mice. sgIrs2-injected DKO livers showed significant reductions in the number and size of cancer nodules by reducing their levels of p-AKT (FIGS. 9a to 9c). However any attenuation of NAFLD progression by injection of sgIrs2 into 5-week-old mice, which already had advanced NAFLD does not detected (FIG. 9d). Because the rapid progression of tumor formation in DKO livers stems from their enhanced development of fatty liver, the suppression of IRS2 significantly prevents disease progression from NAFLD to cancer. Collectively, these results suggest that increased IRS2 expression in DKO liver is the key factor promoting liver cancer progression. The schematic diagrams for positive feedback loop between Hippo and AKT signaling in DKO liver are represented in FIG. 10.

The invention claimed is:

1. An animal model of non-alcoholic liver disease in which the Pten and Sav1 genes are deleted specifically in a liver, wherein the non-alcoholic liver disease is selected from the group consisting of non-alcoholic fatty liver, non-alcoholic hepatosteatitis, cirrhosis, and liver cancer.

2. The animal model of non-alcoholic liver disease of claim 1, wherein the animal model is obtained from embryos with accession number of KCTC 13522BP.

3. A method of screening for a therapeutic agent for non-alcoholic liver disease comprising:
   (i) treating an animal model according to claim 1 with a candidate substance for a therapeutic agent for non-alcoholic liver disease;
   (ii) measuring the expression level or the activity level of at least one protein selected from the group consisting of YAP, TAZ, IRS2 and AKT proteins in the liver tissue of the animal model treated with the candidate substance; and
   (iii) determining the candidate substance as the therapeutic agent for liver disease when the expression level or the activity level measured in (ii) is lower than the expression level or the activity level of the same one or more proteins when measured in a control liver tissue of the animal model untreated with the candidate substance.

4. The method of claim 3, wherein the step of measuring the expression level or the activity level of protein is performed by measuring the transcription level of mRNA.

5. The method of claim 4, wherein the measuring transcription level of mRNA is performed by at least one method selected from the group consisting of PCR, reverse transcription PCR (RT-PCR), real-time PCR, RNase protection assay (RPA), microarray, and northern blotting.

6. The method of claim 3, wherein the measuring the expression level or the activity level of protein is performed by at least one method selected from the group consisting of western blotting, radioimmunoassay (RIA), radioimmunodiffusion, ELISA, immunoprecipitation (IP), flow cytometry, immunofluorescence, ouchterlony, complement fixation assay, and protein chip.

7. The method of claim 3, wherein the candidate substance comprises a primer, probe, aptamer, antisense oligonucleotide, polymeric compound, protein, peptide, nucleic acid molecule, virus, or antibody.

8. The method of claim 3, wherein the candidate substance inhibits the activity of AKT protein.

9. A method of manufacturing an animal model for non-alcoholic liver disease in which the Pten and Sav1 genes are deleted specifically in a liver, comprising:
   obtaining a first-generation animal by mating an animal of $Pten^{f/f}$ genotype and an animal of Albumin-Cre genotype expressing CRE;
   obtaining a second-generation animal by mating the first-generation animal and an animal of $Sav1^{f/f}$ genotype; and
   obtaining a third-generation animal comprising $Pten^{f/f}$; $Sav1^{f/f}$;Albumin-Cre genotype by mating between the second-generation animals.

* * * * *

SEQUENCE LISTING

<160> NUMBER OF SEQ ID NOS: 66

<210> SEQ ID NO 1
<211> LENGTH: 18
<212> TYPE: DNA
<213> ORGANISM: Artificial Sequence
<220> FEATURE:
<223> OTHER INFORMATION: Synthetic (RT-qPCR_Srebp1a_Sense)

<400> SEQUENCE: 1
ggccgagatg tgcgaact                                                   18

<210> SEQ ID NO 2
<211> LENGTH: 22
<212> TYPE: DNA
<213> ORGANISM: Artificial Sequence
<220> FEATURE:
<223> OTHER INFORMATION: Synthetic (RT-qPCR_Srebp1a_Antisense)

<400> SEQUENCE: 2
ttgttgatga gctggagcat gt                                              22

<210> SEQ ID NO 3
<211> LENGTH: 20
<212> TYPE: DNA
<213> ORGANISM: Artificial Sequence
<220> FEATURE:
<223> OTHER INFORMATION: Synthetic (RT-qPCR_Srebp1c_Sense)

<400> SEQUENCE: 3
ggagccatgg attgcacatt                                                 20

<210> SEQ ID NO 4
<211> LENGTH: 20
<212> TYPE: DNA
<213> ORGANISM: Artificial Sequence
<220> FEATURE:
<223> OTHER INFORMATION: Synthetic (RT-qPCR_Srebp1c_Antisense)

<400> SEQUENCE: 4
caggaaggct tccagagagg                                                 20

<210> SEQ ID NO 5
<211> LENGTH: 19
<212> TYPE: DNA
<213> ORGANISM: Artificial Sequence
<220> FEATURE:
<223> OTHER INFORMATION: Synthetic (RT-qPCR_Srebp2_Sense)

<400> SEQUENCE: 5
gcgttctgga gaccatgga                                                  19

<210> SEQ ID NO 6
<211> LENGTH: 25
<212> TYPE: DNA
<213> ORGANISM: Artificial Sequence
<220> FEATURE:
<223> OTHER INFORMATION: Synthetic (RT-qPCR_Srebp2_Antisense)

<400> SEQUENCE: 6
acaaagttgc tctgaaaaca aatca                                           25

<210> SEQ ID NO 7
<211> LENGTH: 20
<212> TYPE: DNA
<213> ORGANISM: Artificial Sequence
<220> FEATURE:
<223> OTHER INFORMATION: Synthetic (RT-qPCR_Fasn_Sense)

<400> SEQUENCE: 7
gcctacaccc agagctaccg                                                 20

<210> SEQ ID NO 8
<211> LENGTH: 19
<212> TYPE: DNA
<213> ORGANISM: Artificial Sequence
<220> FEATURE:
<223> OTHER INFORMATION: Synthetic (RT-qPCR_Fasn_Antisense)

<400> SEQUENCE: 8
gccatggtac ttggccttg                                                  19

<210> SEQ ID NO 9
<211> LENGTH: 21
<212> TYPE: DNA

```
<213> ORGANISM: Artificial Sequence
<220> FEATURE:
<223> OTHER INFORMATION: Synthetic (RT-qPCR_Acc1_Sense)

<400> SEQUENCE: 9
caacgagatt tcactgtggc t                                    21

<210> SEQ ID NO 10
<211> LENGTH: 22
<212> TYPE: DNA
<213> ORGANISM: Artificial Sequence
<220> FEATURE:
<223> OTHER INFORMATION: Synthetic (RT-qPCR_Acc1_Antisense)

<400> SEQUENCE: 10
ttctgcattg gctttaaggt ct                                   22

<210> SEQ ID NO 11
<211> LENGTH: 20
<212> TYPE: DNA
<213> ORGANISM: Artificial Sequence
<220> FEATURE:
<223> OTHER INFORMATION: Synthetic (RT-qPCR_Scd1_Sense)

<400> SEQUENCE: 11
ccggagaccc cttagatcga                                      20

<210> SEQ ID NO 12
<211> LENGTH: 25
<212> TYPE: DNA
<213> ORGANISM: Artificial Sequence
<220> FEATURE:
<223> OTHER INFORMATION: Synthetic (RT-qPCR_Scd1_Antisense)

<400> SEQUENCE: 12
tagcctgtaa agatttctgc aaacc                                25

<210> SEQ ID NO 13
<211> LENGTH: 20
<212> TYPE: DNA
<213> ORGANISM: Artificial Sequence
<220> FEATURE:
<223> OTHER INFORMATION: Synthetic (RT-qPCR_Tnfa_Sense)

<400> SEQUENCE: 13
catcttctca aaattcgagt                                      20

<210> SEQ ID NO 14
<211> LENGTH: 19
<212> TYPE: DNA
<213> ORGANISM: Artificial Sequence
<220> FEATURE:
<223> OTHER INFORMATION: Synthetic (RT-qPCR_Tnfa_Antisense)

<400> SEQUENCE: 14
tgggagtgac aaggtacaa                                       19

<210> SEQ ID NO 15
<211> LENGTH: 20
<212> TYPE: DNA
<213> ORGANISM: Artificial Sequence
<220> FEATURE:
<223> OTHER INFORMATION: Synthetic (RT-qPCR_Il6_Sense)

<400> SEQUENCE: 15
tccacgattt cccagagaac                                      20
```

<210> SEQ ID NO 16
<211> LENGTH: 20
<212> TYPE: DNA
<213> ORGANISM: Artificial Sequence
<220> FEATURE:
<223> OTHER INFORMATION: Synthetic (RT-qPCR_Il6_Antisense)

<400> SEQUENCE: 16
agttgccttc ttgggactga        20

<210> SEQ ID NO 17
<211> LENGTH: 20
<212> TYPE: DNA
<213> ORGANISM: Artificial Sequence
<220> FEATURE:
<223> OTHER INFORMATION: Synthetic (RT-qPCR_Irs2_Sense)

<400> SEQUENCE: 17
caagagccct ggcgagtaca        20

<210> SEQ ID NO 18
<211> LENGTH: 18
<212> TYPE: DNA
<213> ORGANISM: Artificial Sequence
<220> FEATURE:
<223> OTHER INFORMATION: Synthetic (RT-qPCR_Irs2_Antisense)

<400> SEQUENCE: 18
ccgcggatgc cagtagtg        18

<210> SEQ ID NO 19
<211> LENGTH: 24
<212> TYPE: DNA
<213> ORGANISM: Artificial Sequence
<220> FEATURE:
<223> OTHER INFORMATION: Synthetic (RT-qPCR_Acta2_Sense)

<400> SEQUENCE: 19
atgctcccag ggctgttttc ccat        24

<210> SEQ ID NO 20
<211> LENGTH: 25
<212> TYPE: DNA
<213> ORGANISM: Artificial Sequence
<220> FEATURE:
<223> OTHER INFORMATION: Synthetic (RT-qPCR_Acta2_Antisense)

<400> SEQUENCE: 20
gtggtgccag atcttttcca tgtcg        25

<210> SEQ ID NO 21
<211> LENGTH: 20
<212> TYPE: DNA
<213> ORGANISM: Artificial Sequence
<220> FEATURE:
<223> OTHER INFORMATION: Synthetic (RT-qPCR_Desmin_Sense)

<400> SEQUENCE: 21
ctaaaggatg agatggcccg        20

<210> SEQ ID NO 22
<211> LENGTH: 22
<212> TYPE: DNA
<213> ORGANISM: Artificial Sequence
<220> FEATURE:

```
<223> OTHER INFORMATION: Synthetic (RT-qPCR_Desmin_Antisense)

<400> SEQUENCE: 22
gaaggtctgg ataggaaggt tg                                              22

<210> SEQ ID NO 23
<211> LENGTH: 19
<212> TYPE: DNA
<213> ORGANISM: Artificial Sequence
<220> FEATURE:
<223> OTHER INFORMATION: Synthetic (RT-qPCR_Tgfb_Sense)

<400> SEQUENCE: 23
ctcccgtggc ttctagtgc                                                  19

<210> SEQ ID NO 24
<211> LENGTH: 22
<212> TYPE: DNA
<213> ORGANISM: Artificial Sequence
<220> FEATURE:
<223> OTHER INFORMATION: Synthetic (RT-qPCR_Tgfb_Antisense)

<400> SEQUENCE: 24
gccttagttt ggacaggatc tg                                              22

<210> SEQ ID NO 25
<211> LENGTH: 19
<212> TYPE: DNA
<213> ORGANISM: Artificial Sequence
<220> FEATURE:
<223> OTHER INFORMATION: Synthetic (RT-qPCR_Hmox1_Sense)

<400> SEQUENCE: 25
gctcgaatga acactctgg                                                  19

<210> SEQ ID NO 26
<211> LENGTH: 19
<212> TYPE: DNA
<213> ORGANISM: Artificial Sequence
<220> FEATURE:
<223> OTHER INFORMATION: Synthetic (RT-qPCR_Hmox1_Antisense)

<400> SEQUENCE: 26
gttcctctgt cagcatcac                                                  19

<210> SEQ ID NO 27
<211> LENGTH: 21
<212> TYPE: DNA
<213> ORGANISM: Artificial Sequence
<220> FEATURE:
<223> OTHER INFORMATION: Synthetic (RT-qPCR_Gadd 153_Sense)

<400> SEQUENCE: 27
ctggaagcct ggtatgagga t                                               21

<210> SEQ ID NO 28
<211> LENGTH: 22
<212> TYPE: DNA
<213> ORGANISM: Artificial Sequence
<220> FEATURE:
<223> OTHER INFORMATION: Synthetic (RT-qPCR_Gadd 153_Antisense)

<400> SEQUENCE: 28
cagggtcaag agtagtgaag gt                                              22
```

```
<210> SEQ ID NO 29
<211> LENGTH: 24
<212> TYPE: DNA
<213> ORGANISM: Artificial Sequence
<220> FEATURE:
<223> OTHER INFORMATION: Synthetic (Luciferase Reporter
      construct_TBS1_Sense)

<400> SEQUENCE: 29
cttatctggc agcaggaagg agag                                          24

<210> SEQ ID NO 30
<211> LENGTH: 24
<212> TYPE: DNA
<213> ORGANISM: Artificial Sequence
<220> FEATURE:
<223> OTHER INFORMATION: Synthetic (Luciferase Reporter
      construct_TBS1_Antisense)

<400> SEQUENCE: 30
cacaccctcg cacacatatc cctc                                          24

<210> SEQ ID NO 31
<211> LENGTH: 24
<212> TYPE: DNA
<213> ORGANISM: Artificial Sequence
<220> FEATURE:
<223> OTHER INFORMATION: Synthetic (Luciferase Reporter
      construct_TBS2_Sense)

<400> SEQUENCE: 31
cacccttgca cacgtagaga cgct                                          24

<210> SEQ ID NO 32
<211> LENGTH: 23
<212> TYPE: DNA
<213> ORGANISM: Artificial Sequence
<220> FEATURE:
<223> OTHER INFORMATION: Synthetic (Luciferase Reporter
      construct_TBS2_Antisense)

<400> SEQUENCE: 32
accgtgttca cccagcaccc ggg                                           23

<210> SEQ ID NO 33
<211> LENGTH: 22
<212> TYPE: DNA
<213> ORGANISM: Artificial Sequence
<220> FEATURE:
<223> OTHER INFORMATION: Synthetic (Luciferase Reporter
      construct_TBS3_Sense)

<400> SEQUENCE: 33
cctggcagtg tcccatagtt ga                                            22

<210> SEQ ID NO 34
<211> LENGTH: 21
<212> TYPE: DNA
<213> ORGANISM: Artificial Sequence
<220> FEATURE:
<223> OTHER INFORMATION: Synthetic (Luciferase Reporter
      construct_TBS3_Antisense)

<400> SEQUENCE: 34
cagctgctgc ttctttaggg g                                             21

<210> SEQ ID NO 35
```

-continued

```
<211> LENGTH: 22
<212> TYPE: DNA
<213> ORGANISM: Artificial Sequence
<220> FEATURE:
<223> OTHER INFORMATION: Synthetic (Luciferase Reporter
      construct_TBS4_Sense)

<400> SEQUENCE: 35
gcagcagctg aagtgctaaa ga                                             22

<210> SEQ ID NO 36
<211> LENGTH: 21
<212> TYPE: DNA
<213> ORGANISM: Artificial Sequence
<220> FEATURE:
<223> OTHER INFORMATION: Synthetic (Luciferase Reporter
      construct_TBS4_Antisense)

<400> SEQUENCE: 36
gctgctttcc tctcattgct c                                              21

<210> SEQ ID NO 37
<211> LENGTH: 22
<212> TYPE: DNA
<213> ORGANISM: Artificial Sequence
<220> FEATURE:
<223> OTHER INFORMATION: Synthetic (Luciferase Reporter
      construct_TBS5_Sense)

<400> SEQUENCE: 37
gcctctgagc caacatctct ct                                             22

<210> SEQ ID NO 38
<211> LENGTH: 21
<212> TYPE: DNA
<213> ORGANISM: Artificial Sequence
<220> FEATURE:
<223> OTHER INFORMATION: Synthetic (Luciferase Reporter
      construct_TBS5_Antisense)

<400> SEQUENCE: 38
tatgacctcc cacccacttc a                                              21

<210> SEQ ID NO 39
<211> LENGTH: 22
<212> TYPE: DNA
<213> ORGANISM: Artificial Sequence
<220> FEATURE:
<223> OTHER INFORMATION: Synthetic (Luciferase Reporter
      construct_TBS6_Sense)

<400> SEQUENCE: 39
catggctcgt ttctccttct gg                                             22

<210> SEQ ID NO 40
<211> LENGTH: 21
<212> TYPE: DNA
<213> ORGANISM: Artificial Sequence
<220> FEATURE:
<223> OTHER INFORMATION: Synthetic (Luciferase Reporter
      construct_TBS6_Antisense)

<400> SEQUENCE: 40
gagtactcag gcccaggatg c                                              21

<210> SEQ ID NO 41
<211> LENGTH: 23
```

<210> SEQ ID NO 41
<211> LENGTH: 23
<212> TYPE: DNA
<213> ORGANISM: Artificial Sequence
<220> FEATURE:
<223> OTHER INFORMATION: Synthetic (ChIP-qPCR_TBS1_Sense)

<400> SEQUENCE: 41
atctatggtc ttcagaatca cac                                                23

<210> SEQ ID NO 42
<211> LENGTH: 26
<212> TYPE: DNA
<213> ORGANISM: Artificial Sequence
<220> FEATURE:
<223> OTHER INFORMATION: Synthetic (ChIP-qPCR_TBS1_Antisense)

<400> SEQUENCE: 42
ccagagttta tcttacaatt taacct                                             26

<210> SEQ ID NO 43
<211> LENGTH: 25
<212> TYPE: DNA
<213> ORGANISM: Artificial Sequence
<220> FEATURE:
<223> OTHER INFORMATION: Synthetic (ChIP-qPCR_TBS2_Sense)

<400> SEQUENCE: 43
cacagtttac acaaagggta aagca                                              25

<210> SEQ ID NO 44
<211> LENGTH: 23
<212> TYPE: DNA
<213> ORGANISM: Artificial Sequence
<220> FEATURE:
<223> OTHER INFORMATION: Synthetic (ChIP-qPCR_TBS2_Antisense)

<400> SEQUENCE: 44
gctctggatg cgtaaacaaa aca                                                23

<210> SEQ ID NO 45
<211> LENGTH: 21
<212> TYPE: DNA
<213> ORGANISM: Artificial Sequence
<220> FEATURE:
<223> OTHER INFORMATION: Synthetic (ChIP-qPCR_TBS4_Sense)

<400> SEQUENCE: 45
gcagcagttg attcccatcc t                                                  21

<210> SEQ ID NO 46
<211> LENGTH: 20
<212> TYPE: DNA
<213> ORGANISM: Artificial Sequence
<220> FEATURE:
<223> OTHER INFORMATION: Synthetic (ChIP-qPCR_TBS4_Antisense)

<400> SEQUENCE: 46
acaatggggc agggaaggta                                                    20

<210> SEQ ID NO 47
<211> LENGTH: 24
<212> TYPE: DNA
<213> ORGANISM: Artificial Sequence
<220> FEATURE:
<223> OTHER INFORMATION: Synthetic (ChIP-qPCR_TBS5_Sense)

<400> SEQUENCE: 47

```
gtaaaaccca gaaaccccac tttc                                          24

<210> SEQ ID NO 48
<211> LENGTH: 22
<212> TYPE: DNA
<213> ORGANISM: Artificial Sequence
<220> FEATURE:
<223> OTHER INFORMATION: Synthetic (ChIP-qPCR_TBS5_Antisense)

<400> SEQUENCE: 48
tgctctgctt ctctcactag ga                                            22

<210> SEQ ID NO 49
<211> LENGTH: 20
<212> TYPE: DNA
<213> ORGANISM: Artificial Sequence
<220> FEATURE:
<223> OTHER INFORMATION: Synthetic (Mouse genotype check_Sav1_Sense)

<400> SEQUENCE: 49
tggtttgctt tttagtggcc                                               20

<210> SEQ ID NO 50
<211> LENGTH: 20
<212> TYPE: DNA
<213> ORGANISM: Artificial Sequence
<220> FEATURE:
<223> OTHER INFORMATION: Synthetic (Mouse genotype check_Sav1_Antisense)

<400> SEQUENCE: 50
tgctggtttt gtctcactaa                                               20

<210> SEQ ID NO 51
<211> LENGTH: 21
<212> TYPE: DNA
<213> ORGANISM: Artificial Sequence
<220> FEATURE:
<223> OTHER INFORMATION: Synthetic (Mouse genotype check_Pten_Sense)

<400> SEQUENCE: 51
ctcctctact ccattcttcc c                                             21

<210> SEQ ID NO 52
<211> LENGTH: 20
<212> TYPE: DNA
<213> ORGANISM: Artificial Sequence
<220> FEATURE:
<223> OTHER INFORMATION: Synthetic (Mouse genotype check_Pten_Antisense)

<400> SEQUENCE: 52
actcccacca atgaacaaac                                               20

<210> SEQ ID NO 53
<211> LENGTH: 27
<212> TYPE: DNA
<213> ORGANISM: Artificial Sequence
<220> FEATURE:
<223> OTHER INFORMATION: Synthetic (Mouse genotype check_Yap1_Sense)

<400> SEQUENCE: 53
acatgtaggt ctgcatgcca gaggagg                                       27

<210> SEQ ID NO 54
<211> LENGTH: 27
<212> TYPE: DNA
<213> ORGANISM: Artificial Sequence
```

```
<220> FEATURE:
<223> OTHER INFORMATION: Synthetic (Mouse genotype check_Yap1_Antisense)

<400> SEQUENCE: 54
aggctgagac aggaggatct ctgtgag                                              27

<210> SEQ ID NO 55
<211> LENGTH: 32
<212> TYPE: DNA
<213> ORGANISM: Artificial Sequence
<220> FEATURE:
<223> OTHER INFORMATION: Synthetic (Mouse genotype check_Taz_Sense)

<400> SEQUENCE: 55
ggcttgtgac aaagaacctg gggctatctg ag                                        32

<210> SEQ ID NO 56
<211> LENGTH: 31
<212> TYPE: DNA
<213> ORGANISM: Artificial Sequence
<220> FEATURE:
<223> OTHER INFORMATION: Synthetic (Mouse genotype check_Taz_Antisense)

<400> SEQUENCE: 56
cccacagtta aatgcttctc ccaagactgg g                                         31

<210> SEQ ID NO 57
<211> LENGTH: 19
<212> TYPE: DNA
<213> ORGANISM: Artificial Sequence
<220> FEATURE:
<223> OTHER INFORMATION: Synthetic (Mouse genotype check_Cre_Sense)

<400> SEQUENCE: 57
gtgttgccgc gccatctgc                                                       19

<210> SEQ ID NO 58
<211> LENGTH: 24
<212> TYPE: DNA
<213> ORGANISM: Artificial Sequence
<220> FEATURE:
<223> OTHER INFORMATION: Synthetic (Mouse genotype check_Cre_Antisense)

<400> SEQUENCE: 58
caccattgcc cctgtttcac tatc                                                 24

<210> SEQ ID NO 59
<211> LENGTH: 22
<212> TYPE: DNA
<213> ORGANISM: Artificial Sequence
<220> FEATURE:
<223> OTHER INFORMATION: Synthetic (Mouse genotype check_MSTTg_Sense)

<400> SEQUENCE: 59
gctctagagc ctctgctaac ca                                                   22

<210> SEQ ID NO 60
<211> LENGTH: 19
<212> TYPE: DNA
<213> ORGANISM: Artificial Sequence
<220> FEATURE:
<223> OTHER INFORMATION: Synthetic (Mouse genotype
      check_MSTTg_Antisense)

<400> SEQUENCE: 60
ccagggacca gatgtctgc                                                       19
```

<210> SEQ ID NO 61
<211> LENGTH: 24
<212> TYPE: DNA
<213> ORGANISM: Artificial Sequence
<220> FEATURE:
<223> OTHER INFORMATION: Synthetic (Andenovirus sgIrs2_Ex1-1_Sense)

<400> SEQUENCE: 61
caccgatcgc cctctacacc aagg                                          24

<210> SEQ ID NO 62
<211> LENGTH: 24
<212> TYPE: DNA
<213> ORGANISM: Artificial Sequence
<220> FEATURE:
<223> OTHER INFORMATION: Synthetic (Andenovirus sgIrs4_Ex1-1_Antisense)

<400> SEQUENCE: 62
aaacccttgg tgtagagggc gatc                                          24

<210> SEQ ID NO 63
<211> LENGTH: 24
<212> TYPE: DNA
<213> ORGANISM: Artificial Sequence
<220> FEATURE:
<223> OTHER INFORMATION: Synthetic (Andenovirus sgIrs3_Ex1-2_Sense)

<400> SEQUENCE: 63
caccgccgcc gcagcctccg cggc                                          24

<210> SEQ ID NO 64
<211> LENGTH: 24
<212> TYPE: DNA
<213> ORGANISM: Artificial Sequence
<220> FEATURE:
<223> OTHER INFORMATION: Synthetic (Andenovirus sgIrs5_Ex1-2_Antisense)

<400> SEQUENCE: 64
aaacgccgcg gaggctgcgg cggc                                          24

<210> SEQ ID NO 65
<211> LENGTH: 57
<212> TYPE: DNA
<213> ORGANISM: Artificial Sequence
<220> FEATURE:
<223> OTHER INFORMATION: Synthetic (SAV1 shRNA)

<400> SEQUENCE: 65
ccggcggcta catctctagg gaattctcga gaattcccta gagatgtagc cgttttt      57

<210> SEQ ID NO 66
<211> LENGTH: 57
<212> TYPE: DNA
<213> ORGANISM: Artificial Sequence
<220> FEATURE:
<223> OTHER INFORMATION: Synthetic (PTEN shRNA)

<400> SEQUENCE: 66
ccggcaaccg atacttctct ccaaactcga gtttggagag aagtatcggt tgttttt      57